US006027884A

United States Patent [19]
Lane et al.

[11] Patent Number: 6,027,884
[45] Date of Patent: *Feb. 22, 2000

[54] THERMODYNAMICS, DESIGN, AND USE OF NUCLEIC ACID SEQUENCES

[75] Inventors: Michael J. Lane, Baldwinsville, N.Y.; Albert S. Benight, Schaumburg, Ill.; Brian D. Faldasz, Maynard, Mass.

[73] Assignee: The Research Foundation of the State University of New York, Albany, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/763,417

[22] Filed: Dec. 11, 1996

Related U.S. Application Data

[63] Continuation of application No. 08/260,200, Jun. 16, 1994, abandoned, which is a continuation-in-part of application No. 08/224,840, Apr. 8, 1994, abandoned, which is a continuation-in-part of application No. 08/078,759, Jun. 17, 1993, abandoned.

[51] Int. Cl.$^7$ .............. C12Q 1/68; C12Q 1/70; C12P 19/34; C07H 21/00
[52] U.S. Cl. ............... 435/6; 435/5; 536/24.3; 536/24.33
[58] Field of Search .................. 435/5, 91.1, 6, 435/91.2; 536/24.3, 24.33

[56] References Cited

U.S. PATENT DOCUMENTS

| | | | |
|---|---|---|---|
| 4,795,701 | 1/1989 | Vary | 435/6 |
| 4,820,630 | 4/1989 | Taub | 435/5 |
| 4,876,187 | 10/1989 | Duck et al. | 435/6 |
| 5,011,769 | 4/1991 | Duck et al. | 435/6 |
| 5,403,707 | 4/1995 | Alwood et al. | 435/5 |
| 5,593,834 | 1/1997 | Lane et al. | 435/6 |

FOREIGN PATENT DOCUMENTS

| | | |
|---|---|---|
| 32944/89 | 10/1989 | Australia . |
| 0 227 976 | 7/1987 | European Pat. Off. . |
| WO 89/09284 | 10/1989 | WIPO . |
| WO 92/01047 | 1/1992 | WIPO . |

OTHER PUBLICATIONS

Saiki,R.K., et al., "Primer–Directed Enzymatic Amplification of DNA with a Thermostable DNA Polymerase", *Science*, vol. 239, pp. 487–491, 1988.

Panaccio, M., et al., "PCR based Diagnosis in the Presence of 8% (v/v) Blood", *Nucl. Acids. Res.*, vol. 19, p. 1151, 1991.

McGhee, J.D. "Theoretical Calculations of the Helix–Coil Transition of DNA in the Presence of Large, Cooperatively Binding Ligands" *Biopolymers*, vol. 15, pp. 1345–1375 (1976).

Bishop, K.D. et al., "Actinomycin D induced DNase I hypersensitivity and asymmetric structure transmission in a DNA dodecamer" *Nucleic Acids Research*, vol. 19, pp. 871–875 (1991).

Amaratunga, M. et al., Studies of DNA Dumbbells. II. Construction and Characterization of DNA Dumbbells with a 16 Base–Pair Duplex Stem and $T_n$ End Loops (n=2,3,4, 6,8,10,14) *Biopolymers*, vol. 21, pp. 865–869, 1992.

Doktycz, M. et al., "Studies of DNA Dumbbells. I. Melting Curves of 17 DNA Dumbbells with Different Duplex Stem Sequences Linked by $T_4$ Endloops: Evaluation of the Nearest–Neighbor Stacking Interactions in DNA" *Biopolymers*, vol. 32, pp. 849–864, 1992.

Goldstein, R.F. and A.S. Benight, "How Many Numbers Are Required to Specify Sequence–Dependent Properties of Polynucleotides?" *Biopolymers*, vol. 32, pp. 1679–1693, 1992.

Lowe et al. (1990) "A Computer Program for Selection of Oligonucleotide Primers for Polymerase Chain Reactions" Nucleic Acids Res. 18:1757–1761.

Sugimoto et al. (1993) "Quantitive Detection of DNA by Coamplification Polymerase Chain Reaction: A Wide Detectable Range Controlled by . . . " Anal. Biochem. 211:170–172.

Rychilik (1993) "Selection of Primers for Polymerase Chain Reaction" in White (ed.) Methods in Enzymology, v. 15, PCR Protocols; Totowa, N.J.; Humana Press, pp. 31–40.

*Primary Examiner*—Scott D. Priebe
*Attorney, Agent, or Firm*—Lahive & Cockfield, LLP; Giulio A. DeConti, Jr.; Nicholas P. Triano, III

[57] ABSTRACT

A method of providing the sequence of a single stranded nucleic acid molecule, which, when hybridized to a complementary single stranded molecule, results in a double stranded (duplex) structure having a preselected value for a free energy parameter.

6 Claims, 11 Drawing Sheets

FIG.3

| MOLECULE | ABBREVIATION |
|---|---|
| AAAAAGCTTTTT<br>TTTTTCGAAAAA | $(AA)_2$ |
| ATATAGCTATAT<br>TATATCGATATA | $(AT)_2$ |
| AAAAAAGCTTTTTT<br>TTTTTTCGAAAAAA | $(AA)_3$ |
| ATATATAGCTATATAT<br>TATATATCGATATATA | $(AT)_3$ |
| AAATATAGCTATATTT<br>TTTATATCGATATAAA | $(AA)(AT)_2$ |
| AAAAAAAAGCTTTTTTTT<br>TTTTTATATCGAAAAAAAA | $(AA)_4$ |
| ATATATATAGCTATATATAT<br>TATATATATCGATATATATA | $(AT)_4$ |

(AT)$_n$ series
- ○ n=2
- □ n=3
- ◇ n=4

(AA)$_n$ series
- ○ n=2
- □ n=3
- ◇ n=4
- ● AA(AT)$_2$

Hexadecamer-Act D Complex (AT)$_n$ AGCT(AT)$_n$
n=2

(AA)$_n$ AGCT(TT)$_n$
n=2

(AT)$_n$ AGCT(AT)$_n$
n=3

(AA)$_n$ AGCT(TT)$_n$
n=3

(AT)$_n$ AGCT(AT)$_n$
n=4

(AA)$_n$ AGCT(TT)$_n$
n=4

AA(AT)$_2$ AGCT(AT)$_2$TT

THERMODYNAMICS, DESIGN, AND USE OF NUCLEIC ACID SEQUENCES

This application is a continuation of application Ser. No. 08/260,200 filed on Jun. 16, 1994 Entitled: "Thermodynamics, Design, and Use of Nucleic Acid Sequences"; now abandoned which is a continuation-in-part of U.S. Ser. No. 08/224,840, filed Apr. 8, 1994, now abandoned, which is a continuation-in-part of U.S. Ser. No. 08/078,759, filed Jun. 17, 1993, now abandoned which are hereby incorporated by reference.

This invention was made with government support under grant numbers GM-39471, GM-42360, and CA-45698 from the National Institutes of Health and grant number DMB-9018782 from the National Science Foundation. Accordingly, the U.S. Government retains certain rights in the invention.

BACKGROUND OF THE INVENTION

This invention relates to the formation and dissolution of double stranded nucleic acid molecules and to the interactions between double and single stranded nucleic acid molecules and nucleic acid-binding ligands. For example it relates to: DNA sequence design and construction including, e.g., methods for determining and preparing DNA sequences with selected reaction attributes, such as binding affinities for their respective ligands; and the use of such sequences in diagnostic or analytical procedures to detect target DNA, e.g., viral DNA.

SUMMARY OF THE INVENTION

In one aspect, the invention features, a method of providing the sequence of a single stranded nucleic acid molecule, which, when hybridized to a complementary single stranded molecule, results in a double stranded (duplex) structure having a preselected value for a free energy parameter, e.g., a preselected $T_m$ or a preselected affinity for a nucleic acid binding ligand.

The method includes:

(1) determining the value of a free energy-parameter of a duplex formed by the hybridization of a test single stranded nucleic acid molecule to a complementary sequence;

(2) comparing the determined value with a reference value for a free energy parameter; and (3) if the determined value exhibits a preselected relationship with the reference value, adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand nucleic acid molecule with a free energy parameter value having the preselected relationship with the reference value is found, and adopting all or part of that test single stranded nucleic acid molecule as all or part of the sequence of the single stranded nucleic acid molecule, thereby providing a single stranded nucleic acid sequence which can form a duplex having a preselected value for a free energy parameter.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

The method provides nucleic acid molecules with defined values for a free energy parameter. Since the value for the parameter is related to a number of important properties, e.g., ligand binding, melting temperature, affinity for a target sequence, resistance of a duplex to perturbation, the method allows for the provision of nucleic acid molecules tailored to specific applications. E.g., as is discussed herein, it allows the production of nucleic acid molecules with a defined affinity for a ligand which binds to the DNA and regulates, e.g., promotes, the expression of a protein encoded by the nucleic acid.

In another aspect, the invention features a method for providing a flanking nucleic acid sequence which is useful as a flanking sequence to a site, e.g., a binding site for a ligand and, e.g., which modulates a free energy parameter of the site, e.g., the $T_m$, of a site or the affinity of a binding site for the ligand. The flanking nucleic acid sequence is such that when incorporated into a single stranded nucleic acid encoding the site (e.g., as a sequence which flanks a binding site), and the resulting single stranded molecule hybridized to a complementary sequence, a duplex having a preselected value for a free energy parameter is formed. E.g., a duplex having a preselected $T_m$ is formed, the duplex having a site which has a $T_m$ of a preselected value, a ligand binding constant of a preselected value, or a preselected value for the composite rate of reaction of the ligand.

The method includes:

(1) determining the value of a free energy-parameter of a duplex formed by the hybridization of a test single stranded nucleic acid molecule to a complementary sequence;

(2) comparing the determined value with a reference value for a free energy parameter; and (3) if the determined value exhibits a preselected relationship with the reference value, adopting all or part of the test single stranded nucleic acid molecule as all or part of the flanking sequence, but if the determined value does not exhibit a preselected relationship with the reference value, repeating steps (1) and (2) on one or more subsequent test single stranded nucleic acid molecules until a test single stranded nucleic acid molecule with a free energy parameter value having the preselected relationship with the reference value is found, and adopting all or part of that test single stranded nucleic acid molecule as all or part of the sequence of the flanking sequence, thereby providing a single stranded nucleic acid sequence which can form a duplex having a preselected value for a free energy parameter.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

The method allows for the alteration of a property of a site, e.g., ligand binding, melting temperature, affinity for a target sequence, resistance or suseptability of a duplex to perturbation, without affecting the sequence of the site itself. Thus, e.g., the binding affinity of a ligand having an extremely specific binding site sequence requirement can be modulated without changing the sequence of the site by providing the appropriate flanking sequence.

In another aspect, the invention features a method of optimizing the binding of a ligand to a nucleic acid, by providing an optimized binding site. The method includes:

(1) providing a test nucleic acid sequence which includes or flanks the binding site;

(2) permuting the sequence of the test nucleic acid sequence;

(3) determining a value for a free energy-related parameter for the permuted test molecule and if the determined value optimizes the free energy parameter (e.g., if the value is decreased in the case where decreased binding is desired, or if the value is increased in the case where increased binding is desired) using all or part of the permuted test molecule as all or part of a nucleic acid sequence which includes or flanks the binding site.

In preferred embodiments, steps (1), (2), and (3), are performed to provide a first sequence having a preselected value for a free energy parameter, and the cycle of steps (1), (2), and (3), repeated using the first sequence as a starting point to provide a second single stranded molecule (which is a permutation of the first) a duplex having a preselected value for a free-energy parameter. The second sequence can have a value for a free-energy parameter which is greater than, or less than, the value of the parameter for the first sequence.

In preferred embodiments the permuted sequence is subjected to one or more subsequent cycles of steps (2) and (3) above, to further optimize the site. The permutations in subsequent cycles can be at the same base pair as in the first cycle or at different base pairs. Subsequent cycles can be repeated, e.g., until no further optimization is gained or until a predetermined number of cycles has been performed.

In preferred embodiments: the site controls, e.g., at the transcriptional level, the expression of an RNA or a peptide; the binding site is a binding site for a nucleic acid binding protein, e.g., a sequence-specific nucleic acid binding protein, or a protein which binds in a sequence non-specific manner; the site is in or near an element which regulates transcription (wherein near means sufficiently close for binding to affect control of a sequence under the control of the element); the site is near or in an enhancer; the site is in or near a promoter; the site is the site of binding of a ligand which affects recombination, viral entry into a nucleic acid, or replication of a nucleic acid.

The invention allows for the construction of useful binding sites, e.g., promoter or other control sequences sites which are engineered to express a product at a defined level, or sites which are engineered to support amplification at a defined level.

In another aspect, the invention features, a method for providing a set of nucleic acid primers. The set of primers includes: a first single stranded primer which when hybridized to a complementary single stranded molecule, results in a first double stranded (duplex) structure having a first value for a free energy parameter, e.g., a preselected $T_m$ or a preselected affinity for a nucleic acid binding ligand, e.g., a DNA polymerase, e.g., Taq polymerase, or which supports the amplification of a product from a region of the first duplex at a first rate of amplification; and a second single stranded primer which when hybridized to a complementary single stranded molecule, results in a second double stranded (duplex) structure having a second value for a free energy parameter, e.g., a preselected $T_m$ or a preselected affinity for a nucleic acid binding ligand, e.g., a DNA polymerase, e.g., Taq polymerase, or which supports the amplification of a product from a region of the second duplex at a second rate of amplification.

The method includes:

(1) determining the value of a free energy-parameter of a duplex formed by the hybridization of a test single stranded nucleic acid molecule to a first (complementary) target sequence;

(2) comparing that value with a reference value for a free energy parameter; and (3) if the determined value exhibits a preselected relationship with a reference value adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand nucleic acid molecule with a free energy parameter value having the preselected relationship with the reference value is found, and adopting all or part of that single stranded test nucleic acid molecule as all or part of the sequence of a first primer, thus providing a first primer having a preselected relationship with a reference value for the free energy, e.g., having a preselected relationship with the free energy parameter value for the second primer of the set.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complementary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

In preferred embodiments the method further includes providing a second primer by:

(1) determining the value of a free energy-parameter of a duplex formed by the hybridization of a test single stranded nucleic acid molecule to a second (complementary) target sequence;

(2) comparing that value with a reference value for a free energy parameter; and (3) if the determined value exhibits a preselected relationship with a reference value adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand with a free energy parameter value having the preselected relationship with the reference value is found, and adopting all or part of that single stranded test nucleic acid molecule as all or part of the sequence of a second primer, thus providing a second primer having a preselected relationship with a reference value for the free energy parameter, e.g., the value of the free energy parameter of the first primer.

Matched primers can be used e.g., to amplify two or more separate target sequences at approximately the same rate, providing for multiplexed amplification reactions, e.g., multiplexed PCR reactions. In many cases, a relatively small difference in amplification rate at a first site and the amplification rate at a second site will, after a relatively small number of cycles of amplification, result in a relatively great preponderance of the products generated from the site with the higher amplification rate. The more highly amplified site produces a signal which "swamps" the signal from the less highly amplified site. By balancing the amplification rates, the signal from two (or more) amplified sites can be more easily detected in a single reaction mixture. The method allows relatively easy, convenient, and reliable detection of more than one target sequence in a sample. E.g., a single sample can be tested, simultaneously, for the presence of two or more microbial contaminants.

Matched primers of the invention can be used to test a single sample of a biological fluid, e.g., blood, serum, plasma, or urine, for the presence of multiple target sequences in a single reaction, e.g., to detect the presence of a plurality of disease causing organisms in a single reaction. In particular, the primers are useful for detecting organisms which contribute to septecemia, e.g., a bacterium, e.g., a gram negative bacterium, an anerobic infectious agent, a streptococcal agent, a staphlyloccocal agent, a pneumococcal agent, *E. coli*, or psuedomonas.

Specification of the Tm for two oligonucleotides primers used in a reaction is all that is required to specify the difference in binding constant of the polymerase for the two sites and the rates of amplicon formation. This is of particular value in multiplex PCR reactions. As long as the Tm of two primers is held at the essentially the same value (by appropriate primer design) the amplicons will be produced at essentially the same rate. This is because the rate of production is dependent on binding and enzymatic extension steps of the polymerase during the cycling reaction.

One of the most vexing problems in PCR-based detections is the generation of false positives from sample contamination. If a panel of PCR primers with known or matched amplicon formation rates is used in a reaction, then a false positive can be identified (because of the low to insignificant (depending on how many primer pairs are simultaneously employed) probability that a sample will be contaminated with several different amplicons simultaneously). Further, since the rates of amplicon formation are known, the relative product concentrations are also known and alteration of the product ratios serves as an independent indication of contamination.

Thus, the invention also provides a method of determining if an amplified signal, e.g., the amplified signal in a PCR reaction, is a false positive, by comparing the rate of amplification for the signal with the rates for one or more signals generated by primers with known or matched rates. A rate of amplification which differs from that of the added primers is indicative that the signal is a false positive.

The invention also includes primers or other sequences or molecules made by the methods of the invention.

In another aspect, the invention features, a set of primers, or a reaction mixture, including:

a first single stranded primer which when hybridized to a complementary single stranded molecule, results in a first double stranded (duplex) structure having a first value for a free energy parameter, e.g., a preselected $T_m$ or a preselected affinity for a nucleic acid binding ligand, e.g., a DNA polymerase, e.g., Taq polymerase, or which supports the amplification of a product from a region of the first duplex at a first rate of amplification; and a second single stranded primer which when hybridized to a complementary single stranded molecule, results in a second double stranded (duplex) structure having a second is value for a free energy parameter, e.g., a preselected $T_m$ or a preselected affinity for a nucleic acid binding ligand, e.g., a DNA polymerase, e.g., Taq polymerase, or which supports the amplification of a product from a region of the second duplex at a second rate of amplification, provided that: the free energy parameter value or the amplification rate of the first primer is approximately equal to the free energy parameter value or the amplification rate of the second primer; the free energy parameter value or the amplification rate of the first primer is sufficiently similar to that of the second primer such that detection of both amplification products in a single reaction, e.g., in a single PCR reaction is possible; the first and second free energy parameter values and thus the first and second rates of amplification, are approximately equal; or the values for the first and second free energy parameter, and thus the first and second amplification rates, are sufficiently similar such that they allow detection of both amplification products after q, wherein q is an integer between 1 and 100, inclusive, cycles of amplification of one of the amplified regions, e.g., the region with the highest or the region with the lowest rate of amplification.

Methods of the invention use thermochemical data to evaluate duplex stability of nucleic acid sequences including or flanking a binding site or a site of reaction. A direct correlation derived therefrom between duplex stability and either relative binding constant or composite reaction rate provides a rule for determining at least one DNA sequence that can be employed as a flanking sequence to a DNA binding site for the ligand with resulting relative increase, decrease, or equality in binding constant of the ligand for its binding site or in composite reaction rate for reaction between the ligand and the DNA sequence. These methods allow adjustment of reaction or binding parameters of a DNA sequence towards a ligand, including but not limited to a restriction enzyme, ligase, or polymerase.

Methods of the invention provide for the development of highly accurate protocols using DNA amplification strategies (such as those based on the polymerase chain reaction) for the diagnosis of disease states caused by viral DNA and difficult to determine with high certainty by any known method in the art, in part because of significant analytical difficulties in reliably detecting the identity of the related DNA sequences at ultralow levels. An important example of a DNA disease virus is human immunodeficiency virus, wherein false positives can have serious psychological and social consequences.

In another aspect, the invention features a method of predicting the relative susceptibility of a site on a nucleic acid duplex to perturbation. The method includes:

determining the value of a free energy-parameter of a duplex which includes or flanks the site, the value for the free energy parameter being predictive of the susceptibility of the site to perturbation.

In preferred embodiments: the value for a free energy parameter is determined by, beginning at a first base pair of the duplex, determining a value for the free-energy parameter of n base pairs in a window (a window is a number of bases, preferably adjacent bases), where n is any integer between 1 and 1,000, inclusive, (preferably n is less than 10, 20, 30, 40, 50, 100, 200, 300, 400, 500, or 1,000) moving the window to another base pair, and determining a value for the free energy parameter of the next window, and repeating the process for some or all of the remaining base pairs of the duplex, preferably, the windows are determined in the linear order in which they appear on the duplex; the free energy $\Delta G_D^\circ$ of duplex melting for the duplex which includes or flanks the site is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation.

In preferred embodiments, the method further includes, providing a nucleic acid sample (which includes the site) from a subject, and determining (e.g., by determining the value of a free energy parameter for the duplex) if there is a mutation (e.g., a mutation which alters the value of a free energy parameter at the site) in the site, a mutation at the site being indicative of risk of a disorder, e.g., a neoplastic disorder. The method also allows identification of mutations which are likely to alter the reactivity of the duplex (e.g., mutations which would render the duplex more likely to bind a ligand, e.g., a ligand which regulates the expression of a protein).

The invention allows the discovery of sites which are susceptible to perturbation, e.g., to mutation. This method can be used to identify sites which are susceptible to mutation, and can thus identify sites in a gene which may be useful in determining if an individual is at risk for a disorder related to a lesion in the gene.

In another aspect, the invention features a method of constructing a map of the relative susceptibility to perturbation, e.g., mutation, of a plurality of sites in a region of a nucleic acid duplex. The method includes:

(1) determining the value of a free energy-parameter of a first site in the region, the free energy parameter being correlated to susceptibility to perturbation; and (2) determining the value of a free energy-parameter for each remaining site in the region, thereby providing a map of the free energy-parameter values for the sites in the region of the duplex, the value of the free energy parameter being correlated with the susceptibility of a site to perturbation.

A map of the relative susceptibilities to perturbation sensitive regions is useful for detecting gene coding regions (which are relatively stable regions), detecting gene control regions (which tend to be more stable than even coding regions), or to detect sites of preferential reactivity.

Methods described herein allow direct and explicit determination of the site specific reactivity of a ligand, e.g., an enzyme, which interacts with or effects changes upon a nucleic acid, e.g, a DNA. Methods of the invention rely, in part, on the refinement of thermodynamic values for duplex stability. It is shown herein that if one can explicitly determine the reactivity of different DNA sequences with the same ligand, then differences observed are due solely to the difference in DNA sequence.

Methods of the invention are concerned with the general process $$E + D \underset{k_{-1}}{\overset{k_1}{\rightleftarrows}} ED \overset{k_2}{\rightarrow} E + P \qquad (a)$$

where E is any enzyme, D is a given DNA sequence, ED is the complex between the enzyme and DNA, and P is the product(s) produced the action of E on D.

The overall rate of this reaction, $k_c$, can be expressed as $$k_c = K_1 k_2 [1 + k_2/k_{-1}]^{-1} \qquad (b)$$

where $k_c$=the composite second order rate constant for the reaction (two reactants and one product), $k_1$=forward rate constant for the first step, $k_{-1}$=reverse rate constant for the first step, $k_2$=the rate constant for catalysis, and $K_1=k_1/k_{-1}$ the equilibrium constant for forming the bound complex (e.g., $K_1 = e^{-\Delta G_1^{0}/RT}$.

From equation (b) (rewriting the expression in terms of energies instead of rates and equilibrium expressions)

$$-RT\ln k_c = -RT\ln K_1 - RT\ln k_2 + RT\ln[1 + k_2/k_{-1}] \qquad (c)$$

$$\Delta G_c^{\ddagger+0} = \Delta G_1^0 + \Delta G_2^{\ddagger+0} - RT\ln A_2 + RT\ln[1 + k_2/k_1] \qquad (d)$$

It is an empirical fact that, $$\Delta G_c^{\ddagger+0} = \kappa(\Delta G_D^0) \qquad (e)$$

where $\Delta G_D^0$=the free energy of melting the duplex, D, from equation (a) and $\kappa$=a constant that relates the composite activation free energy to the free energy of melting the duplex.

It follows that even if all that is known is the composite rate for two different DNA sequences, $k_c$ and $k_c'$, respectively and (independently) the melting free energies of the two duplexes, $\kappa$, may be determined directly viz (substituting into (e) and subtracting)

$$\kappa = RT\ln[k_c'/k_c]/(\Delta G_D^0 - \Delta G_D^{0\prime}) \qquad (f)$$

This is the explicit relationship between relative rates at which a nucleic acid, e.g., DNA, substrate for the same ligand react with respect to the free energy of the unbound substrate. This relationship will hold for all sequences using any given ligand. Therefore, if one knows the relative stabilities (e.g., Tm's) of DNA sequences the relative reaction rates may be explicitly specified. $\kappa$ is discussed in more detail below, see infra.

Throughout this application the convention for describing free energy is: increasing $\Delta G_D^\circ$ decreases the stability of the duplex and increases reactivity, e.g., ligand binding; and, decreasing $\Delta G_D°$ increases the stability of the duplex and decreases reactivity of the duplex.

The following Detailed Description is set forth to aid in an understanding of the invention, and are not intended, and should not be construed, to limit in any way the invention set forth in the claims which follow thereafter.

DETAILED DESCRIPTION

(a) Free-energy profiles calculated using the sets of n—n interactions in columns A, B and C of Table 1. The uppermost curve was calculated from the values in column B. The next upper curve was calculated from the values in column C. The bottom curve is the energy profile calculated using the values in column A. Beginning at the first bp of the sequence, the free-energy of 30 bps in a window was calculated and plotted as a point. The window was then moved one bp and the energy of the next 30 bp window was calculated. Repeating the process to the end of the sequence results in the plots in (a).

(b) Difference curves of the plots in (a). Three plots of the normalized differences calculated as described in the text are shown in arbitrary units. The top curve is the difference profile for the differences between the uppermost curve and lowest curve in (a). The middle curve is the difference between the middle and lowest energy profiles in (a). The lowest difference plot corresponds to the difference between the two upper curves in (a).

FIG. 2 is a graph of free energy profiles calculated for 120 base pair windows of the 1635 bp HinfI restriction fragment sequence from pBR322.

(a) Exactly as in (a) of FIG. 1 except the energy profiles were calculated using a 120 bp window.

(b) Exactly as in (b) of FIG. 1 except these energy difference profiles were calculated from the energy profiles in (a) determined at a window of 120 bps.

FIG. 3 is a list of the sequences of the seven duplexes prepared and examined in the studies described in the text are shown. Abbreviations for the molecules are given at the right and used for reference throughout the text ((AA)$_2$ (SEQ ID NO: 5); (AT)$_2$ (SEQ ID NO: 4); (AA)$_3$ (SEQ ID NO: 3); (AT)$_3$ (SEQ ID NO: 2); (AA)(AT)$_2$ (SEQ ID NO: 6); (AA)$_4$ (SEQ ID NO: 8); and (AT)$_4$ (SEQ ID NO: 7)).

Figure 4A:
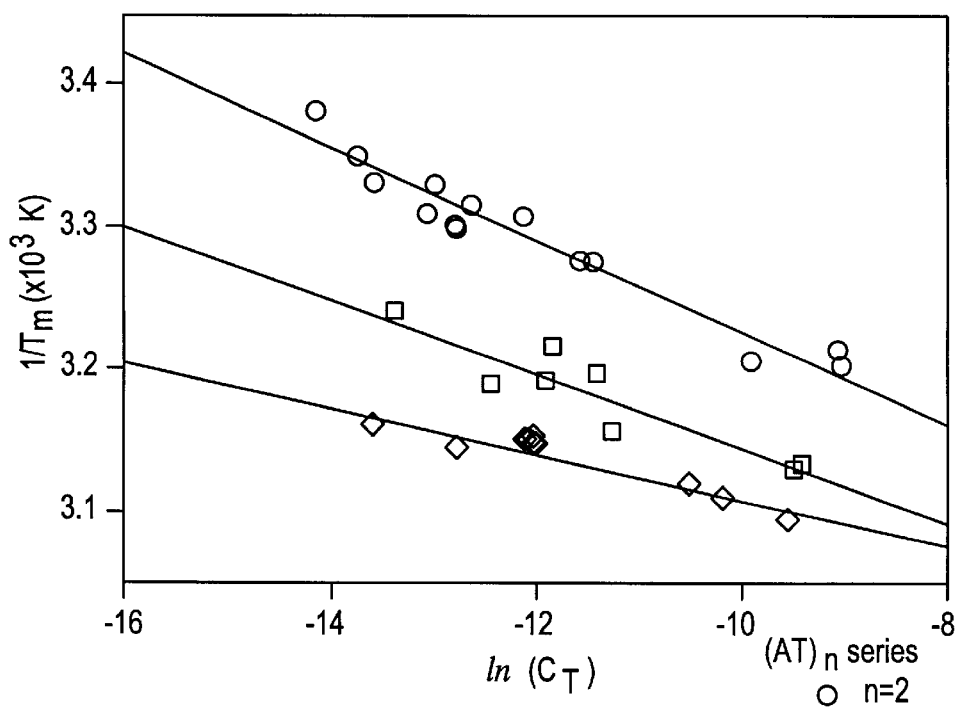
Figure 4B:
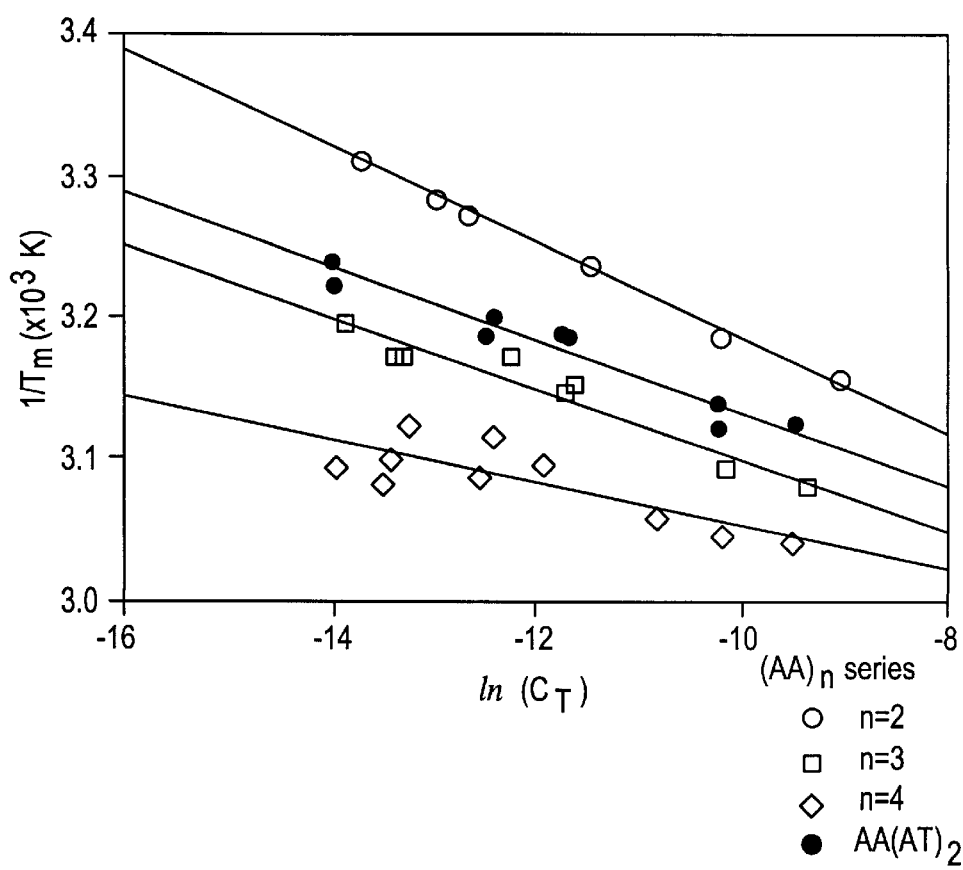

FIG. 4 is a graph of Van't Hoff plots obtained from melting curves of the seven DNA molecules. Transition temperatures were obtained from melting curves of the molecules in FIG. 3 conducted in 115 mM Na$^+$ as a function of total strand concentration, $C_T$, and plotted as shown. The van't Hoff plots for the AT series, (AT)$_2$ (SEQ ID NO: 3), (AT)$_3$ (SEQ ID NO: 1), (AT)$_4$ (SEQ ID NO: 6) are shown in the upper plot (a). Plots for the AA series, (AA)$_2$ (SEQ ID NO: 4), (AA)$_3$ (SEQ ID NO: 2), (AA)$_4$ (SEQ ID NO: 7) and AA(AT)$_2$ (SEQ ID NO: 5) are shown in the lower plot (b). From the slope of each of these plots of $1/T_m$ versus $\ln C_T$ the melting transition enthalpy, $\Delta H$, of each DNA in FIG. 3 was evaluated. The van't Hoff analysis assumes the melting transitions occur in a two-state manner.

Figure 5:
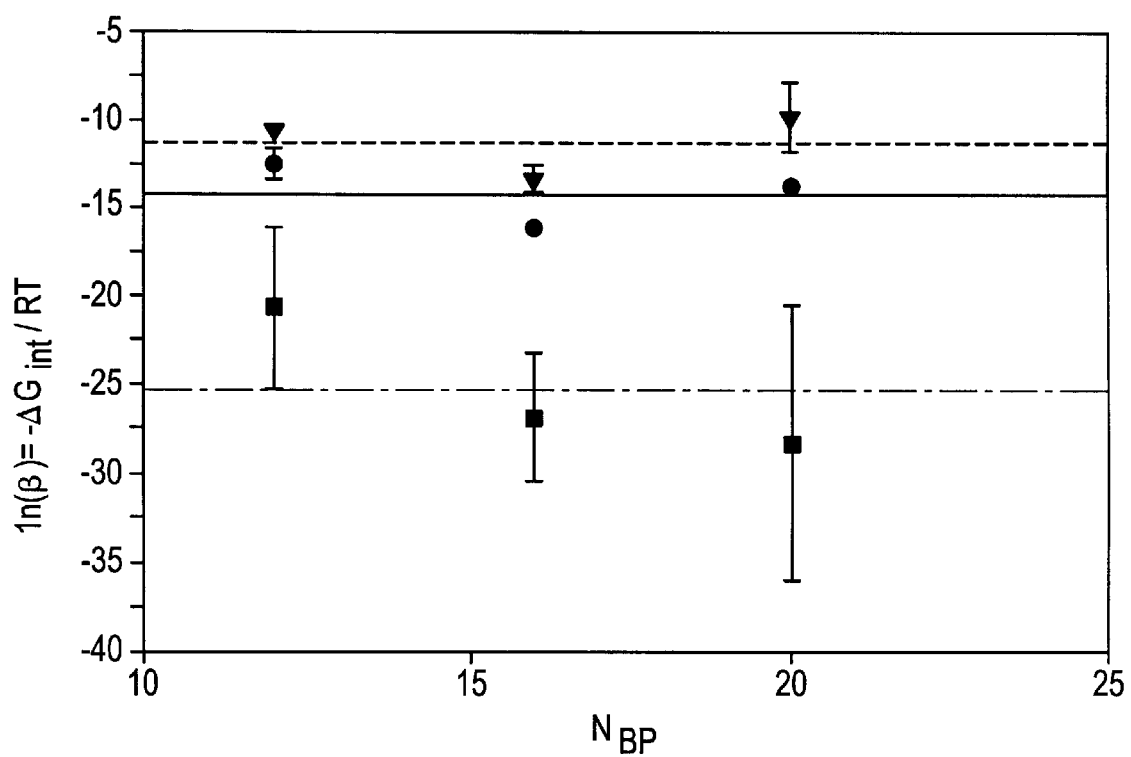

FIG. 5 is a plot of the helix initiation parameter versus duplex length. The natural log of the helix initiation factor, $\beta$, is plotted versus the number of bps in the duplex. Three sets of data and linear fits to them are shown. The uppermost set (triangles, dashed line) was determined from experiments in 75 mM Na$^+$, and was constructed from the average values given in column B of Table 5. The middle set (circles, solid line) was determined from experiments in 115 mM Na$^+$, and was constructed from the average values in column C of Table 5. The lower-most curve (squares, broken line) was determined from experiments in 1.0 M Na$^+$, and was constructed from the average values in column A of Table 5. The error bars indicate deviations from the averages for DNAs of different lengths. In the cases of the upper-most and lower-most plots the larger deviations may be due to differences in solvent environments for the calculated free-energies and experiments where the free-energies of the DNAs were actually determined. These plots show the free energy of helix initiation, $\Delta G_{init}$, is essentially constant for these DNAs ranging from 12 to 20 bps in length.

Figure 6B:
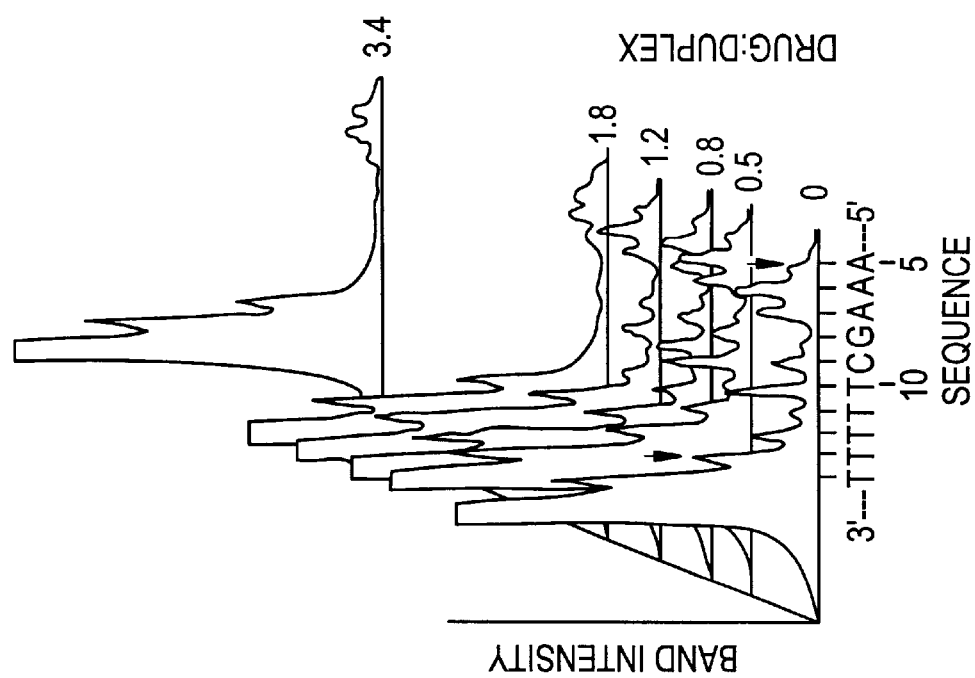
Figure 6A:
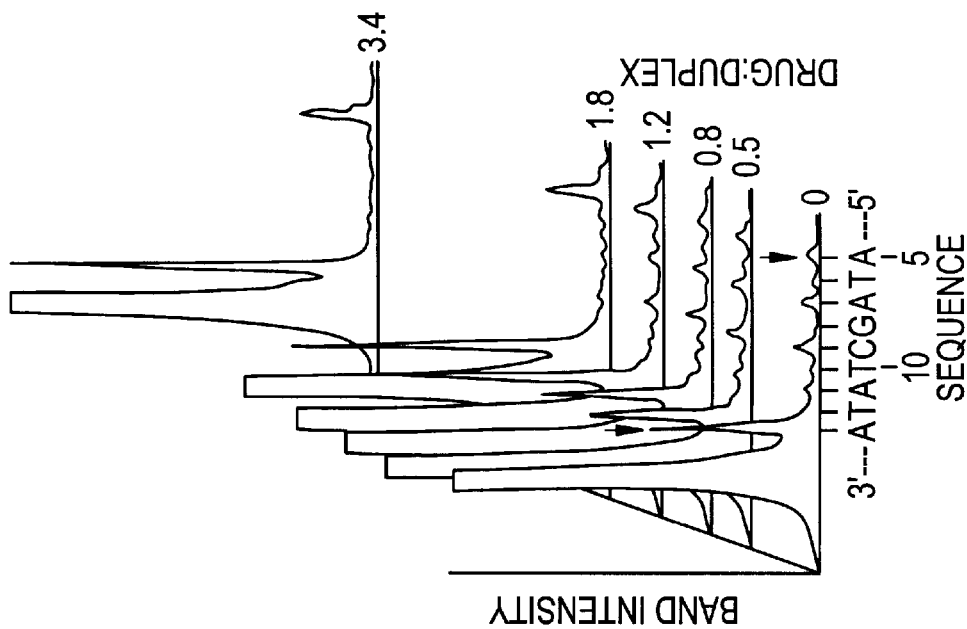

FIG. 6 is a representation of DNAse I footprints of Actinomycin D. Results of the DNAse I footprinting experiments of (AT)$_3$ (SEQ ID NO: 1) (a) and (AA)3 (SEQ ID NO: 2) (b) in FIG. 3 bound by increasing amounts of Actinomycin D at the central AGCT site of these sequences are shown. Base pair positions are shown on the horizontal axis. Intensities determined from bands after electrophoretic analysis of partial cleavage products of DNAse I are indicated on the vertical axis. Drug:duplex stoichiometry increases going into the Figure. Band intensities corresponding to cleavage enhancements away from the drug binding site are clearly seen. As indicated by the arrows on the plot for the (AT)$_3$ (SEQ ID NO: 1) sequence (a), with increases in drug:duplex stoichiometry, significant DNAse I enhancements occur at positions three bps to the 5' side and 5 bp to the 3' side of the drug binding site. In contrast for the (AA)$_3$ (SEQ ID NO: 2) sequence (b) no significant enhancements are observed at comparable locations (indicated by the arrows). These observations are interpreted to indicate that the bound drug transmits effects through the flanking (AT)$_3$ (SEQ ID NO: 1) sequences that alter the DNAse I cleavage pattern. Such effects are apparently not transmitted through (AA)$_3$ (SEQ ID NO: 2) flanking sequences.

Figure 7:
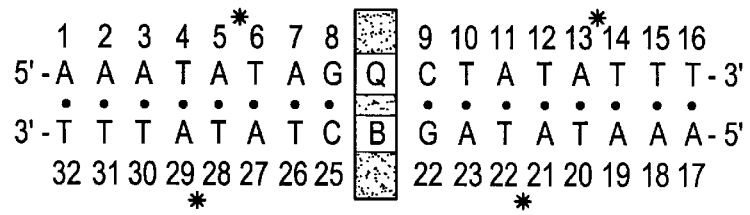
Figure 7A:
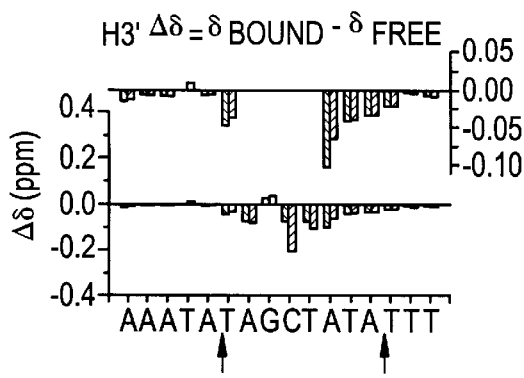
Figure 7C:
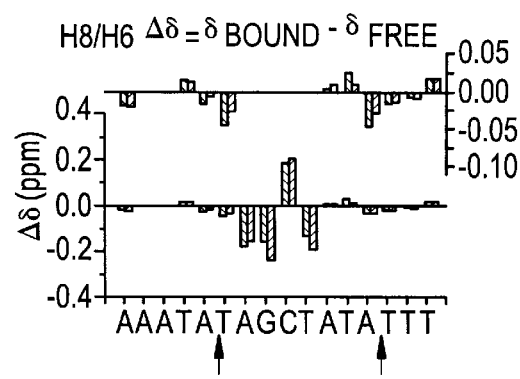
Figure 7B:
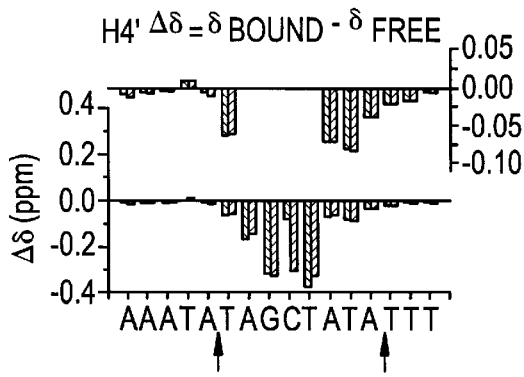
Figure 7D:
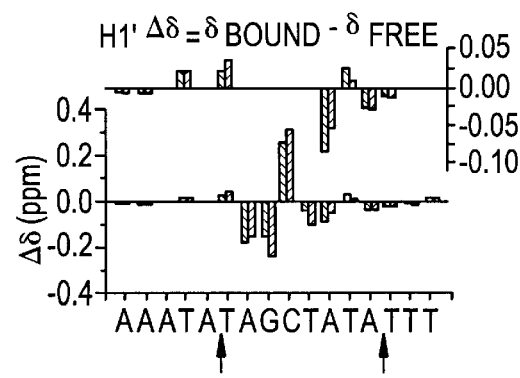
Figure 8A:
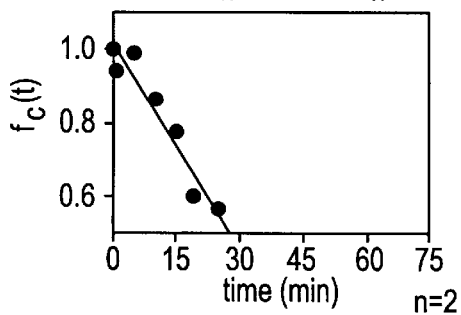
Figure 8E:
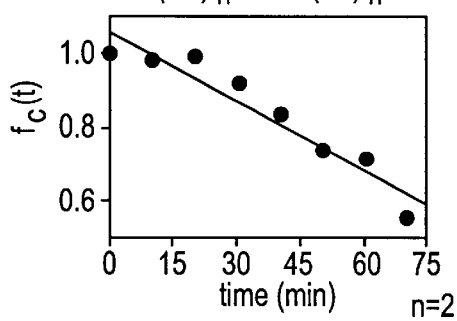
Figure 8B:
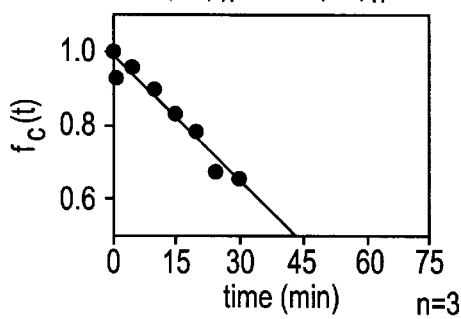
Figure 8F:
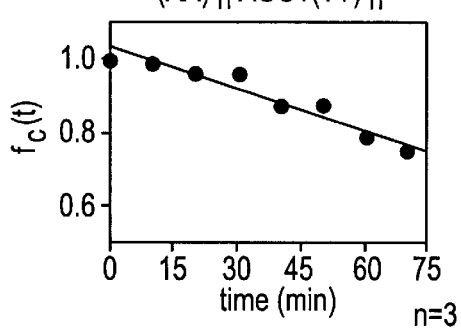
Figure 8C:
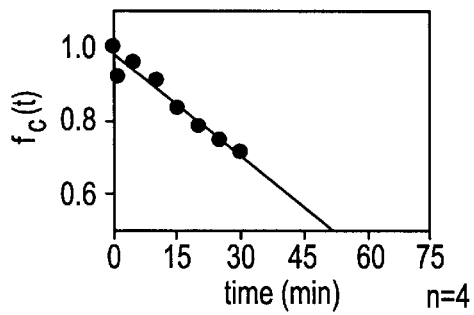
Figure 8G:
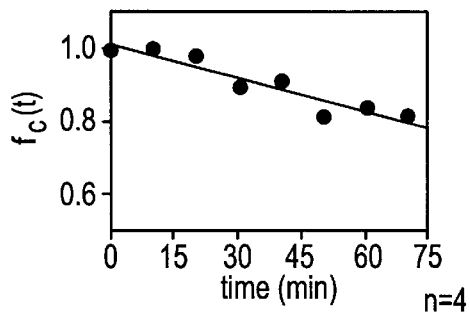
Figure 8D:
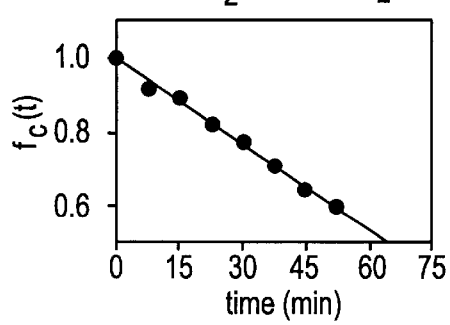

FIG. 7 is a depiction of proton chemical shift changes in a sixteen base pair duplex DNA bound by Actinomycin D. The 16 bp sequence AA(AT)$_2$ (SEQ ID NO: 5) is shown at the top. The quinoid (Q) and benzenoid (B) ring positions of actinomycin D are indicated. The asterisks indicate sites of DNAse I cleavage enhancements induced by bound drug determined in independent experiments. Changes in chemical shift, $\Delta\delta$(ppm) of the H3' (a), H4' (b), H8/H6 (c) and H1' (d) protons determined from the nuclear magnetic resonance spectra before and after the drug was bound ($\Delta\delta = \delta_{BOUND} - \delta^{FREE}$) are represented. In all cases there are clear differences at bp positions significantly removed from the central AGCT sequence where the drug binds. Consistent with DNAse I measurements significant differences in chemical shift are found at sites up to and beyond five bps away. These data provide independent structural evidence that actinomycin D bound to the central sequence of a short DNA can induce effects some distance away which lead to DNAse I cleavage enhancements.

FIG. 8 is a depiction of measurements of the rates of first strand cleavage by Alu I restriction enzyme for seven DNA molecules. The fraction of first strand cleaved product by Alu I as a function of time, $f_c(t)$, is plotted versus time for each of the DNAs shown in FIG. 3. The data were collected at least two times on different labeled DNA samples under identical conditions. A summary of the results for all molecules is shown. Rate plots for the (AT) series molecules, (AT)₂ (SEQ ID NO: 3), (AT)₃ (SEQ ID NO: 1), and (AT)₄ (SEQ ID NO: 6) are shown on the left. Rate plots for the (AA) series molecules, (AA)₂ (SEQ ID NO: 4), (AA)₃ (SEQ ID NO: 2), and (AA)₄ (SEQ ID NO: 7) are shown on the right. The rate plot for the hybrid molecule, AA(AT)₂ (SEQ ID NO: 5) is shown in the middle. Slopes of these plots decrease with increasing length and are greater for molecules from the (AT) series than for molecules from the (AA) series of the same size. From these slopes the observed first order rate constants for first strand cleavage were obtained. Results are summarized in Table 6.

Figure 9:
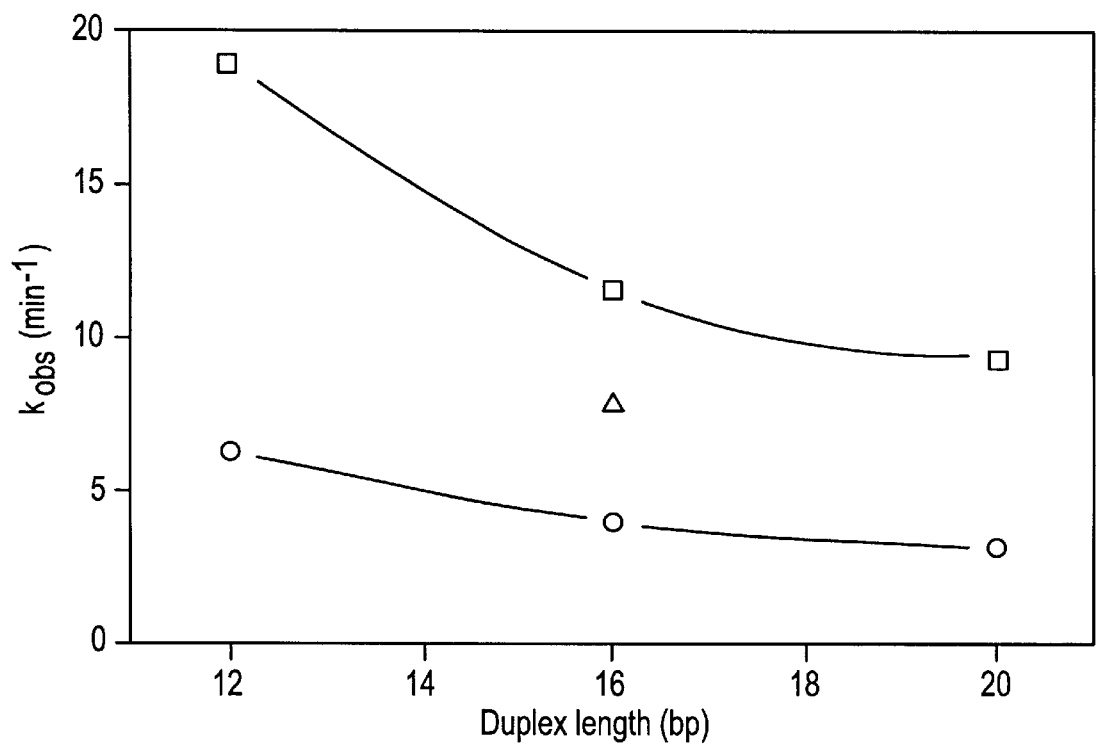

FIG. 9 is a plot of the observed rate constants for first strand cleavage of the seven DNA molecules versus duplex length. The observed rate constants for first strand cleavage by Alu I, $k_{obs}$, of the seven DNA molecules in FIG. 3, determined from the data in FIG. 8 and summarized in Table 6, are plotted versus duplex length. A clear increase in $k_{obs}$ is seen with decreasing duplex length. The 16 bp molecule, with neither purely (AT) or purely (AA) flanking sequences, AA(AT)₂ (SEQ ID NO: 5), has a cleavage rate intermediate between the 16 bp molecules with (AT) and (AA) flanking sequences.

Figure 10:
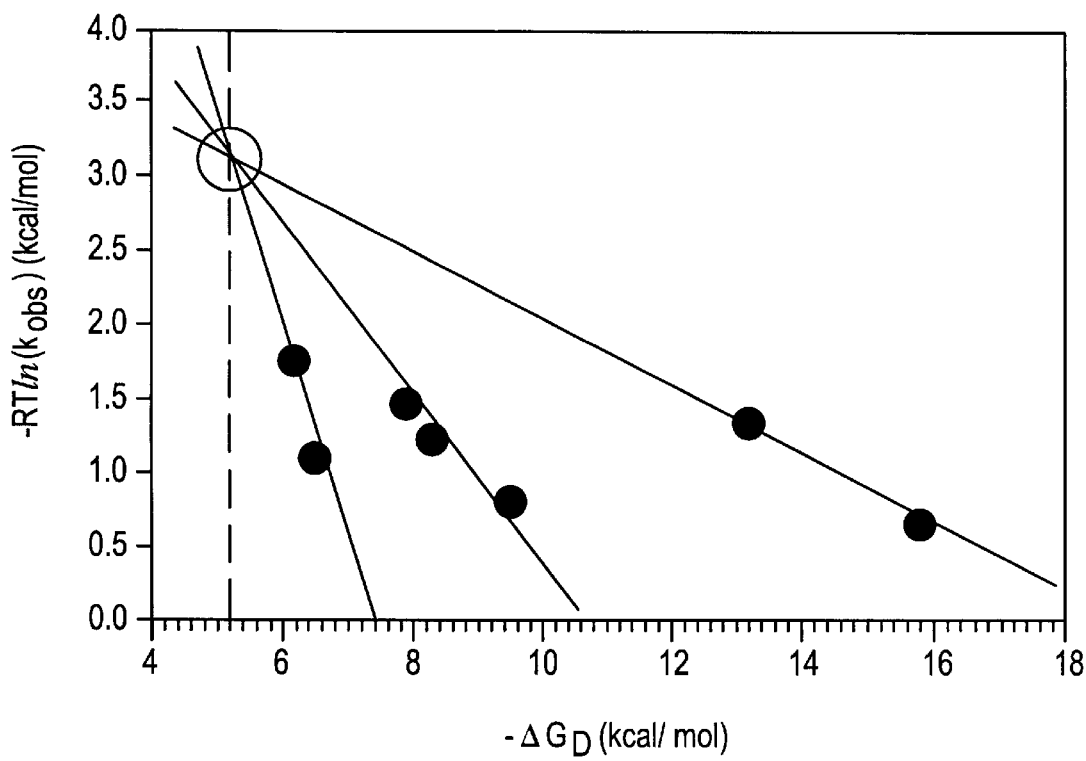

FIG. 10 is a plot of the observed rate constants for first strand cleavage of the seven DNA molecules versus their free-energies of melting. The quantity $-RT\ln k_{obs}$ determined from Table 6 is plotted versus the free-energy of duplex melting, $-\Delta G_D$, for the seven DNAs in FIG. 3. Experimentally determined values are summarized is Table 4. This plot reveals that melting free-energy is linearly proportional to $-RT\ln k_{obs}$, and this proportionality depends quite dramatically on duplex length. Lines sketched through the data extrapolate to a single intersection point (circled) suggesting the observed differences in cleavage behavior are due to free-energies of only the flanking sequences. In fact, the intersection point (dashed line) corresponds precisely to the calculated melting free-energy (−5.2 kcal/mol) of the central four bp sequence AGCT.

Figure 11:
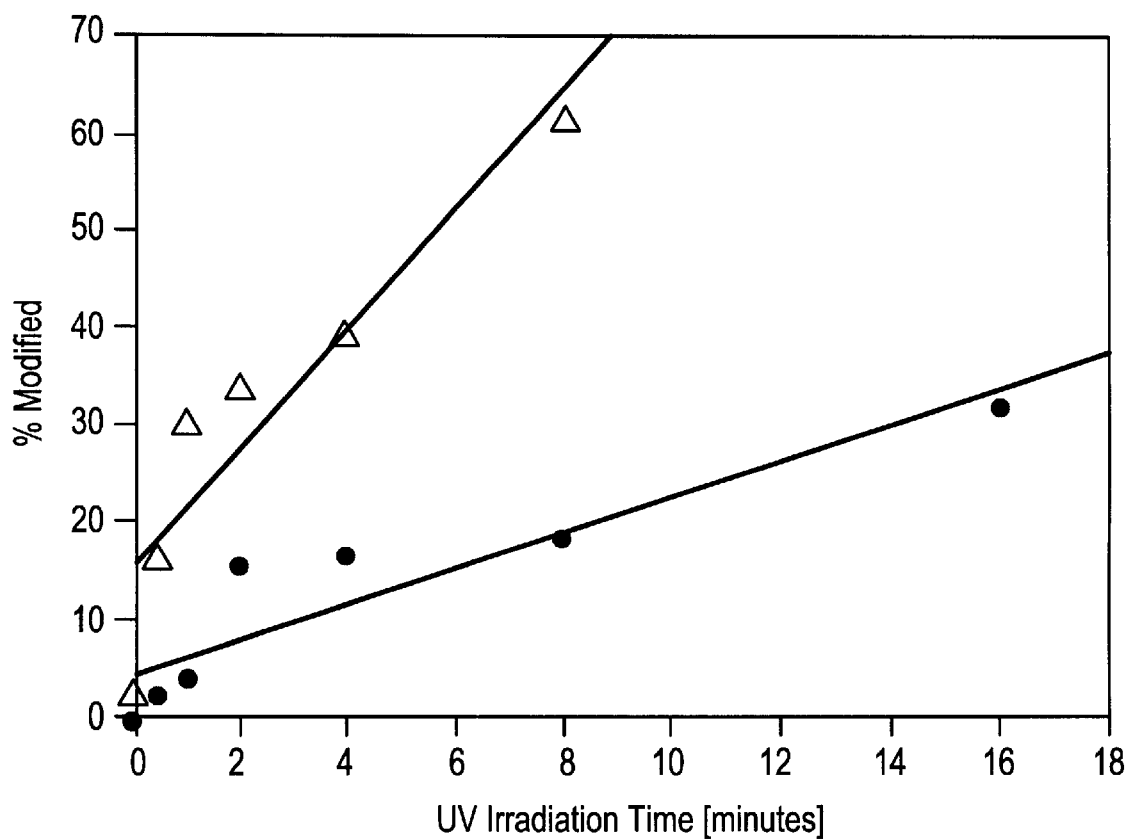

FIG. 11 is a plot of the reactivity of two duplex DNA's with the anti-tumor agent gilvocarcin V. The percent of UV adduct formation (% modified) for the 16 bp DNAs (AA)₃ (SEQ ID NO: 2) (filled circles) and (AT)₃ (SEQ ID NO: 1) (open triangles) versus irradiation time by broad band ultraviolet light ($\lambda$=254 nm, supplied by a handheld lamp with output of approximately 2200 watts/cm²). Clearly, modification occurs at a greater rate for (AT)₃ (SEQ ID NO: 1) than for (AA)₃ (SEQ ID NO: 2). The observed difference in reactivities for these similar DNA sequences with gilvocarcin is analogous to similar observations made for reactivities of these DNAs with other agents as summarized in Table 7.

SEQUENCE DESIGN

In one aspect, the invention features, a method of providing the sequence of a single stranded nucleic acid molecule, which, when hybridized to a complementary single stranded molecule, results in a double stranded (duplex) structure having a preselected value for a free energy parameter, e.g., a preselected $T_m$ or a preselected affinity for a nucleic acid binding ligand.

The method includes:

(1) determining the value of a free energy-parameter of a duplex formed by the hybridization of a test single stranded nucleic acid molecule to a complementary sequence;

(2) comparing the determined value with a reference value for a free energy parameter; and (3) if the determined value exhibits a preselected relationship with the reference value, adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand nucleic acid molecule with a free energy parameter value having the preselected relationship with the reference value is found, and adopting all or part of that test single stranded nucleic acid molecule as all or part of the sequence of the single stranded nucleic acid molecule, thereby providing a single stranded nucleic acid sequence which can form a duplex having a preselected value for a free energy parameter.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

The value of the free-energy parameter can be determined, e.g., empirically, semi-empirically, or by calculation, e.g., by a method described herein, or by any method known to those in the art.

In preferred embodiments: the value for a free energy parameter is determined by, beginning at a first base pair of the duplex, determining a value for the free-energy parameter of n base pairs in a window, where n is any integer between 1 and 1,000, inclusive, (preferably n is less than 10, 20, 30, 40, 50, 100, 200, 300, 400, 500, or 1,000) moving the window to another base pair, and determining a value for the free energy parameter of that window, and repeating the process on some or all of the base pairs of the duplex, preferably, the windows are determined in the linear order in which they appear on the duplex; the free energy $\Delta G_D°$ of duplex melting for the duplex formed by a single stranded sequence is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation: the free energy of melting for a duplex is determined by an equation, e.g., by the equation:

$$\Delta G_{total} = \Sigma_i \Delta G_{i,i+1} + \Delta G_{sym} + \Delta G_{int},$$

wherein $\Delta G_{i,i+1}$ is the free-energy of the nearest-neighbor base pair doublet formed by base pairs i and i+1 that includes both the hydrogen bonding and stacking free-energies included in the doublet. $\Delta G_{sym}$ is a symmetry correction term required if the two single strands have exactly the same sequence. $\Delta G_{int}$ is the free energy of helix initiation.

In other preferred embodiments the method includes: relating the reactivity of a duplex to another free energy parameter, e.g., $T_m$, by the proprtionality constant or function κ, wherein κ can be determined by determining a free energy parameter, e.g. free energies $\Delta G_D°$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$ln(k^{II}/k^{I})=(\kappa/RT)(\Delta G_D^{oI}-\Delta G_D^{oII}),$$

or, if the relative composite relative reaction rates are binding limited, the calculated relative binding constants are determined by means of an equation, e.g., the equation, $$ln(K^{II}/K^{I})=(\kappa/RT)(\Delta G_D^{oI}-\Delta G_D^{oII}),$$

wherein $k^{I}$ and $k^{II}$ are relative composite rate constants of a reaction for any two DNA sequences I and II, respectively, $K^{I}$ and $K^{II}$ are relative binding constants for the ligand to any two DNA sequences I and II, respectively, R is the universal gas constant, T is absolute temperature, κ is a proportionality constant or function, wherein κ is predetermined in accord with the above-recited equations for the ligand and for set sequence length by calculating free energies of melting $\Delta G_D°$ for at least two preselected DNA flanking sequences if κ is a proportionality constant, or at least three if a function, determined in accord with the summing step; a value for κ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D°$ as determined in accord with above-recited equations; and choosing a test single strand nucleic acid providing a binding constant or composite rate of reaction of the ligand with the DNA binding site of preselected value, e.g., a value which is less than, greater than, or about equal to that of a reference value, e.g., that of a reference flanking sequence. (Every ligand has a κ. κ relates the reactivity of a nucleic acid to another free energy parameter, e.g.,$T_m$. κ can be used to relate the reactivity of a nucleic acid to another free energy parameter when the ligand binder is a duplex or a single strand binder, or when the nucleic acid is a single strand or a duplex.)

In another aspect, the invention features a method for providing a flanking nucleic acid sequence which is useful as a flanking sequence to a site, e.g., a binding site for a ligand and, e.g., which modulates a free energy parameter of the site, e.g., the $T_m$ of a site or the affinity of a binding site for the ligand. The flanking nucleic acid sequence is such that when incorporated into a single stranded nucleic acid encoding the site (e.g., as a sequence which flanks a binding site), and the resulting single stranded molecule hybridized to a complementary sequence, a duplex having a preselected value for a free energy parameter is formed. E.g., a duplex having a preselected $T_m$ is formed, the duplex having a site which has a $T_m$ of a preselected value, a ligand binding constant of a preselected value, or a preselected value for the composite rate of reaction of the ligand.

The method includes:

(1) determining the value of a free energy-parameter of a duplex formed by the hybridization of a test single stranded nucleic acid molecule (which, e.g., includes a site and a flanking sequence) to a complementary sequence;

(2) comparing the determined value with a reference value for a free energy parameter; and (3) if the determined value exhibits a preselected relationship with the reference value, adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single stranded nucleic acid molecule with a free energy parameter value having the preselected relationship with the reference value is found, and adopting all or part of that test single stranded nucleic acid molecule as all or part of the sequence of the flanking sequence, thereby providing a single stranded nucleic acid sequence which can form a duplex having a preselected value for a free energy parameter.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

In preferred embodiments, the binding of a ligand to each test sequence or molecule is determined, either empirically, or from calculations from known ligand properties.

The preselected value for the parameter can be can be increased relative to, decreased relative to, or approximately equal to, a reference value conferred on a duplex by a reference single stranded molecule, e.g., by a reference sequence.

In preferred embodiments the site is: a base pair; a plurality of base pairs, e.g., n base pairs wherein p is an integer between 1 and 1,000; the site is less than 10, 20, 30. 40, 50, 100, 200, 400, 500, or 1,000 base pairs in length.

The value of the free-energy parameter can be determined, e.g., empirically, semi-empirically, or by calculation, e.g., by a method described herein, or by any method known to those in the art.

In preferred embodiments the method includes determining the free energy of melting of a duplex formed by the hybridization of a test single stranded nucleic acid molecule to a complementary sequence, and comparing that free energy with a reference value for free energy, e.g., the free energy of melting, $\Delta G_D°$, of a reference sequence. If the determined free energy of melting is, greater than the reference value (e.g., in the case where an increase (relative to the affinity of the ligand for a duplex with the reference value for free energy) in ligand affinity or composite rate is desired), lower than the reference value (e.g., in the case where a decrease (relative to the affinity of the ligand for a duplex with the reference value for free energy) in ligand affinity or composite rate is desired), or approximately equal to the reference value (e.g., in the case where a ligand affinity or composite rate which is approximately equal to the affinity of the ligand for a duplex with the reference value for free energy is desired), using all or part of the test sequence as all or part of the flanking sequence.

In preferred embodiments: the value for a free energy parameter is determined by, beginning at a first base pair of the duplex, determining a value for the free-energy parameter of n base pairs in a window, where n is any integer between 1 and 1,000, inclusive, (preferably n is less than 10, 20, 30, 40, 50, 100, 200, 300, 400, 500, or 1,000) moving the window to another base pair, and determining a value for the free energy parameter of the next window, and repeating the process on some or all of the remaining base pairs of the duplex, preferably, the windows are determined in the linear order in which they appear on the duplex; the free energy $\Delta G_D^\circ$ of duplex melting for the duplex formed by a test single stranded nucleic acid molecule is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation:

$$\Delta G_{total} = \Sigma_i \Delta G_{i,i+1} + \Delta G_{sym} + \Delta G_{int}.$$

In other preferred embodiments the method includes: relating the reactivity of a duplex to another free energy parameter, e.g.,$T_m$, by the proportionality constant or function $\kappa$, wherein $\kappa$ can be determined by determining a free energy parameter, e.g. free energies $\Delta G_D^\circ$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$\ln(k^{II}/k^I) = (\kappa/RT)(\Delta G_D^{oI} - \Delta G_D^{oII}),$$

or, if the relative composite relative reaction rates are binding limited, the calculated relative binding constants are determined by means of an equation, e.g., the equation, $$\ln(K^{II}/K^I) = (\kappa/RT)(\Delta G_D^{oI} - \Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, $\kappa$ is a proportionality constant or function, wherein $\kappa$ is predetermined in accord with the above-recited equations for the ligand and for set sequence length by calculating free energies of melting $\Delta G_D^\circ$ for at least two preselected DNA flanking sequences if $\kappa$ is a proportionality constant, or at least three if a function, determined in accord with the summing step; a value for $\kappa$ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D^\circ$ as determined in accord with above-recited equations; and choosing at least one DNA flanking sequence to serve as a DNA flanking sequence to a DNA binding site for a ligand, the flanking sequence providing a binding constant or composite rate of reaction of the ligand with the DNA binding site of preselected value, e.g., a value which is less than, greater than, or about equal to that of a reference value, e.g., that of a reference flanking sequence. (Every ligand has a $\kappa$. $\kappa$ relates the reactivity of a nucleic acid to another free energy parameter, e.g.,$T_m$. $\kappa$ can be used to relate the reactivity of a nucleic acid to another free energy parameter when the ligand binder is a duplex or a single strand binder, or when the nucleic acid is a single strand or a duplex.)

In another aspect, the invention features a method of optimizing the binding of a ligand to a nucleic acid, by providing an optimized binding site. The method includes:

(1) providing a test nucleic acid sequence which includes or flanks the binding site;

(2) permuting the sequence of the test nucleic acid sequence;

(3) determining a value for a free energy-related parameter for the permuted test molecule and if the determined value optimizes the free energy parameter (e.g., if the value is decreased in the case where decreased binding is desired, or if the value is increased in the case where increased binding is desired) using all or part of the permuted test molecule as all or part of a nucleic acid sequence which includes or flanks the binding site.

In preferred embodiments, steps (1), (2), and (3), are performed to provide a first sequence having a preselected value for a free energy parameter, and the cycle of steps (1), (2), and (3), repeated using the first sequence as a starting point to provide a second single stranded molecule (which is a permutation of the first) a duplex having a preselected value for a free-energy parameter. The second sequence can have a value for a free-energy parameter which is greater than, or less than, the value of the parameter for the first sequence.

In preferred embodiments the permuted sequence is subjected to one or more subsequent cycles of steps (2) and (3) above, to further optimize the site. The permutations in subsequent cycles can be at the same base pair as in the first cycle or at different base pairs. Subsequent cycles can be repeated, e.g., until no further optimization is gained or until a predetermined number of cycles has been performed.

In preferred embodiments: the site controls, e.g., at the transcriptional level, the expression of an RNA or a peptide; the binding site is a binding site for a nucleic acid binding protein, e.g., a sequence-specific nucleic acid binding protein, or a protein which binds in a sequence non-specific manner; the site is in or near an element which regulates transcription (wherein near means sufficiently close for binding to affect control of a sequence under the control of the element); the site is near or in an enhancer; the site is in or near a promoter; the site is the site of binding of a ligand which affects recombination, viral entry into a nucleic acid, or replication of a nucleic acid.

In other preferred embodiments: binding is optimized to increase or decrease the expression of an mRNA or a peptide under the control of the sequence; binding is optimized to coordinate the expression of an mRNA or peptide under control of the sequence with the expression of an mRNA or peptide not under transcriptional control of the sequence.

In other preferred embodiments: the sequence is a eukaryotic sequence; the sequence exerts translational control over a prokaryotic or eukaryotic mRNA encoding sequence; the identity of the ligand is known; the ligand is unknown; the method further includes expressing an mRNA or peptide under the control of the sequence; the method further includes determining the binding site of the ligand, e.g., by mutational or footprint analysis.

In preferred embodiments the site is: a base pair; a plurality of base pairs, e.g., p base pairs wherein n is p is an integer between 1 and 1,000, inclusive; the site is less than 10, 20, 30. 40, 50, 100, 200, 400, 500, or 1,000 base pairs in length.

The value of the free-energy parameter can be determined, e.g., empirically, semi-empirically, or by calculation, e.g., by a method described herein, or by any method known to those in the art.

In preferred embodiments: the value for a free energy parameter is determined by, beginning at a first base pair of the duplex, determining a value for the free-energy parameter of n base pairs in a window, where n is any integer between 1 and 1,000, inclusive, (preferably n is less than 10, 20, 30, 40, 50, 100, 200, 300, 400, 500, or 1,000) moving the window to another base pair, and determining a value for the free energy parameter of the next window, and repeating the process for some or all of the remaining base pairs in the duplex, preferably, the windows are determined in the linear order in which they appear on the duplex; the free energy $\Delta G_D°$ of duplex melting for the duplex formed by a single stranded sequence is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation:

$$\Delta G_{total} = \Sigma_i \Delta G_{i,i+1} + \Delta G_{sym} + \Delta G_{int}.$$

In other preferred embodiments the method includes: relating reactivity of a duplex to another free energy parameter, e.g., $T_m$, by the proportionality constant or function $\kappa$, wherein $\kappa$ can be determined by determining a free energy parameter, e.g. free energies $\Delta G_D°$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$\ln(k^{II}/k^I) = (\kappa/RT)(\Delta G_D^{oI} - \Delta G_D^{oII}),$$

or, if the relative composite relative reaction rates are binding limited, the calculated relative binding constants are determined by means of an equation, e.g., the equation, $$\ln(K^{II}/K^I) = (\kappa/RT)(\Delta G_D^{oI} - \Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, $\kappa$ is a proportionality constant or function, wherein $\kappa$ is predetermined in accord with the above-recited equations for the ligand and for set sequence length by calculating free energies of melting $\Delta G_D°$ for at least two preselected DNA flanking sequences if $\kappa$ is a proportionality constant, or at least three if a function, determined in accord with the summing step; a value for $\kappa$ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D°$ as determined in accord with above-recited equations; and choosing a test molecule to serve as a DNA flanking sequence to a DNA binding site for a ligand, the flanking sequence providing a binding constant or composite rate of reaction of the ligand with the DNA binding site of preselected value, e.g., a value which is less than, greater than, or about equal to that of a reference value, e.g., that of a reference flanking sequence. (Every ligand has a $\kappa$. $\kappa$ relates the reactivity of a nucleic acid to another free energy parameter, e.g., $T_m$. $\kappa$ can be used to relate the reactivity of a nucleic acid to another free energy parameter when the ligand binder is a duplex or a single strand binder, or when the nucleic acid is a single strand or a duplex.)

In another aspect, the invention features, a method for providing a set of nucleic acid primers. The set of primers includes: a first single stranded primer which when hybridized to a complementary single stranded molecule, results in a first double stranded (duplex) structure having a first value for a free energy parameter, e.g., a preselected $T_m$ or a preselected affinity for a nucleic acid binding ligand, e.g., a DNA polymerase, e.g., Taq polymerase, or which supports the amplification of a product from a region of the first duplex at a first rate of amplification; and a second single stranded primer which when hybridized to a complementary single stranded molecule, results in a second double stranded (duplex) structure having a second value for a free energy parameter, e.g., a preselected $T_m$ or a preselected affinity for a nucleic acid binding ligand, e.g., a DNA polymerase, e.g., Taq polymerase, or which supports the amplification of a product from a region of the second duplex at a second rate of amplification.

The method includes:

(1) determining the value of a free energy-parameter of a duplex formed by the hybridization of a test single stranded nucleic acid molecule to a first (complementary) target sequence;

(2) comparing that value with a reference value for a free energy parameter; and (3) if the determined value exhibits a preselected relationship with a reference value adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand nucleic acid molecule with a free energy parameter value having the preselected relationship with the reference value is found, and adopting all or part of that single stranded test nucleic acid molecule as all or part of the sequence of a first primer, thus providing a first primer having a preselected relationship with a reference value for the free energy, e.g., having a preselected relationship with the free energy parameter value for the second primer of the set.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

In preferred embodiments the method further includes providing a second primer by:

(1) determining the value of a free energy-parameter of a duplex formed by the hybridization of a test single stranded nucleic acid molecule to a second (complementary) target sequence;

(2) comparing that value with a reference value for a free energy parameter; and (3) if the determined value exhibits a preselected relationship with a reference value adopting all or part of the test single stranded nucleic acid molecule as all or part of the single stranded nucleic acid molecule, but if the determined value does not exhibit a preselected relationship with the reference value, repeating steps (1) and (2) on one or more subsequent test single stranded nucleic acid molecules until a test single strand with a free energy parameter value having the preselected relationship with the reference value is found, and adopting all or part of that single stranded test nucleic acid molecule as all or part of the sequence of a second primer, thus providing a second primer having a preselected relationship with a reference value for the free energy parameter, e.g., the value of the free energy parameter of the first primer.

In preferred embodiments: the value of the free energy-parameter formed by the hybridization of a test single stranded nucleic acid molecule to a complementary sequence (formed in step (1)) does not exhibit a preselected relationship with the reference value and a subsequent test single strand nucleic acid molecule is provided by permuting the test single strand nucleic acid molecule.

In preferred embodiments, steps (1), (2), and (3), are performed to provide a first single stranded nucleic acid sequence which can form a duplex having a preselected value for a free energy parameter, and the cycle of steps (1), (2), and (3), are repeated using the first single stranded nucleic acid as a starting point to provide a second single stranded molecule (which is a permutation of the first) which when hybridized to a complimentary single stranded nucleic acid results in a duplex having a preselected value for a free-energy parameter. The second single strand nucleic acid molecule can have a value for a free-energy parameter which is greater than, or less than, the value of the parameter for the first single strand nucleic acid molecule.

In preferred embodiments: the free energy parameter is correlated to with the amplification rate of a product from the duplex, e.g., the DNA polymerase-based amplification in a PCR reaction, and the first single stranded primer, when hybridized to a first (complementary) target single stranded molecule, results in a first double stranded (duplex) structure which supports the amplification of a product from a region of the first duplex at a first rate of amplification, the second single stranded primer, when hybridized to a second (complementary) single stranded target molecule, results in a second double stranded (duplex) structure which supports the amplification of a product from a region of the second duplex at a second rate of amplification, and the first amplification rate and the second amplification rate have a preselected relationship with one another, e.g., the first amplification rate, e.g., an amplification rate which is approximately equal with that of the second primer, or is sufficiently close to that of the second primer that it allows detection of both amplification products in a single reaction, e.g., in a single PCR reaction.

In preferred embodiments: the first and second free energy parameter values and thus the first and second rates of amplification, are approximately equal; the values for the first and second free energy parameter, and thus the first and second rates of amplification, are sufficiently similar, such that they allow detection of both amplification products in a single reaction, e.g., a single PCR reaction; the values for the first and second free energy parameter, and thus the first and second amplification rates, are sufficiently similar such that they allow detection of both amplification products after q, wherein q is an integer between 1 and 100, inclusive, cycles of amplification of one of the amplified regions, e.g., the region with the highest or the region with the lowest rate of amplification; the first and second region are on the same molecule; the first and second region are on different molecules; the regions are on one or more preselected molecules.

In preferred embodiments the primers are used to amplify a target sequence in an amplification-based reaction, e.g., a DNA polymerase-based reaction, a PCR, a ligase chain reaction, or a cycling probe reaction.

In preferred embodiments: the value for a free energy parameter is determined by, beginning at a first base pair of the duplex, determining a value for the free-energy parameter of n base pairs in a window, where n is any integer between 1 and 1,000, inclusive, (preferably or is less than 10, 20, 30, 40, 50, 100, 200, 300, 400, 500, or 1,000) moving the window to another base pair, and determining a value for the free energy parameter of the next window, and repeating the process for some or all of the remaining base pairs of the duplex, preferably, the windows are determined in the linear order in which they appear on the duplex; the free energy $\Delta G_D^\circ$ of duplex melting for the duplex formed by a test single stranded nucleic acid molecule is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation:

$$\Delta G_{total} = \Sigma_i \Delta G_{i,i+1} + \Delta G_{sym} + \Delta G_{int}.$$

In other preferred embodiments the method includes: relating the reactivity of a duplex to another free energy parameter, e.g., $T_m$, by the proprtionality constant or function κ, wherein κ can be determined by determining a free energy parameter, e.g. free energies $\Delta G_D^\circ$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$\ln(k^H/k^l) = (\kappa/RT)(\Delta G_D^{ol} - \Delta G_D^{oH}),$$

or, if the relative composite relative reaction rates are binding limited, the calculated relative binding constants are determined by means of an equation, e.g., the equation, $$\ln(K^{II}/K^{I}) = (\kappa/RT)(\Delta G_D^{oI} - \Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, $\kappa$ is a proportionality constant or function, wherein $\kappa$ is predetermined in accord with the above-recited equations for the ligand and for set sequence length by calculating free energies of melting $\Delta G_D^\circ$ for at least two preselected DNA flanking sequences if $\kappa$ is a proportionality constant, or at least three if a function, determined in accord with the summing step; a value for $\kappa$ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D^\circ$ as determined in accord with above-recited equations; and choosing a primer having a DNA flanking sequence and a DNA binding site for a ligand, the flanking sequence providing a binding constant or composite rate of reaction of the ligand with the DNA binding site of preselected value, e.g., a value which is less than, greater than, or about equal to that of a reference value, e.g., that of a reference flanking sequence. (Every ligand has a $\kappa$. $\kappa$ relates the reactivity of a nucleic acid to another free energy parameter, e.g., $T_m$. $\kappa$ can be used to relate the reactivity of a nucleic acid to another free energy parameter when the ligand binder is a duplex or a single strand binder, or when the nucleic acid is a single strand or a duplex.)

In other preferred embodiments: the primer sequence, does not hybridize with any other primer.

In other embodiments: the method further includes using the primers to detect the presence or absence of a target sequence or sequences in, e.g., a PCR reaction; the method further includes contacting the primers of the set with a sample, e.g., in a PCR reaction, and measuring relative or actual composite reaction rates of amplification, or detecting the generation of amplification products, by any method suited for the purpose, including e.g., gel techniques, spectroscopic methods, electrochemical methods, or biochemical assay methods; the method further includes choosing at least one set of primers with approximately equal calculated relative composite reaction rates for amplifying, or generating amplification products for, at least two different regions contacting the primers of the set with a sample, and detecting the presence of the regions in, e.g., a PCR reaction.

In another embodiment: the method further includes detecting the presence or absence of a target sequence or sequences, which if present in a subject indicates that the subject is suffering from or predisposed to an infection (e.g., septicemia) by an organism or virus related to the target sequence or sequences, e.g., a protozoan, viral, bacterial, or yeast sequence.

In another embodiment: the method further includes detecting the presence or absence of a target sequence or sequences, which if present in a subject indicates that the subject is suffering from or predisposed to a disorder, e.g., and inherited disorder, related to the target sequence or sequences.

In other preferred embodiments the method includes: choosing at least one set of DNA primers with approximately equal calculated relative composite reaction rates for amplifying, or generating amplification products for, at least two different target sequences and using the DNA primers to detect the target sequences, wherein the calculated relative composite reaction rates fall within a predefined deviation about a mean relative composite reaction rate; using at least one set of DNA primers for two different target regions to detect the presence or absence of the target regions, which if present indicates that a subject is suffering from a disease or diseases related to the target sequence or sequences, which comprises combining aliquots of at least one set of DNA primers with an analytical unknown sample which may or may not contain a target sequence or sequences, performing the amplification reaction to generate amplified concentrations or amplification products of the target sequence or sequences, if present, and observing by any suitable qualitative or quantitative method the presence or absence of, the preselected or native DNA sequence or sequences.

In still another embodiment, the invention provides a method of detecting the presence or absence of a nucleic acid, e.g., a DNA sequence or sequences corresponding to a disease causing organism or virus, e.g., an agent for an infectious disease, e.g., a viral agent, e.g., human immunodeficiency virus, which includes: providing a set of DNA primers which amplify, or generate amplification products for, at least two different regions from the corresponding nucleic acid sequence at approximately equal rates, and measuring relative or actual composite reaction rates of amplification or generation of amplification products using the nucleic acid primers by any method suited for the purpose; choosing at least one set of nucleic acid primers with approximately equal calculated relative composite reaction rates for amplifying, or generating amplification products for, at least two different regions from the corresponding nucleic acid sequence and using the nucleic acid primers to detect target sequences, wherein the calculated relative composite reaction rates fall within a predefined deviation about a mean relative composite reaction rate; providing nucleic acid primers for two different regions of the nucleic acid sequence or sequences to detect the presence or absence of the nucleic acid sequence or sequences corresponding to the organism or virus (e.g., human immunodeficiency virus), combining aliquots of the nucleic acid primers with a sample which may or may not contain the nucleic acid sequence or sequences, performing the amplification reaction to generate amplified concentrations or amplification products of the nucleic acid sequence or sequences, if present, and observing by any suitable qualitative or quantitative method the presence or absence of, the nucleic acid sequence or sequences corresponding to the organism or virus, wherein suitable methods include gel techniques, spectroscopic methods, electrochemical methods, or biochemical assay methods, thereby detecting the presence or absence of the nucleic acid sequence or sequences corresponding to the organism or virus.

In another aspect, the invention features, a set of primers, or a reaction mixture, including:

a first single stranded primer which when hybridized to a complementary single stranded molecule, results in a first double stranded (duplex) structure having a first value for a free energy parameter, e.g., a preselected $T_m$ or a preselected affinity for a nucleic acid binding ligand, e.g., a DNA polymerase, e.g., Taq polymerase, or which supports the amplification of a product from a region of the first duplex at a first rate of amplification; and a second single stranded primer which when hybridized to a complementary single stranded molecule, results in a second double stranded (duplex) structure having a second value for a free energy parameter, e.g., a preselected $T_m$ or a preselected affinity for a nucleic acid binding ligand, e.g., a DNA polymerase, e.g., Taq polymerase, or which supports the amplification of a product from a region of the second duplex at a second rate of amplification, provided that: the free energy parameter value or the amplification rate of the first primer is approximately equal the free energy parameter value or the amplification rate of the second primer; the free energy parameter value or the amplification rate of the first primer is sufficiently similar to that of the second primer such that detection of both amplification products in a single reaction, e.g., in a single PCR reaction is possible; the first and second free energy parameter values and thus the first and second rates of amplification, are approximately equal; or the values for the first and second free energy parameter, and thus the first and second amplification rates, are sufficiently similar such that they allow detection of both amplification products after q, wherein q is an integer between 1 and 100, inclusive, cycles of amplification of one of the amplified regions, e.g., the region with the highest or the region with the lowest rate of amplification.

In preferred embodiments: the primers are DNA molecules.

In preferred embodiments the reaction mix includes a target sequence and: one or both of a primer and the target sequence are DNA; one or both of a primer and the target sequence are RNA; the target sequence is RNA and the primer is DNA; a primer is a single stranded probe; the target sequence which is to be detected or amplified is a naturally occurring sequence, e.g., a genomic molecule, or chromosome, e.g., a viral, bacterial, plant, or animal nucleic acid; a primer is a synthetic, purified natural, genetically engineered, or recombinant DNA or RNA molecule, and the target sequence is a naturally occurring nucleic acid, e.g., a genomic molecule, or chromosome, e.g., a viral, bacterial, plant, or animal nucleic acid; the reaction mix includes nucleic acid binding ligand, e.g., a ligand which amplifies the target, e.g., DNA polymerase e.g., TAQ polymerase, a ligase, e.g., DNA ligase.

In preferred embodiments: a target nucleic acid is at least 10× bases in length, wherein x is an integer between 1 and 1,000, inclusive, e.g., at least 10, 20, 30, 40, 50, 100, 200, 300, 400, or 500, base pairs in length; a target nucleic acid is less than 10× bases in length, wherein x is an integer between 1 and 1,000, inclusive, e.g., less than 10, 20, 30, 40, 50, 100, 200, 300, 400, or 500, base pairs in length; a primer is at least x bases in length, wherein x is an integer between 1 and 500, inclusive, e.g., at least 10, 20, 30, 40, 50, 100, 200, 300, or 400 base pairs in length; a primer is less than x bases in length, wherein x is an integer between 1 and 500, inclusive, e.g., less than least 10, 20, 30, 40, 50, 100, 200, 300, or 400 base pairs in length.

In another aspect, the invention features a method of predicting the relative susceptibility of a site on a nucleic acid duplex to perturbation. The method includes: determining the value of a free energy-parameter of a duplex which includes or flanks the site, the value for the free energy parameter being predictive of the susceptibility of the site to perturbation.

In preferred embodiments, the method further includes, providing a nucleic acid sample including the site from a subject, and determining if there is a mutation at the site, a mutation at the site being indicative of risk of a disorder, e.g., a neoplastic disorder.

In preferred embodiments the site is: a base pair; a plurality of base pairs, e.g., p base pairs wherein p is an integer between 1 and 1,000; the site is less than 10, 20, 30. 40, 50, 100, 200, 400, 500, or 1,000 base pairs in length.

In preferred embodiments: the value for a free energy parameter is determined by, beginning at a first base pair of the duplex, determining a value for the free-energy parameter of n base pairs in a window, where n is any integer between 1 and 1,000, inclusive, (preferably n is less than 10, 20, 30, 40, 50, 100, 200, 300, 400, 500, or 1,000) moving the window to another base pair, and determining a value for the free energy parameter of the next window, and repeating the process for some or all of the remaining base pairs of the duplex, preferably, the windows are determined in the linear order in which they appear on the duplex; the free energy $\Delta G_D^\circ$ of duplex melting for the duplex which includes or flanks the site is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation:

$$\Delta G_{total} = \Sigma_i \Delta G_{i,i+1} + \Delta G_{sym} + \Delta G_{int}.$$

In other preferred embodiments the method includes: relating the reactivity of a duplex to another free energy parameter, e.g., $T_m$, by the proportionality constant or function κ, wherein κ can be determined by determining a free energy parameter, e.g. free energies $\Delta G_D^\circ$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$\ln(k^{II}/k^I) = (\kappa/RT)(\Delta G_D^{oI} - \Delta G_D^{oII}),$$

or, if the relative composite relative reaction rates are binding limited, the calculated relative binding constants are determined by means of an equation, e.g., the equation, $$\ln(K^{II}/K^I) = (\kappa/RT)(\Delta G_D^{oI} - \Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, κ is a proportionality constant or function, wherein κ is predetermined in accord with the above-recited equations for the ligand and for set sequence length by calculating free energies of melting $\Delta G_D^\circ$ for at least two preselected DNA flanking sequences if κ is a proportionality constant, or at least three if a function, determined in accord with the summing step; a value for κ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D^\circ$ as determined in accord with above-recited equations. (Every ligand has a κ. κ relates the reactivity of a nucleic acid to another free energy parameter, e.g., $T_m$. κ can be used to relate reactivity of a nucleic acid to another free energy parameter when the ligand binder is a duplex or a single strand binder, or when the DNA is a single strand or a duplex.)

In preferred embodiments: the nucleic acid duplex is a nucleic acid sequence from an organism or virus which is the agent of a disease, e.g., an agent of an infectious disease, e.g., an HIV sequence, or in the case of a single stranded virus, the viral sequence hybridized to a complementary sequence; the method further comprises selecting a base pair within the region susceptible to perturbation and expressing an amino acid with an amino acid change resulting from a mutation in the region, and preferably making an antibody to the mutant protein.

In preferred embodiments the site is a nucleic acid sequence which when subject to perturbation, e.g., mutation, results in a disorder, or in an increased risk for the disorder and: the disorder is a neoplastic disorder; the disorder is manifest in the individual tested or in the individual's offspring; the method further includes determining if the site in an individual is more perturbation sensitive than a reference site, thereby providing a measure of the susceptibility of the individual or the individual's offspring to the disorder.

In another aspect, the invention features a method of constructing a map of the relative susceptibility to perturbation of a plurality of sites in a region of a nucleic acid duplex. The method includes:

(1) determining the value of a free energy-parameter of a first site in the region, the free energy parameter being correlated to susceptibility to perturbation; and (2) determining the value of a free energy-parameter for each remaining site in the region, thereby providing a map of the free energy-parameter values for the sites in the region of the duplex, the value of the free energy parameter being correlated with the susceptibility of a site to perturbation.

The value of the free-energy parameter can be determined, e.g., empirically, semi-empirically, or by calculation, e.g., by a method described herein, or by any method known to those in the art.

In preferred embodiments the site is: a base pair; a plurality of base pairs, e.g., n base pairs wherein n is an integer between 1 and 1,000; the site is less than 10, 20, 30. 40, 50, 100, 200, 400, 500, or 1,000 base pairs in length In preferred embodiments a region is: all or part of a gene; a plurality of sites, e.g., p sites wherein p is an integer between 1 and 1,000; is less than 10, 20, 30. 40, 50, 100, 200, 400, 500, or 1,000 sites.

In preferred embodiments: the value for a free energy parameter is determined by, beginning at a first base pair of the site, determining a value for the free-energy parameter of n base pairs in a window, where n is any integer between 1 and 1,000, inclusive, (preferably or is less than 10, 20, 30, 40, 50, 100, 200, 300, 400, 500, or 1,000) moving the window to a subsequent base pair, and determining a value for the free energy parameter of the that window, and repeating the process for some or all the remaining base pairs in the site, preferably, the windows are determined in the linear order in which they appear in the site; the free energy $\Delta G_D^\circ$ of duplex melting for the duplex formed by a single stranded sequence is determined, e.g., by summing free-energy values for hydrogen-bonding and stacking interactions for the nucleotide bases constituting the sequence; free-energy values are predetermined by semi-empirical thermochemical methods; the free energy of melting for a duplex is determined by an equation, e.g., by the equation:

$$\Delta G_{total} = \Sigma_i \Delta G_{i,i+1} + \Delta G_{sym} + \Delta G_{int}.$$

In other preferred embodiments the method includes: relating reactivity of a duplex to another free energy parameter, e.g., $T_m$, by the proprtionality constant or function κ, wherein κ can be determined by determining a free energy parameter, e.g. free energies $\Delta G_D^\circ$ of duplex melting, for the duplex formed by each test single stranded nucleic acid molecule, e.g., by summing free-energy values for hydrogen-bonding and stacking interactions for the nucleotide bases constituting each potential single strand sequence, wherein such free-energy values are predetermined by semi-empirical thermochemical methods and determining relative composite reaction rates for the selected potential single stranded sequences by means of an equation, e.g., by the following equation, $$\ln(k^{II}/k^I) = (\kappa/RT)(\Delta G_D^{oI} - \Delta G_D^{oII}),$$

or, if the relative composite relative reaction rates are binding limited, the calculated relative binding constants are determined by means of an equation, e.g., the equation, $$\ln(K^{II}/K^I) = (\kappa/RT)(\Delta G_D^{oI} - \Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, κ is a proportionality constant or function, wherein κ is predetermined in accord with the above-recited equations for the ligand and for set sequence length by calculating free energies of melting $\Delta G_D^\circ$ for at least two preselected DNA flanking sequences if κ is a proportionality constant, or at least three if a function, determined in accord with the summing step; a value for κ is determined by measuring relative or actual composite rates of reaction or binding constants for synthetic or native DNA sequences containing the preselected DNA flanking sequences and relating the measured relative composite rates of reaction or binding constants to their respective differences in free energy of melting $\Delta G_D^\circ$ as determined in accord with above-recited equations. (Every ligand has a κ. κ relates the reactivity of a nucleic acid to another free energy parameter, e.g.,$T_m$. κ can be used to relate reactivity of a nucleic acid to another free energy parameter when the ligand binder is a duplex or a single strand binder, or when the DNA is a single strand or a duplex.)

In preferred embodiments: the nucleic acid duplex is a viral sequence, or in the case of a single stranded virus, the viral sequence hybridized to a complementary sequence; the nucleic acid sequence is an HIV sequence.

Providing includes, synthesizing, isolating, determining, designing, selecting, or supplying.

A reference or preselected sequence is any of: a naturally or a non—naturally occurring nucleic acid sequence, e.g., a naturally occurring sequence which binds a ligand; a sequence which has an approximately similar $\Delta G_D^\circ$ and length as a test sequence; a sequence which is of equivalent type (RNA or DNA) and of approximately the same length as a test sequence; a sequence with approximately the same GC:AT composition as a test sequence; a sequence with the $\Delta G_D^\circ$ of a nucleic acid, which in nature binds to a ligand.

A reference value for a parameter, e.g., free energy, is any of: the value for that parameter for a preselected or reference sequence; or a value chosen as a desired, preferred, or optimal value for a duplex.

A preselected relationship between two values can refer to any of situations where the first or determined value is less than, greater than, or approximately equal to a second or reference value.

A preselected value is a value with a preselected relationship with a reference value.

A free energy parameter is a parameter related to, (e.g., proportional to, or correlated to, or inversely correlated to)

the free energy of a duplex nucleic acid, e.g., to the free energy of melting or formation of a duplex (e.g., the free energy of melting, $\Delta G_D^\circ$), to stability or resistance to melting, to affinity for a nucleic acid-binding ligand, to a relative composite reaction rate with a ligand, or to the susceptibility of the duplex to perturbation.

Perturbation refers to a change in the primary, secondary, or tertiary structure of a nucleic acid or to an interaction of the nucleic acid with a ligand and includes: melting; ligand binding; mutagenesis; intercalation of a compound into the duplex; the breaking or forming of a covalent or non-covalent bond between an atom of the nucleic acid and another atom, e.g., the insertion of a base, the deletion of a base, the change in the identity of a base, a chromosomal rearrangement, e.g., an inversion; or a chemical modification of the nucleic acid, e.g., by methylation or alkylation.

Permuting a sequence refers to changing the sequence by any of: altering the chemical nature of a base in the sequence, e.g., changing the identity of the base, e.g., by substituting a T for an A, G, or C; by adding a base or deleting a base. Permutation can proceed by making a change at a single base, or by making changes at a plurality of bases.

Primer, as used herein, refers to a nucleic acid which when hybridized to a complementary single strand nucleic acid, either or both, allows detection of the complementary strand, or promotes a reaction between the primer, the complementary strand, the duplex formed between the two, and a nucleic acid binding ligand.

A nucleic acid binding ligand, as used herein refers to one or more of: a compound which binds to a nucleic acid in a sequence-specific way (e.g., a sequence specific cleavage enzyme, such as a restriction endonuclease, including EcoRI, HaeIII, and BglI, or an enzyme or other molecule which binds to a specific sequence, e.g., molecules which modulate the expression of a product encoded by a nucleic acid) or in a sequence-non-specific way (e.g., DNaseI or micrococcal nuclease); a protein; an enzyme; an enzyme or other molecule (and agonists or antagonists thereof) which alters the structure of a nucleic acid to which is binds, e.g., by breaking or forming a covalent or non-covalent bond, e.g., a hydrogen bond, between an atom of the nucleic acid and another atom, e.g., an atom of the same strand, an atom of the complementary sequence, or an atom of another molecule; an enzyme which cleaves one or both strands of the nucleic acid, and agonists or antagonists thereof; an enzyme which methylates or alkylates the nucleic acid, and agonists or antagonists thereof; an enzyme which promotes or catalyzes the synthesis of a nucleic acid, e.g., a polymerase which requires a double stranded prime, and agonists or antagonists thereof; a DNA polymerase, e.g., DNA polymerase I or Taq polymerase, and agonists or antagonists thereof; an enzyme which alters the primary or secondary structure of a nucleic acid, e.g., a topoisomerase, or an enzyme related to recombination or replication, and agonists or antagonists thereof; a DNA binding ligand, and agonists or antagonists thereof; a mutagen; a compound which enhances gene expression, and agonists or antagonists thereof; a compound which intercalates into a double stranded nucleic acid, and agonists or antagonists thereof; a compound which, when contacted with a reaction mixture comprising a first single stranded nucleic acid and a second single stranded nucleic acid will accelerate the rate of duplex formation at least n-fold, wherein n is an integer between 2 and 1,000, inclusive; a compound which will decrease the free energy of duplex formation by n-fold, wherein n is an integer between 1 and 1,000 inclusive; a small molecule, e.g., any metalloorganic compound, any heterocyclic compound, or any protein which binds a nucleic acid; proteins or other molecules which are associated with the structural organization of DNA in the cell nucleus, or the packaging of DNA, including histones and nucleosomes; nucleic acid binding mutagens or carcinogens, or agonists or antagonists thereof; viral proteins and agonists or antagonists thereof.

κ can be used in methods of the invention in which the reactivity of a duplex to a ligand is of interest or is to be determined. Methods of the invention are concerned with the general process

(a)

where E is any enzyme, D is a given DNA sequence, ED is the complex between the enzyme and DNA, and P is the product(s) produced the action of E on D. The overall rate of this reaction, $k_c$, can be expressed as $$k_c = K_1 k_2 [1 + k_2/k_{-1}]^{-1} \tag{b}$$

where $k_c$ = the composite second order rate constant for the reaction (two reactants and one product), $k_1$ = forward rate constant for the first step, $k_{-1}$ = reverse rate constant for the first step, $k_2$ = the rate constant for catalysis, and $K_1 = k_1/k_{-1}$ the equilibrium constant for forming the bound complex (e.g., $K_1 = e^{-\Delta G_1^\circ/RT}$.

From equation (b) (rewriting the expression in terms of energies instead of rates and equilibrium expressions)

$$-RT \ln k_c = -RT \ln K_1 - RT \ln k_2 + RT \ln[1 + k_2/k_{-1}] \tag{c}$$

$$\Delta G_c^{\ddagger + 0} = \Delta G_1^\circ + \Delta G_2^{\ddagger + 0} - RT \ln A_2 + RT \ln[1 + k_2/k_1] \tag{d}$$

It is an empirical fact that, $$\Delta G_c^{\ddagger + 0} = \kappa(\Delta G_D^\circ) \tag{e}$$

where $\Delta G_D^\circ$ = the free energy of melting the duplex, D, from equation (a) and κ = a constant that relates the composite activation free energy to the free energy of melting the duplex.

It follows that even if all that is known is the composite rate for two different DNA sequences, $k_c$ and $k_c'$, respectively and (independently) the melting free energies of the two duplexes, κ, may be determined directly viz (substituting into (e) and subtracting)

$$\kappa = RT \ln[k_c'/k_c]/(\Delta G_D^\circ - \Delta G_D^{0\prime}) \tag{f}$$

This is the explicit relationship between relative rates at which a nucleic acid, e.g., DNA, substrate for the same ligand react with respect to the free energy of the unbound substrate. This relationship will hold for all sequences using any given ligand. Therefore, if one knows the relative stabilities (e.g., Tm's) of DNA sequences the relative reaction rates may be explicitly specified. κ is discussed in more detail below, see e.g., pp75–79.

INTRODUCTION TO SEQUENCE DESIGN

A. Overview

Reactions between duplex DNA and ligands are largely dictated and mediated by the interplay of structural, thermodynamic and dynamic characteristics of DNA, and recognition mechanisms of reacting ligands. Ligands that bind to DNA span a broad range of sizes from small cations to large proteins and assembled protein aggregates. As might be expected, a wide variety of experimental strategies have been exploited to examine the sequence specificity, or lack thereof, exhibited by ligands that interact with DNA. Sequence dependent variations in local conformation and charge configuration along DNA are thought to be the principal means by which ligands discriminate between various DNA sequences. In efforts to define the thermodynamic basis of such sequence specific discrimination, a variety of parameters have been evaluated from studies of DNA alone and ligand/DNA complexes.

This section considers the relationship between sequence specific reactivity of ligands with DNA and sequence dependent stability of duplex DNA. Although ligand/DNA physical contacts and DNA rigidity and conformational constraints play an essential role in binding, much of the discussion herein is concerned with the role of non-contacted bps flanking a given binding site (so-called "context" effects) modulation of binding and reactivity attributed to. Section II below provides descriptions of the formulations and evaluations of sequence dependent DNA melting free-energy. Three recently reported sets of nearest-neighbor (n—n) sequence dependent free-energies derived from analysis of experimentally obtained DNA melting curves are presented. The DNA samples and evaluation methods employed in each of these studies are discussed and compared. Using each set of the n—n stability parameters, free-energy profiles of a 1635 bp restriction fragment from pBR322 are constructed. Melting free-energies are also calculated for seven short duplex DNA oligomers with model sequences and lengths of 12, 16 and 20 bps. Results of optical and calorimetric melting curves of the seven DNA oligomers collected in 115 mM Na$^+$solvent are reported. Analysis of these results allows an evaluation of thermodynamic parameters that govern the melting transitions of the DNAs. Differences between calculated and experimentally determined free-energies provide evaluations of the free energy of duplex initiation, $\Delta G_{init}$, for DNAs 12 to 20 bp long.

General features of ligand/DNA interactions revealed from quantitative footprinting techniques are described in section III. Implicit assumptions underlying these techniques and their shortcomings are discussed. Studies that have revealed effects of flanking DNA on actinomycin D binding at specific sites are presented. That the structural effects of actinomycin D bound to a central AGCT binding site in a DNA hexadecamer duplex extend well beyond the immediate vicinity of the drug binding site; and the two strands of the duplex respond differently are discussed. Similar influences of flanking sequence on restriction enzyme cleavage are also reviewed. Results of Alu I restriction enzyme attack rate studies, of the same seven model duplex oligomers on which melting analysis was performed, are presented. As will be shown, the melting behavior and sequence specific enzyme cleavage of these duplexes have been extensively characterized. Comparisons of cleavage rates and free-energies of melting reveal a direct linear correlation between duplex stability and Alu I cleavage rates. In combination, these studies suggest a new perspective from which to view DNA. A perspective from which relative reactivity of a ligand at specific sites on DNA is directly modulated by stability of the flanking, non-contacted DNA sequences. This perspective and conclusions are presented in the final section.

B. Emergence of Novel DNA Molecules

It can be convincingly argued that two of the most beneficial technological developments of the past decade to the field of DNA biophysical chemistry have been the advent of the automated DNA synthesizer and the widespread utilization of DNA methodologies derived from molecular biology. Dramatic improvements in the various physical techniques available for studying DNA/ligand interactions have also been made. Together these developments have sparked an explosion in the body of information available regarding DNA binding specificities of many site specific drugs and proteins. The pioneering synthesis efforts of Caruthers and co-workers in the early 80's [1–3] and the automated DNA synthesizer have facilitated preparation and characterization of an essentially infinite variety of novel DNA molecules. Homogeneously pure milligram quantities required for in vitro physical studies can now be routinely prepared. For example, well conceived and focused thermodynamic studies have been performed on a variety of duplex oligomers and novel DNA molecules such as intramolecular hairpins [4–34], dumbbells [35–49], parallel strand DNAs [50–55], triplexes [56–69], tetraplexes [70–74] and DNA/chemical hybrids [75–86]. In addition, well defined model sequences of much longer lengths have been cloned, expressed and isolated for melting and ligand binding studies [87–94]. Availability of both short and long molecules with well-defined lengths and sequences have provided an invaluable means for refining and improving theoretical models of DNA melting [87,88,95–100]. These samples have also facilitated empirical evaluation of theoretical parameters that consider effects of sequence dependent DNA stability [87,88,95–100]. In addition to facilitating higher resolution experimental and theoretical melting studies, availability of model sequence molecules have also allowed investigations of relationships between DNA sequences and specific and non-specific interactions with ligands [101–104]. Advances in both acquisition and understanding of DNA melting and ligand reactivity data have made possible the comparative study described in this chapter.

SEQUENCE DEPENDENT DNA STABILITY

A. Modeling DNA Stability

Double helical DNA structure is maintained by a number of forces. Among these are the strong Coulombic interactions between phosphates along and across the backbone, hydrogen bonding between bps across the helix axis, stacking interactions between bps along one strand and across the helix axis, and a multiplicity of interactions with charged and polar solvent components. Presently,the understanding of these interactions makes it difficult to construct a realistic atomic model that correctly simulates the helix-coil or melting transition in DNA. In consolation, melting behavior can be reasonably modeled with parameterized statistical thermodynamic treatments.

To date the most successful analytical approaches to modeling the helix-coil transition in DNA have foundations in the statistical thermodynamic formalism of the modified using model [87,105–107]. In this approach the central assumption is that each bp of a DNA helix can occupy only one of two possible states. These are the "intact" and "broken" states. In the "intact" state a given bp is presumed to be hydrogen bonded and completely stacked with its neighboring bps on either side. Alternatively, in the "broken" or melted state a bp is non-hydrogen bonded, completely unstacked from its neighbors on either side with maximum solvent exposure. A clear distinction between the broken or "open" state in this theory and the bp state responsible for imino proton exchange has been made [38].

Models of DNA melting have been presented that consider bp stability as arising from independent contributions of individual bps [30,31,38,42,44,45,108]. Other models have been formulated that consider n—n sequence dependent stability of DNA in terms of bp doublets [42,98,99]. Model calculations have been compared with actual absorbance versus temperature measurements (melting curves). From these comparisons, within the context of the two-state per bp model, the sequence dependent energetics of DNA melting have been empirically evaluated [42,87,88,98–100].

B. Two Component DNA

Over the past 30 years optical and calorimetric melting studies of duplex DNA have established that the melting temperature, $t_m$, of DNA is a linearly increasing function of the percentage of the bps that are of the guanine-cytosine type (% G·C) [42,109,110]. Greater stability of DNA with increased % G·C can most readily be attributed to the difference between G·C bps, with three hydrogen bonds, and A·T bps with two hydrogen bonds. Sequence dependent stacking interactions between neighboring bps (described later) also contribute to this difference in a minor way. Thus, to first order, DNA stability can be expressed as a number weighted sum of the individual energies of two components, these being the energies of A·T (T·A) and G·C (C·G) bps. For a specific sequence, i, this energy (the H-bond energy) can be designated, $$\Delta G_{H-bond}(i) = \Delta S_{AT} N_{AT} T_{AT} + \Delta S_{GC} N_{GC} T_{GC} \quad (1)$$

$N_{AT}$ and $N_{GC}$ are the numbers of A·T and G·C bps in the sequence and $T_{AT}$ and $T_{GC}$ are the average melting temperatures of A·T (T·A) and G·C (C·G) bps. The dependence of $t_m$ on solvent ionic strength is included in the values of $T_{AT}$ or $T_{GC}$. They have been empirically evaluated from melting curve analysis of a variety of DNAs collected as a function of solvent environment. Relationships that describe the dependence of $T_{AT}$ and $T_{GC}$ on [Na$^+$] were first reported by Frank-Kamenetski [111]. These are, $$T_{AT} = 355.55 + 7.95 ln[Na^+] \quad (2a)$$

$$T_{GC} = 391.55 + 4.89 ln[Na^+] \quad (2b)$$

$\Delta S_{AT}$ and $\Delta S_{GC}$ in eqn (1) are the average entropy changes associated with melting A·T and G·C bps. Calorimetric and spectrophotometric melting studies of long DNA polymers from both natural and synthetic origins have revealed the transition entropies of melting A·T and G·C bps a re virtually independent of bp type (A·T or G·C), temperature, and only weakly dependent on solvent ionic strength over reasonable limits (15 mM to 1.0 M NaCl) [88,112,113] These observations corroborate the early theoretical work of De Voe and Tinoco [114], who argued that entropy release accompanying melting of a bp complex can be determined from the release of rotatable bonds that are ordinarily constrained in the ordered, intact double helical conformation. Thus, when duplex DNA structure is formed from single strands, entropy reduction occurs from the restriction of six free single bonds per nucleotide that are no longer free. Assuming only three preferred conformations are available for each nucleotide residue per bp, the transition entropy in forming a bp can be written as, $$\Delta S = -2(6R \cdot ln3) = -26.2 cal/K \cdot mol \quad (3)$$

Coincidentally, this value is precisely the entropy of bp formation, $\Delta S = -24.85 \pm 1.84$ cal/K·mole, determined experimentally from the studies mentioned above [88]. Thus, $\Delta S_{AT} = \Delta S_{GC} = \Delta S$ and can be determined from the ratio, $$\Delta H_{AT}/T_{AT} = \Delta H_{GC}/T_{GC} = \Delta S \quad (4)$$

where $\Delta H_{AT}$ and $\Delta H_{GC}$ are enthalpy changes associated with melting A·T or G·C bps.

Although reasonable justifications for assumptions surrounding the use of a single value of $\Delta S$ have been presented, calorimetric and spectrophotometric melting studies of short duplex oligomers six to eight bps in length have revealed a sequence dependence of the melting entropy [100]. Although the actual origins of this discrepancy are unknown, one possible explanation for observations of a sequence dependent entropy of bp melting could be sequence dependent structure and stacking in dissociated single strands [115].

The bp transition enthalpies, $\Delta H_{AT}$ and $\Delta H_{GC}$, are also dependent on solvent ionic strength. Empirically derived equations for their determination in different Na$^+$ environments have also been reported [116]. For example, $$\Delta H_{AT} = -9300 - 456.01 \, ln[Na^+] \quad (5)$$

From eqns (2b) and (4), $\Delta H_{GC}$ can be determined. Therefore, if DNA is considered to be comprised of only two energetic components, the free-energy can be estimated directly from the sequence by substitution of the appropriate values from eqns (2), (4) and (5) in eqn (1).

C. Nearest-Neighbor Sequence Dependent DNA Stability

With the advent of high resolution spectrophotometric instrumentation and the ability to obtain large quantities of homogeneously pure DNA samples multi-model melting or "fine-structure" was discovered on optical melting transitions of heterogeneous sequence DNA fragments [97, 116–121]. Such fine structure was attributed to sequential melting of large DNA domains. Failure of simple two-component melting theories to accurately predict the observed DNA melting curve fine structure suggested the consideration of sequence heterogeneity in addition to sequence type might be required to improve theoretical predictions [97–99]. Since then, evaluation of the sequence dependent energetics of n—n stacking in DNA has been the subject of a number of melting studies conducted on a variety of DNA samples [cf42].

If n—n sequence dependent interactions are considered to comprise the sole sequence dependent contributions to DNA stability, there are 16 possible different n—n stacks. However, because of the anti-parallel structure of duplex DNA, six of these possible stacks are degenerate, and only 10 of the 16 possible stacks are unique and distinguishable. These unique stacks designated 5'-MN-3' are: AA=TT, AT, TA, CA=TG, GT=AC, CT=AG, GA=TC, CG, GG=CC, GC. In principle, there are 10 unique energies associated with the 10 possible unique n—n bp combinations that can be evaluated.

In the past decade a number of experimental melting studies have been conducted and analyzed in terms of n—n models [cf42]. These studies attempted to evaluate the n—n stacking component of sequence dependent stability of duplex DNA. In the following paragraphs the three most recent efforts toward this objective will be described in detail [42,88,100]. The results of the optical melting and calorimetric studies of Breslauer and co-workers on small synthetic duplex oligomers and polymers [100] will be summarized; the optical melting studies of Delcourt and Blake on long DNA restriction fragments (>3,000 bp) and evaluation of n—n stacking free-energies from theoretical analysis of sub-transitions of melting domains on differential melting curves [88]. Finally, melting studies and analysis of melting transitions of DNA dumbbells reported by Doktycz, et al. are reviewed [42]. In each of these studies the nature of the DNA samples and the manner in which n—n stacking interactions were evaluated are considerably different and thus warrant individual description. For the most part these studies also represent earlier experimental approaches and models that were employed by others and not specifically described here [98,99]. Where pertinent, these earlier studies are specifically mentioned.

For the evaluation of n—n sequence dependent energetics in DNA, two formats have been presented [cf42] that differ primarily in the manner in which the possible n—n interactions are formally described. Subsequently these formalisms are referred to as the "n—n doublet" and "single bp" formats. Distinguishing characteristics of these approaches, including the different DNA samples and methods of evaluating n—n interactions from analysis of optical melting curves, are presented in the following two sub-sections.

D. DNA Stability in Terms of Nearest-Neighbor Base Pair Doublets

The majority of experimental studies aimed at evaluating sequence dependent stability of DNA have analyzed melting curves in terms of bp doublets. In this approach, n—n sequence dependence is considered to arise from the cumulative contributions of the hydrogen bonds and n—n stacking interactions associated with a doublet of two bps. The individual contributions of bp hydrogen bonding and stacking are not separately distinguished. This model of n—n sequence dependent stability was employed by Breslauer and co-workers [100], Delcourt and Blake [88] and in the earlier work of Vologodskii et al. [99] and Gotoh and Tagashira [98]. Although the model employed by these workers was virtually identical, their DNA samples, experimental conditions and analytical methods were considerably different.

Breslauer and co-workers [100] reported results of an elaborate series of calorimetric and optical melting studies of 28 synthetic DNA oligomers. The sample set was comprised of duplex DNAs ranging from six to 10 bps in length and eight semi-infinite length polymers with homogeneous or purely repeating sequences. Optical and calorimetric melting curves of the oligomers and polymers were obtained in a solvent containing 1.0 M NaCl. Experimental melting transitions of the molecules were analyzed assuming they melt in a "two-state" or "all-or-none" manner. The criteria establishing "two-state" melting behavior for each DNA oligomer was equality of transition enthalpies determined from van't Hoff analysis of optical melting curves and measured directly by differential scanning calorimetry. From optical and calorimetric melting curves of the various DNAs, transition enthalpies, $\Delta H_{MN}$, and entropies, $\Delta S_{MN}$, for each of the 10 possible 5'-MN-3' n—n doublets were evaluated.

Values of $\Delta H_{MN}$ were employed to predict transition enthalpies, $\Delta H_{pred}$, of 12 duplex DNA oligomers ranging in length from six to 16 bps. When compared with experimentally observed enthalpy values, $\Delta H_{obs}$, $\Delta H_{pred}$ did not differ by more than 10% for any of the 12 molecules examined. Implicit in the reported values of $\Delta H_{pred}$ is the assumption that the helix initiation enthalpy is nil. That is, the unfavorable bimolecular helix nucleation free-energy is assumed to be entirely entropic in origin and therefore depend most predominantly on total DNA concentration.

From the reported values of $\Delta H_{MN}$ and $\Delta S_{MN}$, assuming the heat-capacity difference between intact and broken bps ($\Delta C_p$) is zero, the free-energy of each MN doublet, $\Delta G_{MN}$, can be determined at any temperature, T, from the Gibbs relation, $$\Delta G_{MN} = \Delta H_{MN} - T\Delta S_{MN} \quad (6)$$

Reported $\Delta G_{MN}$ values determined at 25° C., and rounded to the nearest 100 cal/mol, are given in column A of Table 1.

The finding of sequence dependent entropies by Breslauer et al. [100] is in direct contrast to results from melting analysis of long DNAs and theoretical calculations. Similar reports of sequence dependent entropies for melting short RNA molecules have been published [cf122]. As stated earlier precise origins of this discrepancy are unknown. One possibility may be the existence of sequence dependent single strand stacking. If appreciable amounts of stacking occur in some single strand DNA or RNA sequences, small deviations from two-state behavior could potentially occur. The result would be evaluations of sequence dependent entropies.

Delcourt and Blake [88] evaluated n—n interactions from melting analysis of an entirely different class of DNA molecules. They utilized techniques of molecular biology to construct a variety of plasmid DNAs. From these plasmids relatively long (4000–5000 bps) DNA restriction fragments, whose entire sequence was known, and whose differential melting curves displayed multiple peaks or "fine structure" were isolated. As mentioned earlier such fine structure is attributed to the cooperative melting of individual regions or domains. Locations of melting domains were determined from melting curves of linear plasmids that had been cut with restriction enzymes at different sites. Delcourt and Blake assumed each domain analyzed melted in a 2-state manner and analyzed their melting curves using the more sophisticated multistate statistical thermodynamic theoretical melting model [cf88]. Experimental transitions were collected in a solvent containing 75 mM Na$^+$. Thirty-five different domains or sub-transitions were analyzed. The shapes and melting temperatures of the sub-transitions were fit using the numerically exact statistical thermodynamic model of DNA melting. In their procedure, the n—n doublet stability parameter, $s_{MN}$, was evaluated by fitting calculated melting curves to experimental ones. In effect, $s_{MN}$ is the equilibrium constant for melting doublet MN and is given by $$s_{MN} = \exp[(\Delta S/RT)(T - T_{MN})] \quad (7)$$

Where $T_{MN}$, the effective melting temperature of doublet MN, was empirically evaluated for each doublet by simultaneous analysis of the 35 cooperative melting domains. That is, $T_{MN}$'s were evaluated by solving the set of linear equations generated from the sequence and transition temperature, $T_m$, of each domain analyzed, viz., $$T_m = \Sigma f_{MN} T_{MN} \quad (8)$$

where the sum is over the fractional frequencies, $f_{MN}$, of each type of n—n doublet present in each domain. In their analysis, Delcourt and Blake assumed the transition entropy for each n—n doublet, $\Delta S$, in eqn (7) was constant at $\Delta S = -24.85$ ($\pm 1.74$) cal/mol bp, independent of sequence. Thus, for the 35 domains analyzed, eqn (8) provided 35 equations in the 10 unknown $T_{MN}$ values; apparently overdetermining the system. Even though their system of equations was grossly overdetermined, reasonable convergence of the solution to a unique set of $T_m$'s required the inclusion of three additional constraint equations. Although not articulated by Delcourt and Blake, it turns out the inclusion of these constraints was an essential requirement for finding a unique solution of their system of linear equations. This arises from the fact that even though in principle there are 10 different possible n—n interactions in DNA, unless arbitrary constraints are introduced, the 10 n—n energies are not linearly independent and cannot be uniquely determined. For circular or semi-infinite repeating co-polymers only eight linear combinations of the 10 possible n—n interactions are linearly independent. For molecules with explicit ends, there are nine linearly independent combinations. This ninth combination considers the specific n—n contributions from the ends of the molecules examined. Thus, the additional constraint equations introduced by Delcourt and Blake were fundamentally required in order to obtain a unique solution for 10 unknowns from their system of linear equations. By invoking these constraints, the absolute generality of the solution is compromised and the resulting set of n—n doublet energies are strictly valid subject to the invoked constraint equations. It should be noted that the lack of linear independence of the 10 n—n free-energies was entirely ignored by Breslauer and co-workers [100].

The constraint equations utilized by Delcourt and Blake were derived from an equation generated by linearly fitting a plot of domain $T_m$ values versus the fraction of G·C bps, $F_{GC}$, in each domain. In 75 mM Na$^+$they obtained, $$T_m = 41.764 F_{GC} + 63.815° \text{ C}. \tag{9}$$

The three constraint equations were obtained from eqn (9) by substituting $F_{GC}$=0, 0.5 and 1.0 and assuming at each $F_{GC}$ the melting temperature given by eqn (9) can be expressed as a linear combination of the possible types of stacks with that $F_{GC}$. Thus, when $F_{GC}$=0, $T_m$=63.815° C. Assuming this $T_m$ can be written in terms of the sum of fractions of possible stacks with $F_{GC}$=0, $$(0.5)T_{AA(TT)} + (0.25)T_{AT} + (0.25)T_{TA} = 63.815° \text{ C}. \tag{10a}$$

Similarly when $F_{GC}$=0.5, eqn (9) yields, $$(0.25)T_{AG(CT)} + (0.25)T_{GA(TC)} + (0.25)T_{AC(GT)} + (0.25)T_{CA(TG)} = 84.697° \text{ C}. \tag{10b}$$

and finally, when $F_{GC}$=1.0, $$(0.50)T_{GG(CC)} + (0.25)T_{GC} + (0.25)T_{CG} = 105.579° \text{ C}. \tag{10c}$$

Note, eqns (10a–10c) have precisely the form of eqn (8).

With inclusion of these supplemental constraint equations the set of linear equations generated from the experiments of Delcourt and Blake could be uniquely solved for 10 unknowns. From their analysis the effective melting temperature of each MN doublet, $T_{MN}$ was obtained. $T_{MN}$ is related to the enthalpy, $\Delta H_{MN}$, and entropy, $\Delta S_{MN} = \Delta S$, $$T_{MN} = \Delta H_{MN}/\Delta S \tag{11}$$

From the set of $T_{MN}$ values and $\Delta S$, the free-energies of all 10 possible doublets could be determined as, $$\Delta G_{MN} = \Delta S(T_{MN} - T) \tag{12}$$

These values calculated at 25° C. are listed in column B of Table 1. The assumptions invoked to obtain a unique solution were apparently reasonable because the solution of empirically evaluated $T_M$'s was quite accurate. $T_M$'s of 35 domains ranging in size from 50 to 620 bps were predicted from the evaluated set of n—n interactions using eqn (8). Remarkable agreement was obtained between the calculated and observed melting temperatures of these domains with an average deviation between the observed and calculated $T_m$'s of only ±0.168° C.

E. DNA Stability in Terms of Individual Base-Pairs

In the doublet treatment described in the last sub-section n—n stacking is included with H-bonding in the composite energy of a bp doublet. Energetic contributions from H-bonding and n—n stacking are not individually distinguished. In both studies described so far, only these composite interactions modeled as a doublet were evaluated. Alternatively, n—n stacking and H-bonding contributions to stability can be separately considered and evaluated from melting experiments.

A vast amount of experimental melting data of a large variety of DNAs has clearly demonstrated on average, the $T_M$ is a linearly increasing function of increasing G·C percentage [42,88,109]. Even though the average behavior of $T_M$ versus % G·C is linear, small deviations from linearity have been observed with sequences of the same bp composition but different sequence order or distribution. To first order, these deviations can be attributed to differences in energy of the different constituent n—n stacks. Thus, if the precision of determining $T_M$ is such that these deviations can be clearly resolved, it is quite conceivable that the separate contributions of H-bonding and n—n stacking to duplex stability can be evaluated. In the following paragraphs this formal approach is reviewed.

In this so-called individual bp stability format, contributions to DNA thermodynamic stability are apportioned into two parts, i.e. H-bonding and n—n stacking. In this way a unique n—n dependent energy can be assigned to each individual bp along the DNA. The primary component of this energy includes the average effects of ionic strength on H-bonding, phosphate-phosphate interactions at the individual bp level and the type of hydrogen bonding strength (A·T versus G·C bps), essentially as given by eqn (1). In addition to the hydrogen bonding free-energy between complementary bps on opposite strands, sequence dependent stacking interactions with neighboring bps on either side are also considered.

Therefore, the free-energy change in forming bp i depends on the type of bp i (A·T or G·C) and establishing stacking interactions with neighboring bps i-1 and i+1. $\Delta G_i$ is given by $$\Delta G_i = \Delta S(T_i - T) \tag{13}$$

where:

$$T_i = T_{H-B} + (\delta G_{i-1,i} + \delta G_{i,i+1})/2\Delta S \tag{14}$$

$T_{H-B}(=T_{AT}$ or $T_{GC})$ is the average melting temperature of either an A·T (T·A) or G·C (C·G) type bp; this includes effects of the hydrogen bonding strength of eqn (1) and the average stacking interactions of all 10 types of n—n stacks. As written, the $\delta G_{i,i\pm 1}$ terms in eqn (14) are actually deviations from the average n—n stacking free-energy specific for each type of n—n stack and can take on ten different values. The n—n interactions in this format were recently evaluated by Doktycz et al. [42] from melting studies of a series of DNA dumbbell molecules.

In the study by Doktycz et al., 17 DNA dumbbells were constructed that have duplex stem sequences ranging in length from 14 to 18 bps linked on the ends by $T_4$ single strand loops. Fifteen of the molecules had the core duplex sequences: $^5$'G-T-A-T-C-C-(W-X-Y-Z)-G-G-A-T-A-C$^{3'}$ (SEQ ID NO: 8) where (W-X-Y-Z) represents a unique combination of A·T, T·A, G·C and C·G bps. The remaining two molecules had the central sequences (W-X-Y-Z)=A-C and A-C-A-C-A-C. These duplex sequences were designed such that the central sequences included different combinations of the ten possible n—n stacks in DNA. Since all of the 10 possible n—n stacks were represented this molecule set is complete.

Optical melting curves of the dumbbells were collected in solvents containing 25 mM, 55 mM, 85 mM and 115 mM [$Na^+$], 10 mM Phosphate, 1 mM EDTA, pH=6.8. At each [$Na^+$], a set of 17 linear equations was generated. Each equation of the set related the observed transition temperature, $T_m$ (k), of each dumbbell with the number of A·T and G·C type bps in the dumbbell duplex and the number and type of n—n stacks contained in the central unique region of the dumbbell stem. In general for the $k^{th}$ molecule with $T_m$ (k), $$\Delta S[NT_m(k)-(N_{A\cdot T}T_{A\cdot T}'+N_{G\cdot C}T_{G\cdot C}')] = \Sigma M_{k,s}\delta G_s(k) \quad (15)$$

Where again the average entropy change in forming an A·T or G·C bp in the dumbbell stem was assumed to be approximately the same. Following the work of Delcourt and Blake [88] and Klump [112], a value of –24.85 cal/mol·bp was used in all calculations. N, dictated by the self-complementary sequence, is the number of duplex bps that form when the dumbbell collapses from a melted circle to a duplex with single strand loops on both ends. $NA \cdot T$ and $NG \cdot C$ are the numbers of A·T and G·C bps in the dumbbell duplex region and $T_{A \cdot T}'$ and $T_{G \cdot C}'$ are their average melting temperatures in the dumbbell. Thus, the term in parentheses on the left hand side of eqn (15) includes the contributions of hydrogen bonding and average stacking to the duplex stem. On the right hand side of eqn (16) $M_{ks}$ is the number of times the n—n stack of type s=5'-MN-3', i.e. MN=AA= TT, AT, TA, CA=TG, GT=AC, CT=AG, GA=TC, CG, GG=CC, GC, occurs in the central core sequence of the $k^{th}$ dumbbell. $\delta G_s$ is the sequence dependent deviation from the average free-energy of stacking (over all 10 possible) for stack type s (=MN). All parameters required by the left hand side of eqn (15) could be determined from the duplex sequence (N, $N_{A\cdot T}$, $N_{G\cdot C}$), melting experiments ($T_m$, $T_{A\cdot T}'$, $T_{G\cdot C}'$) and independent measurements ($\Delta S$). The $\delta G_s$ values were the unknowns to be solved from the information supplied.

From the melting data of the 17 dumbbell molecules, eqn (15) provided 17 linear equations from which to determine the 10 $\delta G_s$'s. Provided at least 10 of the 17 available equations were linearly independent, the system of equations would be overdetermined and therefore soluble for 10 possible unique values of the $\delta G_s$'s. However, in the n—n approximation the maximum number of linearly independent equations is reduced (from 10) by constraints similar to those given in eqns (10a–10c). Consequently, for circular or semi-infinite repeating co-polymers only eight linear combinations of the 10 possible n—n interactions are linearly independent. Considering explicit n—n interactions with ends there are 14 possible unique interactions but only 12 of these are linearly independent. For a more complete and in depth description of this problem the reader is referred to the original paper by Gray and Tinoco [123] and the recent extension of their analysis to include ends and cuts [45]. Even though 10 unique n—n interactions could not be evaluated, a non-unique set of the $\delta G_s$'s could be determined using singular value decomposition (SVD) [124]. Because the values determined by SVD are not unique, they cannot be meaningfully compared with one another or with values obtained by different researchers. As such the values given in Table 1 are in fact non-unique. However, the non-unique values can be appropriately summed to yield the total deviation from average stacking for any duplex sequence.

The aforementioned melting studies of DNA dumbbells [42] were the first to investigate the ionic strength dependence of n—n stacking in DNA. Therefore it seems noteworthy to mention the general results. For comparisons of the values at different ionic strengths, the n—n interactions were presented as combinations of the deviations from average stacking for the 5'-3' bp doublets, $\delta G_i$. Because these combinations are linearly independent, they are unique. Titratable changes in these $\delta G_i$ values with changing salt environment were observed. In all salts the most stable unique combination was $\delta G_4 = (\delta G_{GpC} + \delta G_{CpG})/2$, and the least stable was the GpG/CpC stack, $\delta G_2 = \delta G_{GpG/CpC}$. In addition $x^2$ values of the fits of the evaluated $\delta G_i$'s to experimental data increased with decreasing [$Na^+$] suggesting that significant interactions beyond nearest-neighbors become more pronounced at lower ionic strengths, particularly at 25 mM $Na^+$.

In order to compare the n—n sequence dependent interactions evaluated from the studies of Doktycz et al. [42] with those of Breslauer et al. [100] and Delcourt and Blake [88], the singlet values obtained from dumbbells must be transformed into the doublet format. As discussed by Vologodskii et al. [99], the single bp and doublet formats can be united by defining an effective melting temperature, $T_{MN}$, of the doublet comprised of the neighboring bps M and N. Base pairs M and N each have individual melting temperatures $T_M$ and $T_N$ equal to $T_{AT}$ or $T_{GC}$ and a contribution from the stacking interactions between them. This stacking interaction is written as the deviation due to n—n stacking, $\delta T_{MN}$, of $T_{MN}$ from the average melting temperatures of bps M and N, i.e.

$$\delta T_{MN} \equiv T_{MN} - (T_M + T_N)/2 \quad (16)$$

$$\delta T_{MN} = \delta G_{MN}/\Delta S_{MN} \quad (17)$$

Assuming $\Delta S_{MN} = \Delta S$ and substituting these expressions in eqn (12) the free-energy of each n—n doublet is given by, $$\Delta G_{MN} = \Delta S[(T_M + T_N)/2 + \delta G_{MN}/\Delta S - T] \quad (18)$$

These non-unique bp doublet free-energies determined from the singlet values reported by Doktycz et al. [42] are given in column C of Table 1.

For any given DNA sequence the total free-energy of melting can be calculated using the reported non-unique singlet free-energy values and eqns (13) and (14), $$\Delta G_T(\text{singlet}) = \Sigma_i \Delta G_i \quad (19a)$$

or the doublet values using eqns (6) or (12), $$\Delta G_T(\text{doublet}) = \Sigma_{MN} \Delta G_{MN} \quad (19b)$$

However, as calculated in eqns (19a) and (19b), $\Delta G_T$ (singlet) is not strictly numerically equivalent to $\Delta GT$ (doublet). Due to the averaging in eqns (16) used to convert n—n singlet values in eqn (17) to doublets in eqn (18) the two summed expressions in eqns (19a) and (19b) are not numerically equivalent. For an N bp DNA, the correction factor required for numerical equivalence is, $$\Delta G_{cor} = \Delta G_T(\text{singlet}) - \Delta G_T(\text{doublet}) = \Delta S[(T_1 + T_N)/2 - T] \quad (20)$$

Calculated free-energies of long DNAs are relatively insensitive to this factor. This end contribution becomes increasingly significant for shorter DNAs.

F. Comparisons of the Sets of Nearest-Neighbor Dependent Interactions The three sets of 10 non-unique n—n interactions evaluated in each of the three studies described above are given in Table 1. As stated previously, only eight linear combinations of the 10 possible n—n interactions are linearly independent. In fact, only two of the 10 possible individual interactions (the AA=TT and GG=CC stacks) can be uniquely evaluated from melting studies of oligomer or polymer sequences. For this reason a direct comparison between any of the remaining individual n—n stacks in Table 1 is misleading and provides no insight into the differences between them. Fortunately, a meaningful comparison can be made for the set of linearly independent combinations given in Table 2 that were determined from the non-unique n—n interactions given in Table 1. Examination of the values of the unique linear combinations in Table 2 reveals both similarities and differences. Before these are described it should be reiterated that the samples, methods of analysis and ionic strength environments where experiments were performed are different. The methods used to extract n—n sequence dependent information are also slightly different. Recall, in the studies of Breslauer and co-workers [100] calorimetric and optical melting curves were evaluated for a variety of very short duplex sequences and semi-infinite perfectly repeating co-polymers in 1.0 M $Na^+$. Their unique combinations are presented in column A of Table 2. Delcourt and Blake [88] studied melting curves of long DNA restriction fragments collected in a solvent of 75 mM $Na^+$. The unique linear combinations determined from their reported values are displayed in column B of Table 2. The $T_{MN}$'s reported by Delcourt and Blake were quite comparable to those reported earlier by Gotoh and Tagashira [98] from analysis of restriction fragment melting curves in 19 mM $Na^+$. The values in column C were determined from the data reported by Doktycz et al. [42] obtained from melting analysis of DNA dumbbells in a solvent of 115 mM $Na^+$. (The notation here for the free-energy is $\Delta G$ rather than $\delta G$ used by Doktycz et al.) In that work $\delta G$ represented the deviation from the average, while here $\Delta G$ denotes the total free-energy. Considering the significant differences between the origin and nature of the DNA samples, the level of agreement in Table 2 is quite remarkable. For all three sets, the most stable combination is $\Delta G_4 = (\Delta G_{CG} + \Delta G_{GC})/2$ and the least stable combinations are $\Delta G_7$ and $\Delta G_8$. For the remaining combinations the values in columns B and C are quite comparable and the hierarchy of the values is precisely the same. The largest discrepancy for any values between columns B and C is in the first value, $\Delta G_1 = \Delta G_{AA(TT)}$ which differs by 229 cal/mol. The remainder of the values in columns B and C differ by less than 124 cal/mol. Perhaps not surprisingly the values in column A evaluated at a much higher $Na^+$ concentration, where DNA is inherently more stable, are larger in magnitude than the values in columns B and C. There are some similarities, but the hierarchy of values in column A of Table 2 is not the same as the values in columns B and C. Perhaps more meaningful than these direct comparisons are free-energies of duplex DNA fragments with well defined sequences calculated using the values in Tables 1 and 2. Comparisons from this standpoint are made in the next two sub-sections.

Figure 1A:
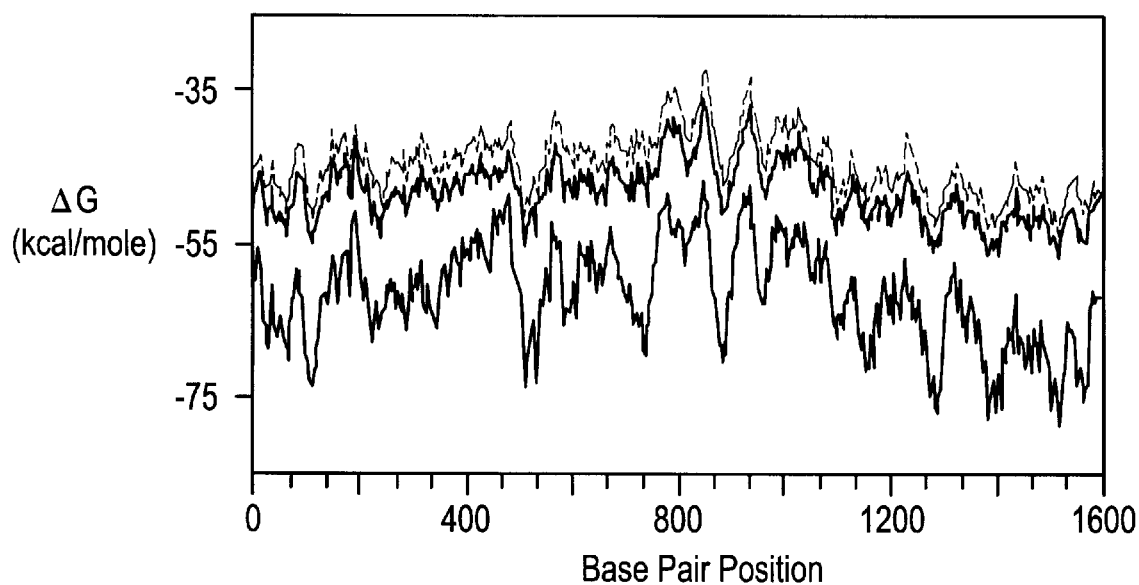
FIG. 1 is a graph of free energy profiles calculated for 30 base pair windows of the 1635 bp HinfI restriction fragment sequence from pBR322.
Figure 1B:
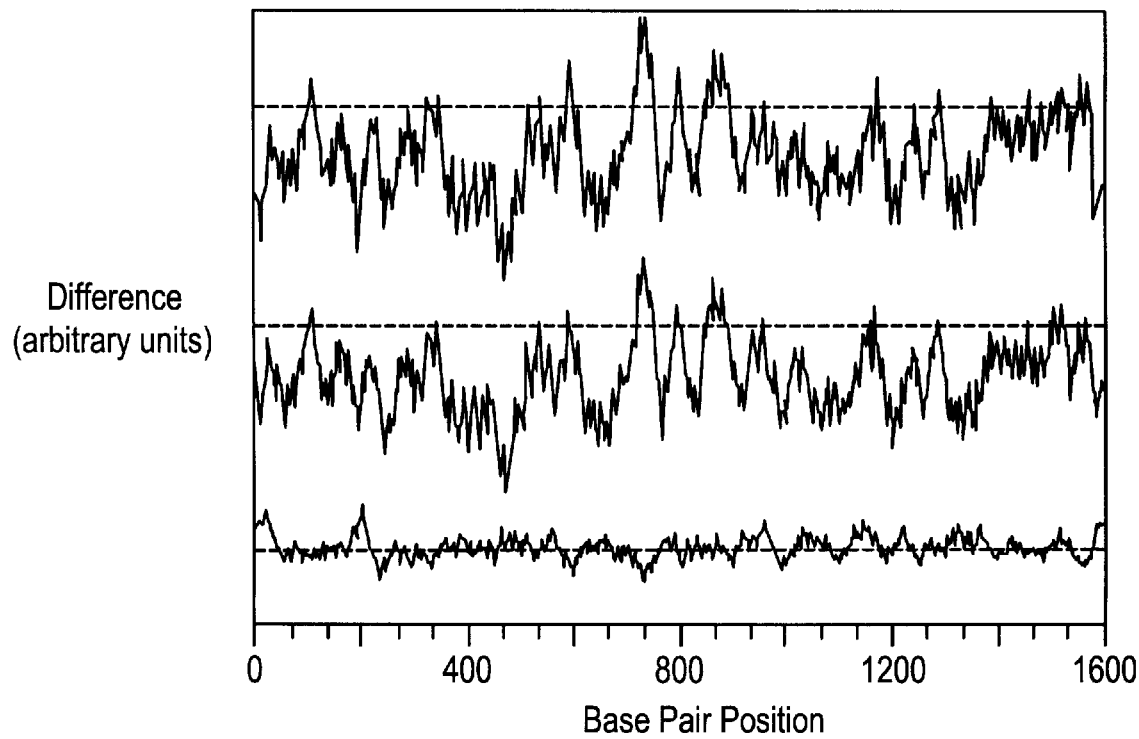

G. Use of Nearest-Neighbor Dependent Interactions to Calculate DNA Energy Profiles Clear comparisons can be made between the n—n parameters given in Tables 1 and 2 when the three parameter sets are used to calculate DNA energies. For this comparison a "window of energy" analysis is employed. Recently, several researchers have reported such "window" analysis of genetically active DNA sequences [125–127]. The "window" algorithm used computes the free-energy of consecutive overlapping windows of N bps along a DNA sequence. The n—n dependent free-energy of N bps in a window is calculated and plotted as a point. The window is then advanced one bp position along the sequence and the calculation is repeated for the new N bp window. Repeating the procedure to the end of the sequence results in an energy contour of the DNA. Such energy profiles were calculated for the sequence of the 1635 bp HinfI restriction fragment from plasmid pBR322 [128] using each of the three sets of n—n energies given in Table 1. Quantitative results of these calculations for a window width, N=30 bp are shown in FIG. 1a. Comparison of the resulting energy contours reveals those calculated using the values in columns B or C of Table 1 are quite similar in shape and magnitude. In contrast, the magnitude and range of the energy contour calculated using the values in column A of Table 1 is dramatically different. At some sequence positions large fluctuations, not present in the other profiles, are encountered. Qualitative differences of the energy contours are shown in FIG. 1b. These difference plots were constructed by first determining the numerical point by point differences between two energy profiles. From these values the range between the maximum and minimum differences over the entire sequence was determined. Remaining differences were normalized relative to this range and the fractional differences at each point along the sequence were plotted in arbitrary units. Results are shown on the plots in FIGS. 1b and 2b. Examination of these difference maps reveals the calculated energy contours using column A in Table 1 are not linearly related to differences between the other two contours (upper curves in FIG. 1b). In the difference profiles calculated using columns B and C of Table 1 (lower curve in FIG. 1b), fluctuations about zero are random. This is not the case for differences between the column A energy profile and the other profiles (upper curves in FIG. 1b).

Figure 2A:
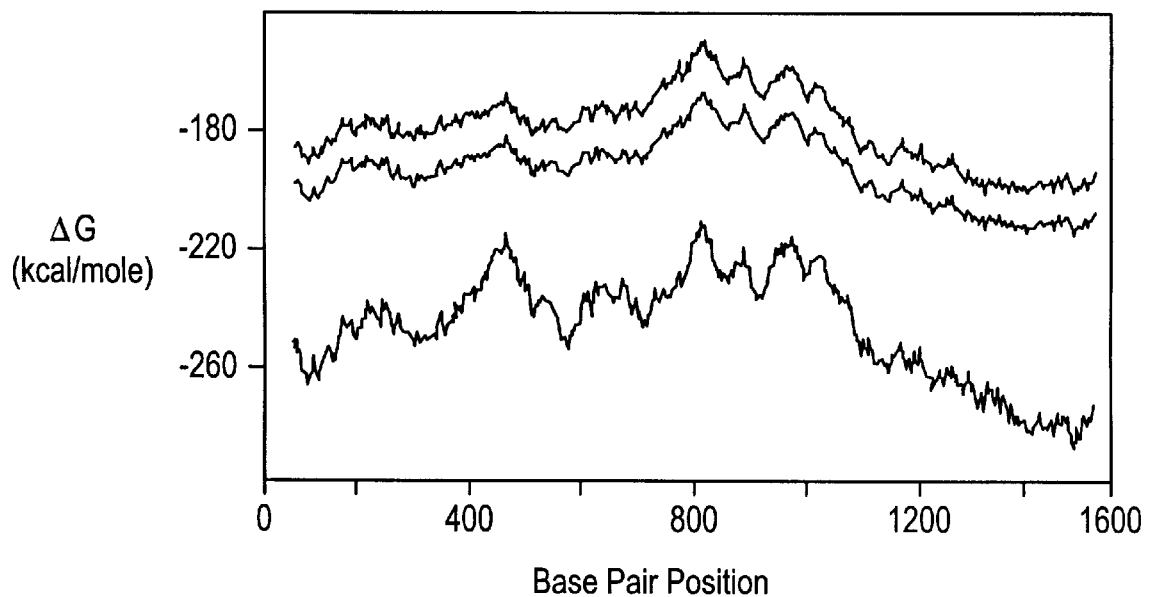
Figure 2B:
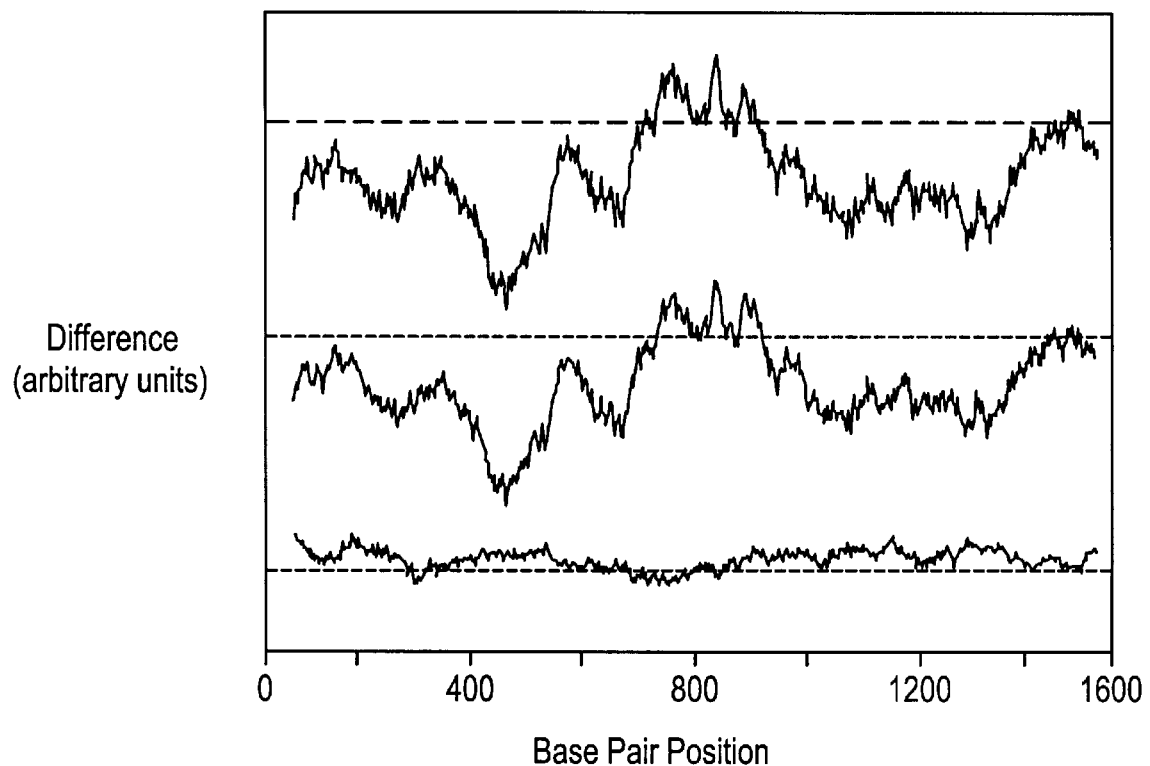

Expanding the window to N=120 bps, differences between calculated energy contours become even more pronounced. These contours and their difference plots are displayed in FIG. 2. Plots shown in FIG. 2a are similar to those in FIG. 1a and little similarity is seen between the energy profiles calculated using the n—n values in column A (lower curve) and columns B and C (upper curves) of Table 1. Evidently, DNA stability calculated using this window method is relatively sensitive to the set of n—n parameters employed.

H. Use of Nearest-Neighbor Dependent Interactions to Calculate the Free-Energy of DNA Melting Next is demonstrated how to employ the sets of n—n stacking parameters given in Table 1 to calculate the free-energies of 7 duplex DNA molecules is demonstrated. Although the values of the 10 n—n stacks given in Table 1 are not unique they can be appropriately summed to yield the free-energy of any duplex DNA sequence. If the n—n dependent interactions with the ends can be assumed to be the same for the different duplexes then the free-energies calculated by summing the pertinent non-unique values in Table 1, or the unique combinations in Table 2, will all be off by the same amount due to the end effect [45]. Thus (relatively speaking) the calculated energies are directly comparable. The following calculations are demonstrated using the appropriate sums of the values in Table 1.

Sequences of the seven molecules are shown in FIG. 3. The set is comprised of two 12-mers, three 16-mers and two 20-mers. Each of the DNA strands comprising the duplexes are self-complementary. When associated in the bimolecular duplexes as shown, the duplex of each molecule has the common central four bp sequence 5'-A-G-C-T-3' flanked on either side by the sequences $(AT)_n$ or $(AA)_n$, n=2,3,4 and $AA(AT)_2$ (SEQ ID NO: 5). Several factors motivated choosing the particular sequences shown in FIG. 3. Because for each length, the number of A·T (T·A) bps is the same, only the distribution of A·T and T·A bps differs for fragments of the same length. Therefore, any differences in stability between two fragments of the same size can be attributed to differences in the n—n sequences of the fragments. Another feature of these sequences is that the central-most four bp sequence is the recognition site of both restriction enzyme Alu I and the drug actinomycin D. The length of the molecules are such that their melting temperatures conveniently fall in a range that allows reliable acquisition and analysis of experimental melting curves. Finally, the sequences are short enough that their melting transitions may be accurately modeled with a two-state, all-or-none model. Although this assumption must be rigorously verified, the model facilitates a simple and straight-forward van't Hoff analysis for evaluation of the thermodynamic parameters of the melting transition [129]. In the n—n model, the total free-energy of any given duplex DNA sequence, $\Delta G_{total}$, can be written as, $$\Delta G_{total} = \Sigma_i \Delta G_{i,i+1} + \Delta G_{sym} + \Delta G_{int} \quad (21)$$

For an N bp sequence, the sum over i runs from 1 to N-1 and adds all the pertinent $\Delta G_{MN}$'s required for a particular sequence. $\Delta G_{sym}$ is a symmetry correction that accounts for the degeneracy in self-complementary versus non-self-complementary sequences. For duplex DNAs of the same length the entropy difference between non-self-complementary and self-complementary sequences due to symmetry is $\Delta S_{sym} = -1.4$ eu. Thus, at 298.15K, $\Delta G_{sym} = +0.41$ kcal/mol and introduces a slightly destabilizing effect on duplexes formed from self-complementary sequences compared to non-self-complementary sequences. The partial free-energies defined as, $$\Delta G_p = \Sigma_i \Delta G_{i,i+1} + \Delta G_{sym} \quad (22)$$

and calculated using the three sets of n—n values in Table 1 are listed in Table 3 for each of the DNAs shown in FIG. 3.

Table 3 readily reveals for the three n—n sets, the calculated higher stability of the $(AA)_n$ sequences over the $(AT)_n$ sequences. The 16 bp sequence $AA(AT)_2$ (SEQ ID NO: 5) has a calculated partial free-energy intermediate between those of the $(AA)_3$ (SEQ ID NO: 2) and $(AT)_3$ (SEQ ID NO: 1) 16 bp sequences. Magnitudes of the values in columns B and C are comparable. The values in column A are more negative ranging from -15.7 to -37.1 kcal/mol and are 20–40% higher in magnitude than the corresponding values in column B (-12.6 to -20.4 kcal/mol), and 15–35% higher than the values in column C. Differences in relative magnitudes are undoubtedly related to the lower ionic strength conditions (75 and 115 mM Na⁺) of the experiments performed to evaluate the parameters from which the values in columns B and C were determined. Recall the values in column A were determined from experiments conducted in 1.0 M NaCl. Although individual differences between the calculated partial free-energies for any single fragment vary over the ranges stated above, the hierarchy and magnitudes of the three sets are comparable.

In addition to the partial free-energies of eqn (22), the total free-energy, $\Delta G_T$, must also include the free-energy of helix initiation, $\Delta G_{int}$. $\Delta G_{int}$ accounts for the added difficulty of forming the first bp initiating the duplex compared to the subsequent formation of all other bps.

$$\Delta G_T = \Delta G_p + \Delta G_{int} \quad (23)$$

The universal length dependence of $\Delta G_{int}$ has not been clearly established. Breslauer and co-workers reported length independent values of $\Delta G_{int} = +5$ kcal/mol for DNAs containing G·C bps and +6 kcal/mol for duplexes containing A·T bps in 1.0 M Na⁺ [100]. These values are 40 to 50% higher than $\Delta G_{int}$ reported for association of short RNA duplexes in the same solvent [122]. Delcourt and Blake [88] analyzed internal melting domains within much larger duplex fragments. In their system, nucleation free-energy is replaced by the free-energy associated with the loop entropy of internal loop formation. For the dumbbells [42], the melting transitions are entirely concentration independent over the range of concentrations where experiments were conducted. Presumably $\Delta G_{int} = 0$ for dumbbells.

The precise value of $\Delta G_{int}$ that should be used to calculate the total free-energy of the fragments in FIG. 3 is not known. Because of this, the best set of energies in Table 3 that should be used is uncertain. To explicitly evaluate $\Delta G_{int}$, the DNAs in FIG. 3 were prepared and melting curves of them in 115 mM Na⁺ were collected Results of these experiments are presented next.

I. Comparisons of Predictions with Experiments for 12, 16 and 20 Base-Pair Duplex DNAs The single strand DNA oligomers that anneal to form the duplexes shown in FIG. 3, were synthetically prepared and characterized for purity by polyacrylamide gel electrophoresis according to methods known to those skilled in the art. In some cases DNA samples were electrophoretically purified as previously described. Samples were then exhaustively dialyzed versus the melting solvent (100 mM NaCl, 10 mM sodium phosphate, 1 mM EDTA, pH=7.5). When incubated at moderate ionic strength the potential exists for self-complementary oligomers to self-associate and form bi-molecular duplexes or fold to intramolecular hairpins. The unimolecular hairpin and bimolecular duplex can be clearly distinguished by their significantly different gel electrophoretic mobilities. Gel electrophoretic analysis was performed on every sample before and after collection of melting curves. In some cases this analysis revealed the presence of a population of faster migrating species in addition to the bi-molecular duplexes. When evidence for this species, assumed to be the intramolecular hairpin, was seen the data from the corresponding melting experiments were excluded from further analysis.

Absorbance versus temperature profiles (optical melting curves) were collected for each of the molecules at heating and cooling rates of 60° C. per hour over the temperature range from 5 to 85° C. A data point was collected approximately every 0.1° C. For each sample, melting curves were collected as a function of total strand concentration, $C_T$, over the 200 fold range from approximately 500 nM to 100 µM. Absolute absorbance readings ranged from 0.08 OD to 1.3 OD. Optically matched quartz cuvettes with 1 and 0.1 cm path lengths were employed. All melting curves were entirely reversible upon cooling at the same rate.

Optical melting curves were normalized to upper and lower baselines and converted to $\theta_B$ (the fraction of duplex molecules) versus temperature curves [30]. From these curves the transition temperature, $T_m$, was determined as the temperature where $\theta_B = 0.5$. These $\theta_B$ versus temperature curves were then analyzed assuming the transitions occur in an "all-or-none" or "two-state" manner. Implementing this assumption the thermodynamics of the transition could be evaluated from a van't Hoff plot of $1/T_m$ versus $\ln C_T$. The linear equation describing the resulting plot is, $$1/T_m = (R/\Delta H)\ln C_T + \Delta S/\Delta H \quad (24)$$

Clearly, from this analysis the slope of the van't Hoff plot yields $R/\Delta H$ and the intercept provides $\Delta S/\Delta H$.

The van't Hoff plots obtained from melting data collected on the seven linear DNA fragments of FIG. 3 are displayed in FIG. 4. All lines shown were excellent fits to the data (correlation coefficient R≧0.95). Model dependent thermodynamic parameters evaluated from the van't Hoff plots in FIG. 4 for the duplexes shown in FIG. 3 are listed in Table 4. The experimentally determined total free-energy was determined from ΔH and ΔS values at 298.15K given in Table 4.

$$\Delta G_T(E) = \Delta H - T\Delta S \tag{25}$$

Model independent thermodynamic parameters of the melting transitions of the DNAs in FIG. 3 were measured by differential scanning calorimetry (DSC). An MC-2 (Microcal, Northampton, Mass.) DSC instrument was employed. In preparation for calorimetric melting curve measurements synthetic DNA samples were deprotected and vacuum dried. Samples were then rehydrated in double distilled (dd) water and dialyzed against dd-water for four days. Upon removal from dialyses samples were vacuum dried and then rehydrated in melting buffer. Some samples were electrophoretically purified. Experiments performed on the same DNA with and without electrophoretic purification gave identical results. Sample and reference buffer solutions were filtered through 0.45 μM pore size filters. At least 25 to 100 OD units (absorbance at 260 nm in a 1 cm pathlength cuvette) of DNA solution was melted in the 1.2 ml reaction chamber of the calorimeter. DNA strand concentrations estimated from extinction coefficients determined by the n—n method [130], varied from 3 to 10 mM. These concentrations were from two to 10 times higher than in optical melting experiments. Calorimetric data was collected as the change in excess heat capacity, $\Delta C_p$, versus temperature, T. The average buffer base line determined from eight scans of the buffer alone was subtracted from these curves. The calorimetric transition enthalpy, $\Delta H_{cal}$, was determined from the area under the base line corrected $\Delta C_p$ vs. T curve, viz.

$$\Delta H_{cal} = \int \Delta C_p dT \tag{26}$$

The temperature of the maximum value of the baseline corrected $\Delta C_p$ versus temperature curve was the transition temperature, $T_m$. The calorimetric transition entropy, $\Delta S_{cal}$, was also determined from the baseline corrected $\Delta C_p$ as, $$\Delta S_{cal} = \int \Delta C_p / T \, dT \tag{27}$$

Calorimetric free-energies were determined from $\Delta S_{cal}$ and $\Delta H_{cal}$ by eqn (25). Model independent thermodynamic parameters obtained from DSC for the seven DNAs shown in FIG. 3 are displayed in Table 4. For every DNA sample at least five forward and reverse $\Delta C_p$ vs. T scans were made. Displayed values of $\Delta H_{cal}$, $\Delta S_{cal}$ and $\Delta G_{cal}$ are the averages from multiple experiments. Estimated experimental errors on these values were no more than ±3%.

For all the DNAs, comparison of the ΔH values given in Table 4 obtained from both the model dependent van't Hoff analysis of optical melting curves and model independent parameters measured by DSC, reveals close agreement within the cumulative experimental error of ±5%. Such agreement supports the two-state model dependent van't Hoff analysis. Averages of the model dependent and model independent values listed in Table 4 were employed for subsequent comparisons and analysis.

According to eqn (23), the free-energy of helix initiation can be determined for each fragment as, $$\Delta G_{int} = \Delta G_T - \Delta G_p \tag{28}$$

Values of $\Delta G_{int}$ determined from differences of appropriate values in Tables 3 and 4 are given in Table 5. Table 5 indicates $\Delta G_{int}$ has the opposite sign of $\Delta G_p$, revealing (as expected) helix nucleation makes a destabilizing contribution to the total free-energy of a duplex. Examination of the values in Table 5, reveals that $\Delta G_{int}$ is essentially independent of duplex length. However, magnitudes and standard deviations of the averages are different. The average of the values in column A is 15.1±3.9 kcal/mol compared to 6.8±1.2 kcal/mol for column B and 8.5±1.0 kcal/mol for column C. The standard deviation from the average is much greater (±26%) for the values obtained from the sets of $\Delta G_p$ reported by Breslauer and co-workers (column A, Table 3) [100] compared to (±18%) for the values of Delcourt and Blake (column B, Table 3) [88] and (±12%) obtained from the $\Delta G_p$ values reported by Doktycz et al. (column C, Table 3) [42]. These differences in the magnitudes of $\Delta G_{int}$ obtained from the different parameter sets are undoubtedly due to differences in the $Na^+$ environments where the $\Delta G_p$ values were determined and where the experimental free-energy, $\Delta G_T(E)$, was evaluated. An explanation for the differences in the standard deviations may be the higher accuracy of the $\Delta G_p$ values given in column C of Table 3 compared to columns A and B.

The free-energy of helix initiation, $\Delta G_{int}(N)$, is related to the helix nucleation parameter, β(N) [4,131] as, $$-RT\ln\beta(N) = \Delta G_{int}(N) \tag{29}$$

From the values in Table 5, β(N) was evaluated. Results of the evaluation are shown in FIG. 5. The findings of length independent values of $\Delta G_{int}$ for DNAs with 12, 16 and 20 bps is consistent with similar findings for short duplex DNAs and RNAs [100,122].

This section has reviewed DNA sequence dependent stability and presented the numbers for calculating duplex stability. The n—n values were used to calculate energy profiles for the 1635 bp HinfI fragment from plasmid pBR322 [128] and calculate free-energies of seven duplex DNAs ranging in length from 12 to 20 bps. Calculated results were compared with results from experimental analysis of melting transitions of the seven model DNA duplex oligomers. In the next section, results of rates of attack of these same model oligomers by several ligands are presented. These comparisons reveal a direct correlation between duplex instability stability and first strand cleavage rate.

III. Interactions of DNA with Ligands

A. Ligand Binding: Primary and Secondary Sequence Specificity

Historically, general features of the "primary" sequence specificity of DNA binding (the precise order of DNA base steps directly contacted by the ligand) have been inferred from solution experiments conducted with synthetic polynucleotides or various genomic DNAs with high and often unknown sequence complexities [cf132–134]. With few exceptions structural (crystallographic and NMR) investigations have been confined to the study of ligand interactions with extremely short duplexes [cf135,136]. In the last 15 years considerable efforts have generated a large body of canonical information regarding "primary" sites (DNA sequences) where sequence specific interactions between binding ligands and DNA substrates are thought to occur. However, more subtle and potentially much more intriguing are features of DNA/ligand interactions where sequence specific ligands can deform or otherwise affect DNA substrate reactivity in adjacent unbound DNA sequences outside the primary binding site. Such secondary ligand binding effects have been generically referred to as "context" effects and are frequently observed indirectly as (for example) the ubiquitous influences of different flanking sequences on restriction enzyme cleavage rates [cf137].

Explanations of ligand binding behavior which explicitly included some form of secondary effect attributable to DNA substrates were initially popularized by Wells, Wartell and colleagues about 20 years ago [138–140] but have received little attention since then. This is probably not so much because such effects are not acknowledged to exist but because each specific ligand under study displays a different mode of interaction (binding site size, binding constant, etc.) that makes it difficult to discern any general rules for suspected secondary sequence effects on binding. In fact, most analytical methods for characterizing generic specificity of DNA binding ligands must incorporate at least one cooperativity parameter to reasonably model experimentally obtained non-linear binding isotherms [141,142].

From the simplest perspective it seems that a complete explanation of the binding of any ligand to DNA should include an absolute minimum of four energetic contributions. These are: (1) Interactions of the ligand with itself, both in the absence and presence of DNA site specific binding including possible rearrangements of the ligand structure induced by DNA binding; (2) Sequence specific interactions of the binding ligand with primary binding sites on the DNA substrate; (3) Non-sequence specific ligand/DNA interactions between ligand and DNA substrate, as exemplified by linear diffusion models [143]; and (4) Contributions from dynamic and equilibrium alterations of DNA sequences directly adjacent to, but distinct from the primary ligand contact sites. The number of features actually necessary to sufficiently describe the binding process of a particular ligand can be reduced by conducting appropriate experiments with a particular ligand. Experimental conditions can be designed such that certain contributions can be eliminated because their affect on the overall binding equilibrium is small.

The past 10 years have seen gradual adoption of recombinant DNA and sequencing technologies by researchers interested in studying how a given ligand recognizes its primary DNA binding site(s). This has led to a large number of new strategies for investigating sequence-dependent ligand interactions. In contrast to the historical use of relatively poorly characterized DNA substrates, more recent strategies have routinely utilized restriction fragments of known sequence to evaluate relative binding specificities exhibited by a given ligand at bp resolution. The advantage of this approach is that a multitude of potential DNA binding sites can be investigated simultaneously. To a large extent the strategies that have emerged are variations of "footprinting" or protection methods [144]. These approaches rapidly lead to utilization of DNA oligomers with sequences containing the preferred ligand interaction sites identified in experiments on heterogeneous sequence restriction fragments. With these refined synthetic substrates, precise details of primary DNA/ligand interactions have been investigated.

The aforementioned approach relies on design, synthesis and targeted examination of more "relevant" DNA sequences. These sequences display relatively higher binding preferences for the ligand compared to the variety of other DNA sequences present in the sequence environment of the restriction fragment. Such model studies can significantly illuminate features of binding interactions at the atomic level. This approach is especially useful when the ligands are regulatory proteins because both genetic and biochemical evidence can be employed to demonstrate that the investigated binding site has biological relevance. However, ligand binding sites identified on random DNA restriction fragments as "relevant" may provide little insight into even the primary in vitro "specificity" of small ligands, such as antitumor drugs, because independent verification of the relative importance of given sites of interaction in vivo for these agents is not available. In cases of such indiscriminating DNA binding ligands even in vitro results should be viewed with caution.

Three principal factors form the basis for this caution. First, in all studies of sequence preference using natural DNA substrates whose sequences are known (restriction fragments), the actual sequences employed do not adequately approximate the statistical population of DNA sequences that potentially could be bound by the ligand. To illustrate this point consider a hypothetical DNA binding ligand with an absolute binding preference for the particular two base DNA sequence, 5'-GpC-3'. In the nearest-neighbor exclusion approximation, neighboring bps on either side of the two bp primary recognition sequence would be expected to affect the ligand binding constant for its site [145]. This leads to 16 possible four bp sequences that contain a centrally located 5'-GpC-3' dinucleotide sequence. In principle each of these tetramers could have a different binding constant for the ligand. In a random DNA sequence, any given tetramer would occur once every 256 bps. Assuming Poisson statistics and a completely random DNA sequence, 256 bps of DNA would be required to examine just 70% of the total potential pool of tetramer binding sites. In practice little attention has been paid to this issue.

A second complicating factor for ligand binding studies is difficulty of determining ligand stoichiometry for many DNA sequences. For any equilibrium process, assessment of binding stoichiometry is inherently difficult. In the case of a lattice of potential binding sites (which can be overlapping and nonunique), stoichiometry determination is further complicated For example, if binding to a single GC site influences binding at a second GC site directly adjacent to the first (cooperativity), then a sequence such as 5'-GCGC-3' could appear to be a "better" or "worse" binding site for the ligand based solely on an assumed stoichiometry. Such difficulties arise because the molecular techniques used are rarely of high enough sequence resolution to accurately determine stoichiometry by footprint or protection size alone. This was precisely the situation in a study of actinomycin D binding to a 5'-GCGC-3' sequence motif embedded within a restriction fragment [146]. Subsequent NMR experiments by another group demonstrated that two actinomycin D molecules can bind to this sequence in a cooperative fashion [147,148].

The third complicating factor for DNA ligand binding studies, particularly those that utilize DNA sequencing methodologies, is that a thorough understanding of the assay system is often difficult to obtain. Complications arise from the fact that DNA binding ligands, including footprinting reagents themselves, can bind to virtually any DNA sequence in "non-specific" fashion. Thus, not only the ligand under study but also the ligand used to probe the interaction must be considered.

An exhaustive literature relating to various aspects of the primary interactions of ligands with DNA or specific DNA structures (or classes of DNA structures) is not given here. For detailed reviews of these topics such as the effects of binding dependent ligand rearrangements, ligand/ligand interactions or linear diffusion on ligand/DNA interactions the reader is referred to the many excellent treatises that have appeared in recent years [cf149–154]. The discussion here focuses on DNAse I footprinting methodology and what such experiments can reveal about secondary ligand binding effects. The experimental approach and some of its shortcomings are described next.

B. DNAse I Footprinting and its Use to Estimate Primary Ligand Binding Preferences and Detect Secondary Ligand Binding Effects The term "footprinting" was first applied to describe differences in partial digestion patterns of restriction fragment DNAs exposed to the ubiquitous DNA cutter DNAse I in the presence and absence of a binding ligand [155]. Footprinting provides an elegant and relatively simple means for identifying DNA sequences specifically bound by ligands. Quantitative applications of this procedure (and its variations) to assess protein/DNA interactions were recently reviewed [144]. Of the newer sequencing methodologies available for characterization of ligand/DNA binding, footprinting techniques are the most widely used. In a classical DNAse I footprinting experiment end-labeled duplex DNA is first incubated with the ligand to be probed and then subjected to partial digestion by DNAse I. DNA digestion products obtained from separate reactions conducted in the presence and absence of ligand are then run in adjacent lanes of a denaturing polyacrylamide gel. After electrophoresis each lane contains a "ladder" of products. When the lane containing DNA plus ligand is compared to the lane with DNA alone, an interrupted ladder pattern results because the site where the ligand binds is sterically blocked from accessibility to the enzyme. Of equal significance, it is often observed that some DNA product bands appear easier for the enzyme to cleave at DNA sites adjacent to the primary binding site. In fact, many ligands frequently display dramatic DNAse I rate enhancements at secondary sites distant from where the ligand specifically binds. Rate enhancements at secondary sites have also been observed in experiments with footprinting agents other than DNAse I [144]. Interpretation of the underlying cause for these enhanced secondary cleavage sites has created some controversy [156]. As will be described subsequently, provided appropriate attention is given to the experimental design of footprinting experiments, sequence specific enhancements that occur in sequences flanking the primary ligand binding site can be attributed to secondary or "context" effects.

In principle, quantitative information regarding sequence specific ligand binding can be obtained from footprinting methods. From analysis of these experiments, thermodynamics of the interactions of a particular ligand with specific DNA sequences can be evaluated. Such information can provide deeper insight into the origins of sequence dependent specificity. Conceivably, such information could aid in de novo design of new ligands that display even higher sequence specificity. In order to obtain reliable quantitative results from footprinting experiments, several subtle features of footprinting reactions must be considered. These are described subsequently.

By definition, footprinting is a competition assay; both the DNA footprinting (cleaving, modifying) reagent and the binding ligand compete for the same DNA sequence(s). If the ligand is bound at a given DNA sequence then the cleaving agent cannot make a cut and a footprint is generated. Alternatively, if the cleaving agent completely outcompetes the ligand for a particular sequence, no footprint is produced. For this reason, an implicit assumption in any quantitative footprinting experiment must be that the binding constant of the ligand/substrate complex far exceeds that of the cleaving agent/substrate complex. In practice, to ensure this requirement is met at some point, the concentration of the ligand under study is increased until a specific footprint is observed. In this case, ligand binding is driven by the ligand concentration. From this procedure qualitative rankings of which sequences, of those available in the reaction mixture, are bound most efficaciously by the ligand can be obtained.

The quantitative analysis of footprinting experiments can be quite complex depending on the ligand under study. In any quantitative footprinting experiment the binding constants of both the cleaving (or modifying) footprinting reagent and ligand for a specific DNA sequence will make some contribution (even if small enough to ignore) to the measured thermodynamic binding data. With this realization two operational classes of DNA ligands can be delineated. First, there are ligands that display DNA binding affinities that are (under conditions of a given experiment) orders of magnitude greater than the footprinting reagent. In these cases, because competition between the footprinting reagent and the ligand measurably influences the ligand binding constant, quantitative analysis of the binding data is straightforward. Since the DNA site concentration is known and the total ligand concentration is known, the free ligand concentration in the footprinting experiment can be explicitly calculated ($L_{free}=L_{total}-L_{bound}$; $L_{bound}=DNA_{bound}$) and used to determine the binding constant. Clearly, it is critical that the binding stoichiometry of the ligand at the primary binding site be known (assumed to be 1:1 in the above) so accurate estimates of the free ligand concentration can be made. This type of system (with known stoichiometry) has been exploited by Ackers and colleagues in their studies of lambda repressor/operator interactions [157,158] and by Ptashne and co-workers [159–161].

The second class of ligands are those that bind with affinities comparable to the footprinting reagent. For relatively complex DNA sequences such as restriction fragments, extraction of the true binding constant for this type of ligand at a given DNA sequence is a more arduous task. These ligands (examples are antibiotics and antitumor agents) generally display specificity for many DNA sites, making it virtually impossible to accurately determine free ligand concentrations by the site bound method (described above). Accurate determination of the free-ligand concentration would require simultaneous determination of the extent of binding to all bps in the restriction fragment, as well as the stoichiometries at all possible bound positions at any given point in a titration. In addition, a practical difficulty exists in measuring x-ray film band intensities for all DNAse I cleaved positions in a restriction fragment. The "ladder" of products becomes compressed toward the top of a DNA sequencing gel making it difficult to ascertain the amount of full length material remaining. A strategy for overcoming the difficulty of measuring free ligand concentration was presented and experiments testing its utility have been implemented [162]. This procedure allows calculation of free ligand concentrations independent of the degree of protection displayed by a restriction fragment. In this scheme a vast excess of unlabelled "carrier" DNA oligomer containing a single site for the ligand is also placed in the reaction mixture. If the fraction of ligand bound to this oligomer is known over the entire concentration range of the ligand used in the footprinting experiment, and the oligomer concentration is in vast excess over the labelled restriction fragment, the free ligand concentration at all points in the titration is explicitly known. Thus, ligand binding constants for sites on the restriction fragment can be determined. In one study using this procedure ligand binding was ascertained from the degree of observed protection from DNAse I of the same labelled and unlabelled DNA oligomer substrates. However, this study met with criticism because of the shape of resultant binding isotherms [163]. This criticism is probably valid because potential competition between DNAse I and the ligand for binding sites was not explicitly considered. Even so, it is not yet clear that other factors (such as incorrectly assumed stoichiometry at high ligand concentration) were perhaps also responsible for observed discrepancies from theoretically predicted isotherm shapes.

To add further confusion to the process of quantitative evaluation of ligand binding constants for restriction fragments using footprinting methods, it was recently asserted that the extent of protection from probe cleavage observed in any footprinting experiment (regardless of ligand binding constant) is not proportional to the extent of ligand binding [163–169]. It was argued that when ligand binds in the presence of a footprinting probe, such as DNAse I, that the probe is displaced from DNA by the ligand. This displaced probe is then free to cleave at DNA sites not bound by the ligand. This explanation has been presented to account for the aforementioned relatively common observations of ligand dependent DNAse I enhancements. In this model, because of the higher free enzyme concentration, the ligand displaced probe reacts more with all DNA sequences than in the ligand free controls. This in turn results in DNAase I enhancements at unbound sites proportional to the total amount of ligand bound DNA. This argument apparently neatly explains DNAse I enhancements as artifacts of footprinting methodology. From this logical stand point, unsubstantiated by any published kinetic data, these authors have also argued that a correction factor should be used to account for the displaced probe effect at ligand bound sites. It was proposed that the observed extent of protection at a given point in the titration should be reduced by a factor corresponding to the number and extent of total sites blocked by the ligand. Experimental results from other groups have explicitly refuted the above explanation as the source of at least some reported DNAse I enhancements [101,104]. In short, no experimental evidence exists to support the use of kinetic order corrections of observed binding extent in determination of binding constants from quantitative footprinting experiments.

Before presenting DNAse I enhancements as secondary ligand binding effects more clarification is required. To understand the causes of DNAse I enhancements one must first examine the kinetic order of the DNAse I reaction in a typical experiment. DNAse I is known to display a typical hyperbolic substrate dependence with respect to single strand cleavage [102,103]. In fact, this enzyme was once used to indirectly support the existence of DNA double helical structure by the lack of observed hyperbolic behavior when reacted with double stranded DNA [170]. Hyperbolic single strand nicking activity suggests that at a given substrate:enzyme ratio the kinetics of DNA nicking fall somewhere between the limits of first order (binding limited/unsaturated enzyme) and zero order (catalysis limited/saturated enzyme). Depending on kinetics of the digestion reaction in the absence of added ligand (the control lane in the footprinting reaction) vastly different types of behavior of the enzyme kinetics would be expected when the ligand is added. In the limiting case of saturated enzyme, total DNA nicking by the nuclease would be expected to be relatively invariant to reduction of substrate concentration caused by bound ligand. This situation would lead to the model of Dabrowiak and co-workers [163–169] described above, where enhancements would arise by virtue of simple reduction in free substrate DNA concentration as a function of added ligand. Conversely, in the limit of first order kinetics a reduction in substrate would be expected to lead to a proportionate reduction in total observed cleavage [171]. It is under this latter situation that the measurements discussed in the next sub-section were made. From one perspective, reported DNAse I enhancements described below are not a result of altered kinetics due to the ligand [171]. More recently, Fox and colleagues [104] provided information sufficient to infer that similar conditions prevailed in their DNAse I footprinting experiments. They also asserted that DNAse I enhancements are not due to a kinetic effect in their system.

In summary, footprinting reactions can be extremely helpful in qualitatively locating ligand binding positions. The methodology can provide quantitative binding data for ligands that display high binding affinities for their DNA sites. However, for ligands with lower binding constants approaching those of the footprinting probe employed, additional factors must be considered before reliable binding constants can be obtained.

C. Sequence Context Effects in the Binding of Actinomycin D

The potential for bound ligands to affect reactivity of unbound flanking DNA sequences has been recognized for some time. In the case of studies of DNAse I footprinting studies of actinomycin D, binding locations can be identified by lack of DNAse I cleavage within the drug binding sites due to inaccessibility of the DNA where the drug binds [172–173]. Enhanced rates of DNAse I cleavage at sequences immediately flanking the drug binding site are also frequently encountered in these experiments. A combination of imino proton NMR and DNAse I attack experiments of $(AT)_n AGCT(AT)_n$ sequences bound by actinomycin D revealed that specific cleavage enhancements at distant sites, associated with binding of actinomycin D to the tetrameric core sequence 5'-AGCT-3', corresponded to propagated structural changes induced by the bound drug [101,174]. In contrast, under identical conditions, the hexadecamer sequence motif $(AA)_3 AGCT(TT)_3$ (SEQ ID NO: 2) showed no enzymatic rate enhancements in flanking DNA associated with actinomycin D binding. These results suggested perturbations seen in the $(AT)_3$ (SEQ ID NO: 1) flanking sequences are apparently not propagated in the $(AA)_3$ (SEQ ID NO: 2) flanking sequence motif. A summary of these experimental results is depicted in FIG. 6.

Additional evidence that DNAse I detected enhancements in flanking sequences correspond to structural perturbations was also obtained from proton NMR experiments of d[(AA(AT)$_2$AGCT(AT)$_2$TT] (SEQ ID NO: 5) (AA(AT)$_2$ in FIG. 3) complexed with actinomycin D [175]. Changes in chemical shifts in flanking DNA sequences induced by actinomycin D appeared to be dispersed over several bps and not localized to specific base stacks. A summary of this data is displayed in FIG. 7. Taking these chemical shift changes to correspond to structural perturbations it would appear from the data in FIG. 7 that propagated structural effects are greater in unbound regions 3' to the drug intercalation site on both DNA strands. Coincidentally, these same regions correspond to sites of drug associated DNAse I cleavage enhancements.

In summary, oligonucleotide studies with actinomycin D have demonstrated that this ligand when bound at the center of a 16 bp DNA fragment can influence reactivity of a second ligand (DNAse I) at distances of at least five bps (half a helical turn) away [175]. From results of footprinting experiments of actinomycin D bound to AGCT sites embedded in different flanking sequences of plasmid DNAs, Fox and colleagues [104] independently arrived at a similar conclusion. Therefore, the sequence specific data described above reveals that such effects are more transmittable in $d(AT)_n$ sequences than in $d(AA)_n$ sequences. From this point of view two logical questions arise. (1) Are such effects unidirectional, i.e. do flanking sequences likewise transmit effects back to the actinomycin D binding site in the center? (2) If actinomycin D is capable of discriminating between two sequence isomers, is this a general property of all DNA binding ligands or a characteristic unique only to actinomycin D? These questions are addressed next.

D. Effect of Non-Contacted Flanking DNA Sequence on Rates of Cleavage by Restriction Enzymes-Overview Restriction enzymes cleave duplex DNA at specific nucleotide sequences. Numerous studies have demonstrated that sequences or structures flanking a restriction enzyme recognition site can influence the rate of restriction enzyme cleavage at the site. Goldstein et al., were the first to encounter such effects when cleaving P4 phage DNA with the restriction enzyme EcoRI [176]. Even though at the time of the observation the sequence of the lambda phage genome had not been determined, these authors suggested that differences in DNA sequences flanking EcoRI sites were likely the reason for observed differences in cleavage rates. Since their initial report, a large body of data regarding the sequence dependence of various restriction enzymes has appeared [177,178]. Study of cleavage rate variations for the enzymes EcoRI, Hinf I and Pst I demonstrated that the activities of all three enzymes could be inhibited by long runs of GC rich sequences placed immediately flanking the restriction sites. A more recent study of the effects of flanking DNA sequence on cleavage by enzymes Fnu DII, Hae III, Hha I and Msp I was reported by Drew and Travers [179]. They noted from the dependence of cleavage rates of these enzymes, at sites surrounded by different sequences, that the dependence on flanking sequence "though clearly evident, was complex and varied".

Variations in rates of restriction enzyme cleavage have also been shown to depend on DNA substrate length [180, 181. Facilitated diffusion of enzymes along the DNA contour was proposed as a mechanism used by proteins for locating sequences comprising their binding sites. In this case, the rate of cleavage at a specific site would directly depend on the length of the DNA flanking the specific site [180,181]. Enhancements in restriction enzyme cleavage rates with increases in the length of sequences flanking the restriction sites have been observed and found to be greatest at relatively low ionic strength [182–184]. To successfully evaluate effects of flanking sequences on reactivity of a given restriction enzyme at a specific DNA site it is therefore mandatory that the DNA substrates employed include controls for both length and nucleotide composition.

It was reasoned that if actinomycin D was capable of discriminating between $(AT)_n AGCT(TA)_n$ and $(AA)_n AGCT(TT)_n$ sequences (evidenced by the presence of DNAse I cleavage enhancements in the former but not the latter sequences), Alu I, a restriction enzyme which cleaves at the tetranucleotide sequence 5'-AGCT-3' might also be able to discriminate between these two families of sequences. In the next sub-section results of measurements of first strand cleavage rates by Alu I restriction enzyme, which recognizes and cleaves at the central tetramer sequence of the seven DNAs in FIG. 3, are presented. These results reveal that Alu I is sensitive to both identity and length of flanking sequence motifs.

E. Effect of Flanking Sequence Identity ("Context") and Length on First Strand Cleavage Rates by Alu I Restriction Enzyme Rates of first strand cleavage by Alu I restriction enzyme were measured for the DNAs shown in FIG. 3. To determine relative rates of Alu I first strand cleavage for the duplexes in a manner facilitating quantitative comparison of the rates produced, it was critical to ensure that all duplexes were cleaved under identical enzyme and substrate concentrations. To obtain these conditions pilot experiments were performed with all duplexes to establish enzyme concentrations and incubation times which could be universally applied to the entire set of molecules. A fairly high concentration of the fastest cleaving duplex found in the set, $(AT)_2$ (SEQ ID NO: 3), was employed as a competitor for the enzyme (13 μM duplex). It was reasoned that these conditions would produce unsaturated enzyme kinetics resulting in a first order initial (first) strand cleavage regime. The labeled duplex concentration was 95±15 nM. Labelled duplexes were pre-annealed and no hairpins were detected by native polyacrylamide gels. Reactions were performed for varying lengths of time, but never exceeding the time where more than 50% of total substrate was cleaved. Rate measurements for each duplex were repeated at least twice, and each independent rate measurement employed independently labelled duplex. The fraction of duplex remaining as full length was determined after separation of cleaved product from full length strands on 7.0 M urea polyacrylamide gels by autoradiography. Full length molecules remaining were excised from the gel and analyzed by direct Cherenkov counting. Consequently, each time point represents the average fraction remaining (relative to control experiments with no enzyme, executed in parallel) determined from at least two independent cleavage experiments.

Alu I restriction enzyme was obtained from a commercial supplier (Bethesda Research Laboratories, Gaithersburg, Md.). Enzyme stability was established by "spiking" test reactions with labelled duplex DNA halfway through a mock digestion containing carrier duplex but no label. No loss of activity was detected over the time intervals employed at the high duplex and enzyme concentrations used (128 units per reaction in a reaction buffer composed of 8 mM $MgCl_2$, 2 mM $CaCl_2$, 100 mM NaCl, 0.66 μg/μL BSA, 10 mM Tris-HCl, pH =7.5). This methodology also provided an indirect test of the DNA concentration invariance of the rates obtained. Final glycerol concentration introduced with the commercial restriction enzyme was constant in all reactions at 16%.

Results of the rate measurements are shown in FIG. 8. Seven plots of the fraction of total molecule uncleaved versus time, $f_c(t)$, are shown corresponding to the seven duplexes examined. Reactions were allowed to proceed only to a point where at least 50% of the respective duplexes remained uncleaved. This allowed reliable initial velocities to be obtained. By this method a linear response of $f_c(t)$ versus time would be expected regardless of the actual kinetic order governing the digestion reaction (i.e. zero or first order, unsaturated or saturated enzyme, respectively). The first order behavior of all the digestion reactions is demonstrated by inspection of the rate data shown in FIG. 8. For example, examination of the rate data for $(AT)_2$ (SEQ ID NO: 3) (upper left panel of FIG. 8) reveals that just over 50% of this molecule remains uncleaved after 30 minutes, while the most resistant duplex, $(AA)_4$ (SEQ ID NO: 7) (lower right panel), has more than 75% uncleaved molecules remaining after 70 minutes. Since $(AT)_2$ (SEQ ID NO: 3) was present in vast (>100 fold), but identical excess in all reactions, the rate of cleavage of (AA)$_4$ (SEQ ID NO: 7) (for example) was linear with time despite significant reduction in total available substrate. In other words, the same rate constant is independently obtained from either the first four or last four rate data points for this molecule. This condition can occur only when the enzyme is present in excess and the reactions closely approximate first order kinetics. Thus, in these experiments the observed rate of first strand cleavage is dominated by formation of the enzyme/DNA substrate complex and not subsequent reaction steps. Rate constants were determined by linear least squares fits to the $f_c$(t) versus time data. The linear fits are shown for all seven duplexes. Rates obtained from the slopes in FIG. 8 are listed in Table 6 along with correlation coefficients of the linear fits. Note, R values in no case are lower than 0.95 indicating that the precision of the data obtained by the method employed is reasonably good.

In FIG. 9, the observed rate constants for first strand cleavage, $k_{obs}$, are plotted versus duplex length. $k_{obs}$ is the observed relative rate of enzyme first strand cleavage of the duplexes under first order kinetic conditions. Several interesting features emerge from these plots that demonstrate the Influence of duplex length and flanking sequence identity on Alu I first strand cleavage rates of these DNAs. First strand cleavage rate is inversely proportional to duplex length. Comparison of the rate data in FIG. 9 demonstrates that the 12-mers (in each series, i.e. (AT)$_n$ or (AA)$_n$) are cleaved at approximately 2.0 and 1.6 times faster than the 20-mer and 16-mer of the same series, respectively. Thus, increasing length (65% increase between 12 bp and 20 bp) does not result in increased rate of first strand cleavage by the enzyme. This is contrary to what would be expected for an enzyme diffusion mechanism [180,181]. Apparently, such a mechanism is not rate determining in these measurements. This is perhaps not surprising since the ionic strength of the solvent was such as to minimize a diffusion mechanism. Also, for DNAs of the same length Alu I first strand cleavage rates are consistently a factor of three times higher for the (AT)$_n$ molecules than for the (AA)$_n$ molecules i.e. $k_{obs}$(AT)$_2$/$k_{obs}$(AA)$_2$=3.02; $k_{obs}$(AT)$_3$/$k_{obs}$(AA)$_3$=2.95 and $k_{obs}$(AT)$_4$/$k_{obs}$(AA)$_4$=3.00. Finally, the "hybrid" 16 bp molecule, AA(AT)$_2$ (SEQ ID NO: 5), that contains a mixture of both AA and AT flanking sequences, cleaves at a rate intermediate between that of the 16 bp molecules containing purely AT or AA (TT) flanking sequence motifs.

F. Comparisons of Rates of Alu I First Strand Cleavage with Free-Energies of Duplex Melting The first strand cleavage rates evaluated for the seven duplexes in FIG. 3 are now compared to the melting free-energies of these molecules given in Table 4 of section II. Plots of $-RT\ln k_{obs}$ versus $\Delta G_D$ for the seven DNAs are shown in FIG. 10. Interestingly, lines can be drawn through the data that intersect at a single point. Interpretations of this observation are given below.

FIG. 10 reveals that small sequence dependent changes in DNA equilibrium stability result in relatively large increases in rates of initial enzyme digestion at specific sites. This immediately suggests stability changes apparently affect the height of the activation barrier for initial enzyme reactivity [175]. The extrapolations in FIG. 10 further suggest a linear relationship between the activation free-energy for Alu I first strand cleavage, $\Delta G^{++}$, of a particular length duplex DNA substrate and the free-energy of melting the duplex, $\Delta G_D$, i.e.

$$\Delta G^{++} = -RT\ln k_{obs} = \kappa(N)\Delta G_D + \Delta G^{++}(0) \tag{30}$$

That the plots in FIG. 10 are not parallel reveals the proportionality constant, $\kappa(N)$, must be length dependent as written in eqn (30). The point where all lines cross, ($\Delta G_D$(0),$-RT\ln k_{obs}$(0)), should correspond to the activation free-energy for cleavage of the hypothetical tetramer core sequence AGCT alone (no flanking sequence). As expected, this point actually corresponds to the predicted partial melting free-energy, $\Delta G_p$, of the four bp enzyme recognition sequence, AGCT. From the numbers in column C of Table 1 this value is calculated to be −5.2 kcal/mol.

The observed linear relationships between binding-limited enzyme cleavage rates and duplex melting free-energies immediately suggests duplex formation lies in the reaction pathway of enzyme binding. To more clearly visualize the enzyme/DNA reaction coordinate, consider the simple classical scheme,

$$S_1 + S_2 \overset{1/K_D}{\rightleftharpoons} D + E \overset{K_1}{\rightleftharpoons} E \cdot D \overset{k_c}{\to} \ldots \to E + P \tag{31}$$

where $S_1$ and $S_2$ are complementary single strands that associate to form the duplex DNA substrate, D. $K_D$ is the equilibrium constant for melting the duplex. E is the enzyme, E·D is the enzyme/DNA complex that forms with binding constant $K_1$. First strand cleavage is represented by the rate constant $k_c$. P is the final cleaved product produced after all rate steps subsequent to first strand cleavage. In the binding-limited case, as for the Alu I experiments described above, all reaction steps in the pathway subsequent to the initial (first strand) cleavage step can be ignored. Thus, the rate constant for the cleavage reaction, $k_{obs}$, is given by, $$k_{obs} = K_1 k_c \tag{32}$$

$K_1 = \exp(-\Delta G_1/RT)$ is the equilibrium constant for binding. $k_c = A_c \exp(\Delta G^{++}_c/RT)$ is the subsequent rate constant for first strand cleavage as defined above. The pre-exponential factor, $A_c = k_B T/h$, includes frequency and non-ideality factors associated with formation of the transition state. Since, the free-energy of binding is given by $\Delta G_1 = -RT\ln K_1$ and the activation free-energy is $\Delta G^{++} = -RT\ln k_{obs}$, eqn (30) becomes, $$\Delta G^{++} = \Delta G_1 + \Delta G^{++}_c - RT\ln A_c \tag{33}$$

This analysis is identical to that of Jen-Jacobson and co-workers [185–186] who analyzed kinetics of EcoRI cleavage of non-cognate sequences. Here the effects of flanking sequence on first strand cleavage is discussed. Comparison of the cleavage rates with free-energies of melting is made by equating eqns (33) and (30), $$\Delta G_1 + \Delta G^{++}_c - RT\ln A_c = \kappa(N)\Delta G_D + \Delta G^{++}(0) \tag{34}$$

Thus, $\kappa(N)$ is a unitless function of sequence length but not sequence composition. In the particular case given, $\kappa(N)$ relates the activation free-energy for enzyme reactivity to the free-energy of duplex melting.

It remains to be fully explained how binding of a duplex binding ligand, such as Alu I restriction enzyme, could be dependent on the stability of non-contacted bps in the vicinity of the binding site. From eqn (31) it is clear that all ligands which preferentially bind to DNA duplexes (as opposed to single strands) are in fact directly in the pathway of duplex formation. Consider the significant (first two) steps in the reaction in eqn (31). Because the substrate (duplex DNA) concentration is determined by the equilibrium between duplex and single strands, a classical case of a coupled equilibrium exists. A similar situation has been utilized to determine binding constants of DNA binding ligands (actinomycin D) from observation of the net elevation of $T_m$ in the presence of bound ligands [cf187,188]. A single binding site on a "short" DNA duplex the equilibrium binding constant can be written as a function of the duplex melting equilibrium, i.e.

$$K_1 = ([E \cdot D] K_D)/([S_1][S_2][E])  \quad (35)$$

An immediate consequence of eqn (35) is that the binding constant of a ligand is directly proportional to the melting equilibrium constant and thus inversely affected by stability of the flanking DNA. This is entirely consistent with results of the Alu I experiments described above. This can be seen from the plots in FIG. 10. The DNAs examined all contain the tetramer core sequence, 5'-AGCT-3' and all apparently have an identical intrinsic binding constant for this tetramer duplex. This is suggested by the common intersection point in FIG. 10. Therefore, the binding constant for the ligand apparently decreases with increased length and stability of the flanking sequence. Other flanking sequences that would result in alterations (increases or decreases) of the binding constants compared to those found for the specific flanking sequences examined can be found. Thus, when a second duplex with different flanking sequence is studied, the binding constant of the ligand for this sequence will be higher if this second duplex is less stable than the first duplex or lower if the opposite is true. The observed binding constant is composed of an intrinsic primary binding component and a flanking sequence secondary binding component. Consequently, for two sequences possessing the same binding site for a common ligand only the flanking sequence stability alters the binding constant. Again this is inferred from FIG. 10.

As a generalization from the Alu I experiments described above, consider two DNAs of the same length with different sequences subject to binding by the same enzyme. The binding constants for these reactions are designated $K_1$ and $K_1'$ with the appropriate primed quantities substituted in eqn (35). The following experimental conditions prevail; $[E] = \gg [E \cdot DNA]$, $[E]' \gg [E \cdot DNA]'$, $[E] = [E]'$ (vast excess of enzyme), $[S_1] = [S_1]'$, $[S_2] = [S_2]'$. First, considering only the binding step, the ratio of the binding constants, $K_1'$ and $K_1$ is, $$K_1'/K_1 = ([E \cdot D]' K_D')/([E \cdot D] K_D) \quad (36)$$

Now the ratio of the observed rate constants is given by, $$k_{obs}'/k_{obs} = ([E \cdot D]' K_D' k_c')/([E \cdot D] K_D k_c) \quad (37)$$

From eqns (34)–(37), $$k_{obs}'/k_{obs} = (K_D'/K_D)^\kappa \quad (38)$$

Thus, from eqns (37) and (38), $$\kappa = (ln([E \cdot D]' k_c'/[E \cdot D] k_c)/ln(K_D'/K_D)) + 1 \quad (39)$$

Invoking the same assumptions as Lesser et al. [185] and Hogan et al. [103] i.e. that binding of the enzyme and rearrangement of the enzyme/DNA complex toward the transition state configuration are coupled and energetically favored, the energy of the next rate step along the reaction coordinate, designated by $k_c$, is small compared to the enzyme/substrate complex free-energy. This assertion is not inconsistent with recent suggestions by Spolar and Record [189] that DNA binding proteins can, through hydrophobically driven structural rearrangements, provide substantial energetic contributions to the free-energy of forming a protein/DNA complex. Thus relative (initial) reactivity of an enzyme with the same binding site on different DNAs where the binding sites are flanked by different sequences, predominantly depends on the relative binding constants of the enzyme for the two different DNAs. The flanking sequences of the two DNAs constitute the only difference between the two sequences. Consequently, the energetic barriers to binding are exclusively dictated by flanking sequences. As given by eqn (38) the relative initial cleavage rates are related (through $\kappa$) to the equilibrium constants for melting, and thus inversely proportional to the ratio of the melting free-energies.

For Alu I, $\kappa(N)$ can be determined from values of the cleavage rates and duplex free-energies given in Tables 4 and 6, or from the slopes of the plots in FIG. 10. For any two sequences of the same length, $$\kappa(N) = RTln(k_{obs}'/k_{obs})/(\Delta G_D - \Delta G_D') \quad (40)$$

Recall the ratios of the rates for the $(AA)_n$ and $(AT)_n$ molecules $(k_{obs}'/k_{obs}) = 3$. From the data presented in Tables 4 and 6 for the 12 and 20 bp molecules, $\kappa(12) = 2.17$ and $\kappa(20) = 0.28$. For the three 16 bp molecules the $(k_{obs}'/k_{obs})$ ratios and $(\Delta G_D - \Delta G_D')$ differences in eqn (40) can be determined in three ways from any pair of values in the 16-mer set and yield, $\kappa(16) = 0.45 \pm 0.11$.

In summary, data have been presented that indicate for fragments of the same length, the rate of (initial) reactivity as determined from cleavage by Alu I restriction enzyme is inversely proportional to stability of the duplex. In the following section results of the interactions of another ligand, gilvocarcin V, with the $(AT)_3$ (SEQ ID NO: 1) and $(AA)_3$ (SEQ ID NO: 2) hexadecamers are presented. These results also demonstrate an inverse relationship between DNA stability and reactivity.

G. Qualitative Support for the Relationship Between Reactivity and Stability-Reactivity of Two 16 Base Pair DNAs In this sub-section results of studies of the reactivity of four ligands with two 16-mer substrates, $(AA)_3$ (SEQ ID NO: 2) and $(AT)_3$ (SEQ ID NO: 1), are presented. One of the ligands, gilvocarcin V, is little known and briefly described. Gilvocarcin V (toromycin, anandimycin or GV) is an antibiotic isolated from Streptomyces gilvotanareus that has antitumor activity [190]. Photoadduct formation of GV with oligonucleotides can be assayed by altered electrophoretic mobility of GV modified synthetic oligonucleotides. Previous studies have suggested the majority of light-induced GV/DNA adducts are formed at thymine residues, and cytosine residues are less reactive [191]. The relative rates of adduct formation (induced by uv light exposure) were determined for both hexadecamers under identical conditions. Results of these experiments are shown in FIG. 11. Note, the thermodynamically less stable duplex, $(AT)_3$ (SEQ ID NO: 1) is at least 2.5 times more reactive than $(AA)_3$ (SEQ ID NO: 2). Even though no attempt was made to quantify the observed differences in equilibrium binding preference of this drug, the observed rates of reaction correspond well to differences in the relative stabilities of the two DNAs.

Results of the relative reactivities of four ligands; actinomycin D, gilvocarcin V, DNAse I and Alu I with the 16-mer duplex sequences $(AT)_3$ (SEQ ID NO: 1) and $(AA)_3$ (SEQ ID NO: 2) of FIG. 3 are summarized in Table 7. Actinomycin D and gilvocarcin V are minor groove intercalating compounds. DNAse I is a minor groove relatively ubiquitous, cleaving endonuclease (although see [192]). Alu I is a major groove site specific endonuclease. This summary reveals, at least for the sequence isomers examined, that DNA reactivity is determined by the DNA sequence, independent of the particular mode of ligand binding.

IV. Perspective
A. Other Studies

The kinetic analysis described in the previous section is not unprecedented. To demonstrate,briefly a recent kinetic approach used to study interactions of EcoRI enzyme with variants of its cognate six bp recognition sequence, 5'-GAATTC-3' is reviewed. The crystal structure of the DNA/enzyme complex was presented some time ago [193, 194] and indicated the bound (uncleaved) DNA was distorted or "kinked" in the complex.

Two groups have recently reported analysis of EcoRI cleavage reactions at bp substituted non-cognate sites (185, 186,195]. Despite the use of a sophisticated kinetic model by Thielking et al. [195], similar lines of reasoning and experimental designs were followed in both studies. Jen-Jacobson and co-workers [185,186] approached the problem in a manner identical to that described for Alu I in the previous section, i.e. cleavage reactions were studied only until the first bond-breaking step occurred. In this scheme, energetic contributions from subsequent kinetic steps in the cleavage reaction are negligible. Analogous to that depicted in eqn (31), the reactions for first irreversible bond breaking step, designated by $k_c$, can be written as [185],

$$E + DNA \underset{}{\overset{K_A}{\rightleftharpoons}} E \cdot DNA \overset{k_c}{-->} [E \cdot DNA]^{++} \quad (41)$$

$K_A$ is the equilibrium constant for binding and $k_c$ is the rate constant for first bond cleavage producing the bound, cleaved species, $[E \cdot DNA]^{++}$. $\Delta G^0_{ED} = -RT \ln K_A$ is the standard free-energy of formation for the enzyme/substrate complex and $\Delta G^{0++} = -RT(\ln k_c - \ln A)$ is the standard free-energy of activation for the first bond breaking step. As described above, the pre-exponential factor, $A = k_B T/h$, includes frequency and non-ideality factors associated with formation of the transition state. The free-energy of forming the transition state, $\Delta G_f^{0++} = \Delta G^0_{ED} + \Delta G^{0++}$, includes both the energy of complex formation and first phosphodiester bond cleavage. The overall probability of first bond cleavage was given by $K_A \cdot k_c = \exp(-\Delta G_f^{0++}/RT)$. It was noted that although the product $K_A \cdot k_c$ is analogous to the familiar quantity $k_{cat}/K_m$ from classical Michaelis-Menten analysis, it avoids two difficulties associated with the Michaelis-Menten scheme [185]. First, $k_{cat}$ in Michaelis-Menten analysis is the catalytic constant for the entire reaction and may reflect rate limiting steps after initial bond cleavage (i.e. second strand recognition and cleavage reactions [cf195]). Second, Km is not a true equilibrium constant for binding of the enzyme to DNA. Characterizing cleavage reactions by $K_A \cdot k_c$ instead of $k_{cat}/K_m$ avoids these difficulties and a thermodynamic comparison of different non-cognate cleavage sites in terms of initial cleavage rates only is possible. This analytical approach is identical to defining the flanking sequence specific reactivity of DNA with Alu I presented in the previous section, where $k_{obs}$ (eqn 32) is analogous to $K_A \cdot k_c$. The difference between the two investigations lies in the sequence effects examined. In the case of the Alu I experiments described in the previous section, effects of different flanking sequences on cleavage at the same cognate Alu I site were investigated. In the EcoRI experiments, effects of sequence changes within the binding site, to so-called non-cognate sites, on first strand cleavage were investigated. Thus, reactions of Alu I with cognate sites and EcoRI with non-cognate sites can be analyzed in a similar manner provided appropriate experimental conditions pre-vail. The relative rates of EcoRI cleavage at cognate sites with different flanking sequences remain to be investigated in detail.

B. Conclusions

The notions that have been presented relating duplex stability and duplex reactivity provide an additional component that must be considered when describing ligand/DNA interactions. A general result from the ligand binding and thermodynamic data have been presented here that DNA binding ligands react more efficiently with less stable DNA duplexes. In the case of reactions of actinomycin D, DNAse I, Alu I and gilvocarcin V with two well defined short DNA duplexes, indisputable support for this notion was obtained. It was concluded that a direct relationship exists between primary binding specificity (dictated by a sequence of recognized bases that comprise the primary site), and flanking sequences. Supposing primary recognition and binding comprise the predominant energetic contributions for sequence specific interactions, the observed affinity of a ligand for a specific primary sequence should only be modulated by the free-energy of the flanking sequences. If so, it should be possible to estimate the degree of binding modulation of any ligand by examination of the flanking sequence. Because the extent of secondary sequence modulation would likely depend on the variety of free-energies possible from the composition and arrangement of the flanking sequences, it is not yet possible to predict secondary sequence modulation. However, effects of certain specific sequences can be ascertained from an empirical data set collected for several well defined DNA sequences and a given ligand. In any experiment, the extent of secondary modulation must be of a magnitude sufficient to produce a measurable change in primary binding affinity. Consequently, if the primary ligand binding constant is overwhelmingly dominant, modulation by flanking sequences would be expected to be small. On the contrary, data available for many ligands, such as restriction enzymes, reveals the primary sequence or intrinsic binding constant is small enough so that measurable modulation actually occurs. In the experiments described here, conducted under binding limited conditions, a constant ratio of Alu I cleavage rates was observed for flanking sequences having two different AT stacking patterns. This ratio was independent of duplex substrate length from 12 to 20 bps.

In summary, there are three major results of this study. (1) The primary binding constant of a DNA binding ligand can have a low enough magnitude that differences in stacking free-energies can effectively modulate reactivity. (2) Differences in stacking free-energy between two types of sequences remain constant when normalized for total length. (3) Contributions of the stacking free-energy of a DNA substrate to the observed rate modulation are independent of the distance from the cleavage site for the Alu I restriction enzyme, over the range of size examined (four to eight bps). Point (1) was demonstrated by the rate data, where a difference in first strand cleavage rate was observed for different flanking sequences of the same length and sequence composition. Point (2) was verified by calculation and measurement of the stacking free-energies for the entire set of duplexes examined. Point (3) is counter-intuitive. It seems logical that any model for binding site modulation by flanking sequences should include a distance dependence. That is, a ligand's relative binding affinity for two different sequences containing the same binding site, but differing at a single base residue in the flanking sequences, should be more greatly affected the closer the bp change is to the primary binding site. As demonstrated by comparison of the Alu I cleavage rates of the 16 bp isomers, this is not the case. Within experimental resolution, adding AA stacks to the end of the duplexes has the same effect as adding AA stacks closer to the Alu I site. Failure to observe a distance dependence immediately suggests the molecules examined are not of sufficient length to allow detection of the suspected distance effects. In this sense the results do not provide a determination of the length or "window" of DNA sequence over which Alu I cleavage is measurably modulated. Even so, results do reveal that this distance can be at least eight bps.

Finally, this work provides an interesting alternative insight into ligand DNA interactions. That is, any ligand that prefers duplex DNA over single strand DNA (or vice versa), whether the duplex is distorted or in single strand form, will lie in the DNA helix-coil transition pathway. This statement is true regardless of whether equilibrium constants or initial rates of ligand/duplex reactions are examined. This means sequence context effects must dictate the relative reactivity of a ligand for a given site on any form of DNA. More formally stated, the chemical potential of a free ligand that binds to DNA is energetically coupled to the actual state (duplex or single strand) in which the DNA resides when encountered by the ligand. In essence, observed changes in DNA structure that accompany ligand binding directly depend on which of the possible configurational states along the duplex to single strand transition coordinate that most resemble the state of the DNA when bound by the ligand.

TABLE 1

NON-UNIQUE NEAREST-NEIGHBOR FREE-ENERGIES $-\Delta G_{MN}$, 25° C. (cal/mol)

| 5'MN3' STACK | A (1.0M Na$^+$) | B (0.075M Na$^+$) | C (0.115M Na$^+$) |
|---|---|---|---|
| AT | 1474 | 1139 | 1092 |
| TA | 961 | 778 | 966 |
| AA (TT) | 1944 | 966 | 1195 |
| AC (GT) | 1342 | 1981 | 1764 |
| CA (TG) | 1954 | 1086 | 1509 |
| TC (GA) | 1575 | 1602 | 1802 |
| CT (AG) | 1599 | 1280 | 1280 |
| CG | 3611 | 1584 | 1887 |
| GC | 3139 | 2732 | 2674 |
| GG (CC) | 3069 | 1850 | 1908 |

A: Breslauer et al. (1986)
B: Delcourt and Blake (1991)
C: Doktycz et al. (1992)

TABLE 2

UNIQUE COMBINATIONS OF NEAREST-NEIGHBOR FREE-ENERGIES

| NEAREST-NEIGHBOR COMBINATION | $-\Delta G_x$, 25° C. (cal/mol) | | |
|---|---|---|---|
| | A (1.0M Na$^+$) | B (0.075M Na$^+$) | C (0.115M Na$^+$) |
| $\Delta G_1 = \Delta G_{AA(TT)}$ | 1944 | 966 | 1195 |
| $\Delta G_2 = \Delta G_{GG(CC)}$ | 3069 | 1850 | 1908 |
| $\Delta G_3 = (\Delta G_{AT} + \Delta G_{TA})/2$ | 1218 | 959 | 1029 |
| $\Delta G_4 = (\Delta G_{CG} + \Delta G_{GC})/2$ | 3375 | 2158 | 2281 |
| $\Delta G_5 = (\Delta G_{AC(GT)} + \Delta G_{CA(TG)})/2$ | 1648 | 1534 | 1637 |
| $\Delta G_6 = (\Delta G_{AG(CT)} + \Delta G_{GA(TC)})/2$ | 1587 | 1441 | 1541 |
| $\Delta G_7 = (\Delta G_{AT} - \Delta G_{TA} + \Delta G_{CG} - \Delta G_{GC})/12 + (\Delta G_{GA(TC)} - \Delta G_{AG(CT)})/6$ | 74 | 46 | 32 |
| $\Delta G_8 = (\Delta G_{AT} - \Delta G_{TA} - \Delta G_{CG} + \Delta G_{GC})/12 + (\Delta G_{CA(TG)} - \Delta G_{AC(GT)})/6$ | 105 | 23 | 34 |

A: Breslauer et al. (1986)
B: Delcourt and Blake (1991)
C: Doktycz et al. (1992)

TABLE 3

CALCULATED PARTIAL FREE-ENERGIES $$\Delta G_p = -\left[\sum_{i=1}^{N-1} \Delta G_{i,j+1} + \Delta G_{sym}\right], 25° C(kcal/mol)$$

| MOLECULE | A | B | C |
|---|---|---|---|
| N = 12 | | | |
| (AA)$_2$ (SEQ ID NO: 4) | 21.5 | 12.6 | 14.4 |
| (AT)$_2$ (SEQ ID NO: 3) | 15.7 | 12.6 | 13.1 |
| N = 16 | | | |
| (AA)$_3$ (SEQ ID NO: 2) | 29.3 | 16.5 | 19.2 |
| (AT)$_3$ (SEQ ID NO: 1) | 20.6 | 16.4 | 17.2 |
| (AA) (AT)$_2$ (SEQ ID NO: 5) | 23.5 | 16.4 | 17.9 |
| N = 20 | | | |
| (AA)$_4$ (SEQ ID NO: 7) | 37.1 | 20.4 | 24.0 |
| (AT)$_4$ (SEQ ID NO: 6) | 25.4 | 20.2 | 21.3 |

A: Breslauer et al. (1986)
B: Delcourt and Blake (1991)
C: Doktycz etal. (1992)

TABLE 4

EXPERIMENTAL THERMODYNAMIC PARAMETERS*

| MOLECULE | $-\Delta G_E$, 25 C. (kcal/mol) | | | $-\Delta H$ (kcal/mol) | | | $-\Delta S$ (cal/deg-mol) | | |
|---|---|---|---|---|---|---|---|---|---|
| | van't Hoff | calorimetry | average | van't Hoff | calorimetry | average | van't Hoff | calorimetry | average |
| (AA)$_2$ (SEQ ID NO: 4) | 8.9 | 4.0 | 6.5 | 58.6 | 54.3 | 56.5 | 166.7 | 168.7 | 168. |
| (AT)$_2$ (SEQ ID NO: 3) | 8.3 | 4.1 | 6.2 | 62.4 | 63.5 | 63.0 | 181.3 | 199.2 | 190. |
| (AA)$_3$ (SEQ ID NO: 2) | 11.9 | 7.0 | 9.5 | 77.6 | 78.4 | 78.0 | 220.4 | 239.4 | 230. |
| (AT)$_3$ (SEQ ID NO: 1) | 10.6 | 5.2 | 7.9 | 76.2 | 73.7 | 75.0 | 219.8 | 229.8 | 225. |
| (AA)(AT)$_2$ (SEQ ID NO: 5) | 10.9 | 5.9 | 8.3 | 75.1 | 76.2 | 75.7 | 215.3 | 235.7 | 226. |
| (AA)$_4$ (SEQ ID NO: 7) | 17.5 | 14.1 | 15.8 | 128.5 | 143.8 | 136.2 | 372.2 | 435.0 | 404. |
| (AT)$_4$ (SEQ ID NO: 6) | 15.2 | 10.0 | 13.2 | 127.5 | 118.1 | 123.5 | 376.7 | 362.8 | 370. |

*Obtained from multiple experiments, estimated errors in all values are approximately ± 3%.

TABLE 5

DUPLEX INITIATION FREE-ENERGIES

| | $\Delta G_{int} = \Delta G_E - \Delta G_p$, (kcal/mol) | | |
|---|---|---|---|
| MOLECULE | A | B | C |
| (AA)$_2$ (SEQ ID NO: 4) | 15.0 | 6.1 | 7.9 |
| (AT)$_2$ (SEQ ID NO: 3) | 9.5 | 6.4 | 6.9 |
| average: | 12.2 ± 2.8 | 6.2 ± 0.2 | 7.4 ± 0.5 |
| (AA)$_3$ (SEQ ID NO: 2) | 19.9 | 7.1 | 9.8 |
| (AT)$_3$ (SEQ ID NO: 1) | 12.7 | 8.5 | 9.3 |
| (AA)(AT)$_2$ (SEQ ID NO: 5) | 15.2 | 8.1 | 9.6 |
| average: | 15.9 ± 3.0 | 7.9 ± 0.6 | 9.6 ± 0.2 |
| (AA)$_4$ (SEQ ID NO: 7) | 21.3 | 4.6 | 8.2 |
| (AT)$_4$ (SEQ ID NO: 6) | 12.2 | 7.0 | 8.1 |
| average: | 16.8 ± 4.6 | 5.8 ± 1.2 | 8.2 ± 0.1 |
| Net Average: | 15.1 ± 3.9 | 6.8 ± 1.2 | 8.5 ± 1.0 |

A: Breslauer et al. (1986)
B: Delcourt and Blake (1991)
C: Doktycz et al. (1992)

TABLE 6

ALU I RATE CONSTANTS FOR SEVEN DUPLEX

| Olingonucleotide | Length (bp) | $K_{comp}$ (min$^{-1}$, × 10$^3$) | r |
|---|---|---|---|
| (AT)$_2$AGCT(AT)$_2$ (SEQ ID NO: 3) | 12 | 19.0 | 0.98 |
| (AA)$_2$AGCT(TT)$_2$ (SEQ ID NO: 4) | 12 | 6.3 | 0.95 |
| (AT)$_3$AGCT(AT)$_3$ (SEQ ID NO: 1) | 16 | 11.5 | 0.98 |
| (AA)$_3$AGCT(TT)$_3$ (SEQ ID NO: 2) | 16 | 3.9 | 0.97 |
| (AA)(AT)$_2$AGCT(AT)$_2$TT (SEQ ID NO: 5) | 16 | 7.7 | 0.99 |
| (AT)$_4$AGCT(AT)$_4$ (SEQ ID NO: 6) | 20 | 9.3 | 0.99 |
| (AA)$_4$AGCT(TT)$_4$ (SEQ ID NO: 7) | 20 | 3.1 | 0.95 |

TABLE 7

SUMMARY OF DIFFERENTIAL REACTIVITIES OF (AT)$_3$ (SEQ ID NO: 1) and (AA)$_3$ (SEQ ID NO: 2) WITH FOUR LIGANDS

| Ligand | Physical Quantity | Value |
|---|---|---|
| Alu I[a] | $k_{obs}((AT)_3)/k_{obs}((AA)_3)$ | ≈3 |
| Gilvocarin V[b] | $k_{adduct}((AT)_3)/k_{adduct}((AA)_3)$ | ≈2.5 |
| DNAse I[c] | $k_{obs}((AT)_3)/k_{obs}((AA)_3)$ | ≧2 |
| Actinomycin D[c] | $K_{eq}((AT)_3)/k_{eq}((AA)_3)$ | >2 |

[a]The present work
[b]Knobler, et al. (1992)
[c]Huang, et al. (1988)
$k_{obs}$ = composite rate constant for cleavage
$k_{adduct}$ = rate constant for UV induced adduct formation at [Gilvocarcin]/[DNA(bp)] = 1
$K_{eq}$ = estimated equilibrium binding constant from published data

V. References

1. Caruthers, M. H. *Chemical and Enzymatic Synthesis of Gene Fragments: A Laboratory Manual;* Gassen, H. G.; Lang, A., Eds.; Verlag-Chemie; Weinheim, FRG, 1982, pp. 71–79.
2. Caruthers, M. H. *Science* 1985, 230, 281–285.
3. Beaucage, S. L.; Caruthers, M. H. *Tetrahedron Lett.* 1981, 22, 1859–1862.
4. Benight, A. S.; Wang, Y. W.; Amaratunga, M.; Chattopadhyaya, R.; Henderson, J.; Hanlon, S.; Ikuta, S. *Biochemistry* 1989, 28, 3323–3332.
5. Shindo, H.; Okhubo, S.; Matsumoto, U.; Giessner-Prettre, C.; Zon, G. J. *Biomolec. Struct. and Dyn.* 1988, 5, 913–931.
6. Wolk, S.; Hardin, C. C.; Germann, M. W.; van de Sande, J. H.; Tinoco, I., Jr. *Biochemistry* 1988, 27, 6960–6967.
7. Xodo, L. E.; Manzini, G.; Quadrifoglio, F.; van der Marel, G. A.; van Boom, J. H. *Nucleic Acids Res.* 1986, 14, 5389–5398.
8. Xodo, L. E.; Manzini, G.; Quadrifoglio, F.; van der Marel, G. A.; van Boom, J. H. *Biochemistry* 1988, 27, 6321–6326.
9. Xodo, L. E.; Manzini, G.; Quadrifoglio, F.; van der Marel, G. A.; van Boom, J. H. *Biochemistry* 1988, 27, 6327–6331.
10. Antosiewicz, J.; Germann, M. W.; van de Sande, J. H.; Porschke, D. *Biopolymers* 1988, 27, 1319–1327.

11. Ikuta, S.; Chattopadhyaya, R.; Dickerson, R. E.; Kearns, D. R. *Biochemistry* 1986, 25, 4840–4849.
12. Germann, M. W.; Schoenwaedler, K.; van de Sande, J. H. *Biochemistry* 1985, 24, 5698–5702.
13. Wemmer, D. E.; Chou, S. H.; Hare, D. R.; Reid, B. R. *Nucleic Acids Res.* 1985, 13, 3755–3772.
14. Summers, M. F.; Byrd, R. A.; Gallo, K. A.; Samson, C. J.; Zon, G.; Egan, W. *Nucleic Acids Res.* 1985, 13, 6375–6386.
15. Hare, D. R.; Reid, B. R. *Biochemistry*, 1986, 25, 5341–5350.
16. Haasnoot, C. A. G.; de Hartog, J. H. J.; de Rooij, J. F. M.; van Boom, J. H.; Altona, C. *Nucleic Acids Res.* 1980, 8, 169–181.
17. Haasnoot, C. A. G.; de Bruin, S. H.; Brendsen, R. G.; Janssen, H. G. J. M.; Binnendiik, T. J. J.; Hilbers, C. W.; van der Marel, G. A.; van Boom, J. H. J. *Biomol. Struct. Dyn.* 1983, 1, 115–129.
18. Nadeau, J. D.; Gilham, P. T. *Nucleic Acids Res.* 1985, 13, 8259–8274.
19. Roy, S.; Weinstein, S.; Borah, B.; Nickol, J.; Apella, E.; Sussman, J.; Miller, M.; Shindo, H.; Cohen, J. S. *Biochemistry* 1986, 25, 7417–7423.
20. Marky, L. A.; Blumenfeld, K. S.; Kozlowski, S.; Breslauer, K. J. *Biopolymers* 1983, 22, 1247–1257.
21. Williamson, J. R.; Boxer, S. G. *Nucleic Acids Res.* 1988, 16, 1529–1540.
22. Williamson, J. R.; Boxer, S. G. *Biochemistry* 1989, 28, 2819–2831.
23. Williamson, J. R.; Boxer, S. G. *Biochemistry* 1989, 28, 2831–2836.
24. Chattopadhayaya, R.; Ikuta, S.; Grzeskowiak, K.; Dickerson, R. E. *Nature* 1988, 334, 175–179.
25. Pramanik, P.; Kanhouwa, N.; Kan, L. S. *Biochemistry* 1988, 27, 3024–3031.
26. Blommers, M. J. J.; Walters, J. A. L. I.; Haasnoot, C. A. G.; Aelen, J. M. A.; van der Marel, G. A.; van Boom, J. H.; Hilbers, C. W. *Biochemistry* 1989, 28, 7491–7498.
27. Senior, M. M.; Jones, R. A.; Breslauer, K. J. *Proc. Natl. Acad. Sci.* (USA) 1988, 85, 6242–6246.
28. Erie, D. A.; Suri, A. K.; Breslauer, K. J.; Jones, R. A.; Olson, W. K. *Biochemistry* 1993, 32, 436–454.
29. Amaratunga, M.; Pancoska, P.; Paner, T. M.; Benight, A. S. *Nucleic Acids Res.* 1990, 18, 577–582.
30. Paner, T. M.; Amaratunga, M.; Doktycz, M. J.; Benight, A. S. *Biopolymers* 1990, 29, 1715–1734.
31. Doktycz, M. J.; Paner, T. M.; Amaratunga, M.; Benight, A. S. *Biopolymers* 1990, 30, 829–845.
32. Rentzeperis, D.; Alessi, K.; Marky, L. A. *Nucleic Acids Res.* 1993, 21, 2633–2639.
33. Baxter, S. M.; Greizerstein, M. B.; Kuslan, D. M.; Ashley, G. W. *Biochemistry* 1993, 32, 8702–8711.
34. Hirao, I.; Nishimura, Y.; Tagawa, Y.; Watanabe, K.; Miura; K. *Nucleic Acids Res.* 1992, 20, 3891–3896.
35. Wemmer, D. E.; Benight, A. S. *Nucleic Acids Res.* 1985, 13,8611–8621.
36. Erie, D. E.; Sinha, N. K.; Olson, W. K.; Jones, R. A.; Breslauer, K. J. *Biochemistry* 1987, 26, 7150–7159.
37. Erie, D. E.; Jones, R. A.; Olson, W. K.; Sinha, N. K.; Breslauer, K. J. *Biochemistry* 1989, 28, 268–238.
38. Benight, A. S.; Schurr, J. M.; Flynn, P. F.; Reid, B. R. *J. Mol. Biol* 1988, 200, 377–399.
39. Schieferdecker, H.; Igloi, G. L.; Kössel, H. *Nucleosides and Nucleotides* 1988, 7, 751–755.
40. Snowden-Ifft, E. A.; Wemmer, D. E. *Biochemistry* 1990, 29, 6017–6025.
41. Ashley, G. W.; Kushlan, D. M. *Biochemistry* 1991, 30, 2927–2933.
42. Doktycz, M. J.; Goldstein, R. R.; Paner, T. M.; Gallo, F. J.; Benight, A. S. *Biopolymers* 1992, 32, 849–864.
43. Amaratunga, M.; Snowden-Ifft, E.; Wemmer, D. E.; Benight, A. S. *Biopolymers* 1992, 32, 865–879.
44. Paner, T. M.; Amaratunga, M.; Benight, A. S. *Biopolymers* 1992, 32, 881–892.
45. Goldstein, R. F.; Benight, A. S. *Biopolymers* 1992, 32, 1679–1693.
46. Doktycz, M. J.; Paner, T. M.; Benight, A. S. *Biopolymers* 1993, 33, 1765–1777.
47. Paner, T. M.; Gallo, F. J.; Doktycz, M. J.; Benight, A. S. *Biopolymers* 1993, 33, 1779–1789.
48. Rentzeperis, D.; Ho, J.; Marky, L. A. *Biochemistry* 1993, 32, 2564–2572.
49. Rentzeperis, D.; Kharakoz, D.; Marky, L. A. *Biochemistry* 1991, 30, 6276–6283.
50. Van de Sande, J. H.; Ramsing, N. B.; Germann, M. W.; Elhorst, W.; Kalisch, B. W.; Kitzing, E. V.; Pon, R. T.; Clegg, R. C.; Jovin, T. M. *Science* 1988, 241, 551–557.
51. Ramsing, N. B.; Jovin, T. M. *Nucleic Acids Res.* 1988, 16, 6659–6676.
52. Germann, M. W.; Kalisch, B. W.; Pon, R. T.; van de Sande, J. H. *Biochemistry* 1990, 29, 9426–9432.
53. Shchyolkina, A. K.; Lysov, Yu. P.; Il'ichova, I. A.; Chemyi, A. A.; Golova; Yu. B.; Chernov, B. K.; Gottikh, B. P.; Florentiev, V. L. *FEBS Letts* 1989, 244, 39–42.
54. Rippe, K.; Fritsch, V.; Westhof, E.; Jovin, T. M. *EMBO J.* 1992, 11, 3777–3786.
55. Luo, J.; Sharma, M. H.; Yuan, R-D.; Sharma, R. H. *FEBSLetts* 1992, 306, 223–228.
56. Plum, G. E.; Park, Y-W.; Singleton, S. F.; Dervan, P. B.; Breslauer, K. *J. Proc. Natl. Acad. Sci.* (USA) 1990, 87, 9436–9440.
57. Rajagopal, P.; Feigon, J. *Nature* 1989, 339, 637–640.
58. Shea, R. G.; Ng. P.; Bischofberger, N. *Nucleic Acids Res.* 1990, 18, 4859–4866.
59. Mooren, M. M. W.; Pulleyblank, D. E.; Wijmenga, S. S.; Blommers, M. J. J.; Hilbers, C. W. *Nucleic Acids Res.* 1990, 18, 6523–6529.
60. Kool, E. T. *J. Am. Chem. Soc.* 1991, 113, 6265–6266.
61. Pilch, D. S.; Brousseau, R.; Shafer, R. H. *Nucleic Acids Res.* 1990, 18, 5743–5750.
62. Kan, L.-S.; Callahan, D. E.; Trapane, T. L.; Miller, P. S.; Tsto; P. O. P.; Huang, D. H. *J. Biomolec. Struct. and Dynam.* 1991, 8, 911–933.
63. Roberts, R. W.; Crothers, D. M. *Proc. Natl. Acad. Sci.* (USA) 1991, 88, 9397–9401.
64. Häner, R.; Dervan, P. *Biochemistry* 1990, 29, 9761–9765.
65. Lee, J. S.; Woodsworth, M. L.; Latimer, L. J. P.; Morgan, A. R. *Nucleic Acids Res.* 1984, 12, 6603–6614.
66. Xodo, L. E.; Manzini, G.; Quadrifoglio, F. *Nucleic Acids Res.* 1984, 18, 3557–3564.
67. Manzini, G.; Xodo, L. E.; Gasparotto, D.; Quadrifoglio, F.; van der Marel, G. A.; van Boom, J. H. *J. Mol. Biol.* 1990, 213, 833–843.
68. Macaya, R.; Wang, E.; Schultze, P; Sklenar; Feigon, J. *J. Mol. Biol.* 1992, 225, 755–773.
69. Cheng, Y-K.; Pettitt, B. M. *Prog Biophys. Molec. Biol.* 1992, 58, 225–257.
70. Smith, F. W.; Feigon, J. *Nature* 1992, 356, 164–168.
71. ChulHee, K.; Zhang, X.; Ratliff, R.; Moyzis, R.; Rich, A. *Nature* 1992, 356, 126–131.
72. Lu, M.; Guo, Q.; Kallenbach, N. R. *Biochemistry* 1992, 31, 2455–2459.
73. Guo, Q.; Lu, M.; Kallenbach, N. R. *Biochemistry* 1993, 32, 3596–3603.

74. Williamson, J. R.; Raghuraman, M. K.; Cech, T. R. *Cell* 1989, 59, 871–880.
75. Piccirilli, J. A.; Krauch, T.; Moroney, S. E.; Benner, S. A. *Nature* 1990, 343, 33–37.
76. Telser J.; Cruickshank, K. A.; Morrison, L. E.; Netzel, T. L. *J. Am. Chem. Soc.* 1989, 111, 6966–6976.
77. Smith, L, M.; Sanders, J. Z.; Kaiser, R. J.; Hughes, P.; Dodd, C.; Connell, C. R.; Heiner, C.; Kent, S. B. H.; Hood, L. E. *Nature* 1986, 321, 674–679.
78. Spaltenstein, A.; Robinson, B. H.; Hopkins, P. B. *Biochemistry* 1989, 28, 9484–9489.
79. Shea, R. G.; Marsters, J. C.; Bischofberger, N. *Nucleic Acids Res.* 1990, 18, 3777–3783.
80. Fidanza, J. A.; Mclaughlin, L. W., *J. Am. Chem. Soc.* 1989, 111, 9117–9119.
81. Asseline, U.; Thuong, N. T. *Tetrahedron Lett.* 1990, 31, 81–84.
82. Agrawal, S.; Christodoulou, C.; Gait, M. *J. Nucl. Acids Res.* 1986, 14, 6227–6245.
83. Mori, K.; Subasinghe, C. A.; Stein, C. A.; Cohen, J. S. *Nucleosides and Nucleotides* 1989, 8, 649–657.
84. Connolly, B. A. *Nucleic Acids Res.* 1985, 13, 4885–4502.
85. Chu, B. C. F.; Orgel, L. E. Proc. *Natl. Acad. Sci.* (USA) 1985, 82, 963–967.
86. Kremsky, J. N.; Wooters, J. L.; Dougherty, J. P.; Meyers, R. E.; Collins, M.; Brown, E. L. *Nucleic Acids Res.* 1987, 15, 2891–2909.
87. Wartell, R. M.; Benight, A. S. *Phys. Rep.* 1985, 126, 67–107.
88. Delcourt, S. G.; Blake, R. D. *J. Biol. Chem.* 1991, 266, 15160–15169.
89. Hillen, W.; Goodman, T. C.; Benight, A. S.; Wartell, R. M.; Wells, R. D. *J. Biol. Chem.* 1981, 256, 2761–2766.
90. Fried, M.; Crothers, D. M. *Nucleic Acids Res.* 1981, 9, 6505–6525.
91. Kim, U.-S.; Fujimoto, B. S.; Furlong, C. E.; Sundstrom, J. A.; Humbert, R.; Teller, D. C.; Schurr, J. M. *Biopolymers* 1993, 33, 1725–1745.
92. Perelroyzen, M. P.; Lyamichev, V. I.; Kalambet, Y. A.; Lyubchenko, Y. L.; Vologodskii, A. V. *Nucleic Acids Res.* 1981, 9, 4043–4059.
93. Tong, B. T.; Battersby, S. J. *Biopolymers* 1979, 18, 1917–1936.
94. McCampbell, C. R.; Wartell, R. M.; Plaskon, R. R. *Biopolymers* 1989, 28, 1745–1758.
95. Poland, D. *Biopolymers* 1974, 13, 1859–1871.
96. Wada, A.; Yubuki, S.; Husimi, Y. *CRC Crit. Rev. Biochem.* 1980, 9, 87–144.
97. Gotoh, O., *Adv. Biophys.* 1983, Kotani, M., Ed; 16, 1–52
98. Gotoh, O.; Tagashira, Y. *Biopolymers* 1981, 20, 1033–1042.
99. Vologodskii, A. V.; Arnirikyan, B. R.; Lyubchenko, Y. L.; Frank-Kamenetskii, M. D. *J. Biomolec. Strut. and Dynam.* 1984, 2, 131–148.
100. Breslauer, K. J.; Frank, R.; Blocker, H.; Marky, L. A. *Proc. Natl. Acad. Sci.* (USA) 1986, 83, 3746–3650.
101. Huang, Y. -Q.; Rehfuss, R. P.; Laplante, S. R.; Boudreau, E.; Borer, P. N.; Lane, M. J. *Nucleic Acids Res.* 1988, 16, 11125–11139.
102. Lane, M. J.; Bishop, K. D.; Borer, P. N.; Radlwimmer, F. B. *Biophysical J.* 1992, 61, A221.
103. Hogan, M.; Roberson, M. W.; Austin, R. H. *Proc. Natl. Acad. Sci.* (USA) 1989, 86, 9273–9277.
104. Waterloh, K.; Fox, K. R. *J. Biol. Chem.* 1991, 266, 6381–6388.
105. Lyubchenko, Y. L.; Frank-Kamenetskii, M. D.; Vologodskii, A. V.; Luzurkin, Y.; Gause, G. G., Jr. *Biopolymers* 1976, 15, 1019–1036.
106. Poland, D.; Scheraga, H. A. *Theory of Helix-Coil Transitions in Biopolymers; Academic;* New York, 1970.
107. Wartell, R. M.; Montroll, E. W. *Adv. Chem. Phys.* 1972, 22, 129–203.
108. Wartell, R. M.; Benight, A. S. *Biopolymers* 1982, 21, 2069–2081.
109. Marmur, J.; Doty, P. *J. Mol. Biol.* 1962, 5, 109–118.
110. Owen, R. J.; Hill, L. R.; LaPage, S. P. *Biopolymers* 1969, 7, 503–521.
111. Frank-Kamenetskii, M. D. *Biopolymers* 1971, 10, 2623–2624.
112. Klump, H. H.; *Studies in Modern Thermodynamics* 8: *Biochemical Thermodynamics* ($2^{nd}$ Ed), Jones, M. N., ed; Elsevier; Amsterdam, 1988, pp. 100–144.
113. Klump, H. H.; Ackerman, T. *Biopolymers* 1971, 10, 513–522.
114. Defoe, H.; Tinoco *J. Mol. Biol.* 1962, 4, 500–517.
115. Vesnaver, G.; Breslauer, K. *J. Proc. Natl. Acad. Sci.* (USA) 1991, 88, 3569–3573.
116. Kozyavkin, S. A.; Lyubchenko, Y. L. *Nucleic Acids Res.* 1984, 12, 4339–4349.
117. Lyubchenko, Y. L.; Vologodskii, A. V.; Frank-Kamenetskii, M. D. *Nature* 1978, 271, 28–31.
118. Vizard, D. L.; White, R. A.; Ansevin, A. T. *Nature* 1978, 275, 251–251.
119. Wada, A.; Tachibana, H.; Ueno, A.; Husimi, V.; Machida, Y. *Nature* 1977, 269, 352–353.
120. Tachibana, H.; Wada, A.; Gotoh, O.; Takanami, M. *Biochim. Biophys. Acta* 1978, 517, 319–328.
121. Gabbarro-Arpa, J.; Tougard, P.; Reiss, C. *Nature* 1979, 280, 515–517.
122. Turner, D. H.; Sugimoto, N. *Ann. Rev. Biophys. and Biophys. Chem.* 1988, 17, 167–192.
123. Gray, D. M.; Tinoco, I. Jr. *Biopolymers* 1970, 9, 223–244.
124. Press, W. H.; Flannery, B. P.; Teukolsky, S. A.; Vetterling, W. T. *Numerical Recipes*; Cambridge University Press, New York, 1989, pp. 52–64, 472–476.
125. King, G. *Nucleic Acids Res.* 1993, 21, 4239–4245.
126. Williams, D. L.; Kowalski, D. J. *Virology* 1993, 67, 2707–2715.
127. Lin, S.; Kowalski, D. *J. Mol. Biol.* 1994, 235, 496–507.
128. Sutcliffe, J. G. *Cold Springs Harb. Symp. Quant. Biol.* 1978, 43, 77–90.
129. Marky, L. A.; Breslauer, K. J. *Biopolymers* 1987, 26, 1601–1620.
130. Cantor, C.; Warshaw, M. W.; Shapiro, H. *Biopolymers* 1970, 9, 1059–1077.
131. Benight, A. S.; Wartell, R. M.; Howell, D. K. *Nature* 1981, 289, 203–205.
132. Neidle, S.; Abraham, Z. CRC Crit. *Rev. Biochem.* 1984, 17, 73–121.
133. Crothers, D. M.; Dattagupta, N.; Hogan, M. *Nucleic Acid Geometry and Dynamics;* Sharma, R. H., Ed.; Pergamon, 1980, 341–349.
134. Dougherty, G.; Pigram, W. J.; CRC Crit. *Rev. Biochem.* 1982, 12, 103–141.
135. Berman, H. M.; Young, P. R. *Annu. Rev. Biophys. Bioeng* 1981, 10, 87–114.
136. Patel, D. J. *Nucleic Acid Geometry and Dynamics;* Sharma, R. H., Ed.; Pergamon, 1980, 185–231.
137. Blakesly, R. W. *Gene Amplification and Analysis;* Chirikjian, J. G., Ed.; Elsevier, N.Y., 1987, 51–102.
138. Burd, J. F.; Wartell, R. M.; Dodgson, J. B.; Wells, R. D.; *J. Biol. Chem.* 1975, 250, 5109–5113.
139. Wartell, R. M.; Burd, J. F. *Biopolymers* 1976, 15, 1461–1479.

140. Wartell, R. M. *Nucleic Acids Res.* 1977, 4, 2779–2797.
141. Hogan, M.; Dattagupta, N.; Crothers, D. M. *Nature* 1979, 278, 521–524.
142. Winkle, S. A.; Krugh, T. R. *Nucleic Acids Res.* 1981, 9, 3175–3186.
143. von Hippel, P. H.; Berg, O. G. *J. Biol. Chem.* 1989, 264, 675–678.
144. Tullius, T. D. *Annu. Rev. Biophys. Chem.* 1989, 18, 213–237.
145. McGhee, J. D.; von Hippel, P. H. *J. Mol. Biol.* 1974, 86, 469–489.
146. Lane, M. J.; Dabrowiak, J. C.; Voumakis, J. D. *Proc. Natl. Acad. Sci.* (USA) 1983, 80, 3260–3264.
147. Scott, E. V.; Zon, G.; Marzilli, L. G.; Wilson, W. D. *Biochemistry* 1988, 27, 7940–7951.
148. Scott, E. V.; Jones, R. L.; Banville, D. L.; Zon, G.; Wilson, W. D. *Biochemistry* 1988, 27, 915–923.
149. Miller, K. J.; Rein, F. H.; Taylor, E. R.; Kowalczyk, P. J. *Ann.* New York Acad. Sci. 1985, 439, 64–80.
150. Neidle, S.; Pearl, L. H.; Shelly, J. V. *Biochem. J.* 1987, 243, 1–13.
151. Travers, A. A. Ann. Rev. *Biochem.* 1989, 58, 427–452.
152. Harrison, S. C. *Nature* 1991, 353, 715–719.
153. Lu, M.; Guo, Q.; Kallenbach, N. R. CRC Crit. *Rev. Biochem. Mol. Biol.* 1992, 27, 157–190.
154. Palacek, E. CRC Crit. *Rev. Biochem. Mol. Biol.* 1991, 26, 151–226.
155. Galas, D. J.; Schrnitz, A. *Nucleic Acids Res.* 1978, 5, 3157–3172.
156. Portugal, J. *FEBS Letts* 1989, 251, 8–12.
157. Ackers, G. K.; Johnson, A. D.; Shea, M. *Proc. Natl. Acad. Sci. (USA)* 1982, 79, 1129–1133.
158. Brenowitz, M.; Senear, D. F.; Shea, M.; Ackers, G. K. *Meth. Enzymol.* 1986, 130, 132–181.
159. Johnson, A. D.; Meyer, B. J.; Ptashne, M. *Proc. Natl. Acad. Sci.* (USA) 1979, 76, 1608–1612.
160. Hochschild, A.; Ptashne, M. *Cell* 1986, 44, 681–687.
161. Koudelka, G. B.; Harrison, S. B.; Ptashne, M. *Nature* 1987, 326, 886–888.
162. Fish, E. L.; Lane, M. J.; Vournakis, J. N. *Biochemistry* 1988, 27, 6026–6032.
163. Rehfuss, R.; Goodisman, J.; Dabrowiak, J. C. *Biochemistry* 1989, 29, 777–781.
164. Goodisman, J.; Dabrowiak, J. C. *Biochemistry* 1992, 31, 1058–1064.
165. Goodisman, J.; Rehfuss, R.; Ward, B.; Dabrowiak, J. C. *Biochemistry* 1992, 31, 1046–1058.
166. Dabrowiak, J. C.; Goodisman, J.; Kissinger, K. *Biochemistry* 1990, 29, 6139–6145.
167. Ward, B.; Rehfuss, R.; Goodisman, J.; Dabrowiak, J. C. *Nucleic Acids Res.* 1988, 16, 1359–1369.
168. Ward, B.; Rehfuss, R.; Dabrowiak, J. C. *J. Biomol. Struct. Dyn.* 1987, 4, 685–695.
169. Ward, B.; Rehfuss, R.; Dabrowiak, J. C. *Biochemistry* 1988, 27, 1198–1205.
170. Thomas, C. A. *J. Am. Chem. Soc.* 1956, 78, 1861–1868.
171. Fersht, A. *Enzyme Structure and Mechanism;* Freeman; New York, 1985, ed. 2, chapter 3.
172. Low, C. M. L.; Drew, H. R.; Waring, M. *J. Nucleic Acids Res.* 1984, 12, 4865–4879.
173. Van Dyke, M. W.; Hertzberg, R. P.; Dervan, P. B. *Proc. Natl. Acad. Sci.* (USA) 1982, 79, 5470–5474.
174. Lane, M. J.; Laplante, S.; Rehfuss, R. P.; Borer, P. N.; Cantor, C. R. *Nucleic Acids Res.* 1987, 15, 839–852.
175. Bishop, K. D.; Borer, P. N.; Huang, Y.-Q.; Lane, M. *J. Nucleic Acids Res.* 1991, 19, 871–875.
176. Goldstein, K.; Thomas, M.; Davis, R. W. *Virology* 1975, 66, 420–427.
177. Armstrong, K.; Bauer, W. K. *Nucleic Acids Res.* 1982, 10, 993–1007.
178. Alves, J.; Pingoud, A.; Haupt, W.; Langowski, J.; Peters, F.; Maass, G.; Wolff, C. *Eur, J. Biochem.* 1984, 140, 83–92.
179. Drew, H. R.; Travers, A. A. *Nucleic Acids Res.* 1985, 13, 4445–4456.
180. Richter, P. H.; Eigen, M. *Biophys. Chem.* 1974, 2, 255–263.
181. Berg, O. G.; Winter, R. B.; von Hippel, P. H. *Biochemistry* 1981, 20, 6929–6948.
182. Jack, W. E.; Terry, B. J.; Modrich, P. *Proc. Natl. Acad. Sci.* (USA) 1982, 79, 4101–4014.
183. Ehbrect, H.; Pingoud, A.; Urbanke, C.; Maass, G.; Gaulerzi, C. *J. Biol. Chem.* 1985, 260, 6160–6166.
184. Terry, B. J.; Jack, W. E.; Modrich, P. *Gene Amplification and Analysis;* Chirikjian, J. G., Ed.; Elsevier; N.Y. 1987, 5, 51–102.
185. Lesser, D. R.; Kurpiewski, M. R.; Jen-Jacobsen, L. *Science* 1990, 250, 776–786.
186. Lesser. D. R.; Kurpiewski, M. R.; Waters, T.; Connolly, B. A.; Jen-Jacobsen, L. *Proc. Natl. Acad Sci.* (USA) 1993, 90, 7548–7552.
187. Snyder, J. G.; Hartman, N. G.; D'Estantoit, B. L.; Kennary, O.; Remeta, D. P.; Breslauer, K. *J. Proc. Natl. Acad. Sci.* (USA) 1989, 86, 3968–3972.
188. McGee, J. D. *Biopolymers* 1976, 15, 1345–1375.
189. Spolar, R. S.; Record, M. T., Jr. *Science* 1994, 263, 777–784.
190. Nakano, H.; Matsuda, Y.; Itol, K.; Ohkubo, S.; Morimoto, M.; Tomita, F. *J. Antibiotics* 1981, 34, 271–275.
191. Tse-Dinh, Y. -C.; McGee, L. R. *Biochem. Biophys. Res. Comm.* 1987, 143, 808–812.
192. Herrera, J. E.; Chaires, J. B. *J. Mol. Biol.* 1994, 236, 405–411.
193. McCarin, J. A.; Frederick, C. A.; Wang, B. C.; Greene, P. J.; Boyer, H. W.; Grable, J.; Rosenberg, J. M. *Science* 1986, 234, 1526–1541.
194. Kim, Y. C.; Grable, J. C.; Love, R.; Green, P. J.; Rosenberg, J. M. *Science* 1990, 249, 1307–1309.
195. Thielking, V.; Alves, J.; Fliess, A.; Maass, G.; Pingoud, A. *Biochemistry* 1990, 29, 4682–4691.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 16 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:1:

ATATATAGCT ATATAT                                                    16

(2) INFORMATION FOR SEQ ID NO:2:

(i) SEQUENCE CHARACTERISTICS:
          (A) LENGTH: 16 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:2:

AAAAAAAGCT TTTTTT                                                    16

(2) INFORMATION FOR SEQ ID NO:3:

(i) SEQUENCE CHARACTERISTICS:
          (A) LENGTH: 12 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:3:

ATATAGCTAT AT                                                        12

(2) INFORMATION FOR SEQ ID NO:4:

(i) SEQUENCE CHARACTERISTICS:
          (A) LENGTH: 12 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:4:

AAAAAGCTTT TT                                                        12

(2) INFORMATION FOR SEQ ID NO:5:

(i) SEQUENCE CHARACTERISTICS:
          (A) LENGTH: 16 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:5:

```
AAATATAGCT ATATTT                                                    16

(2) INFORMATION FOR SEQ ID NO:6:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:6:

ATATATATAG CTATATATAT                                                20

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:7:

AAAAAAAAAG CTTTTTTTTT                                                20

(2) INFORMATION FOR SEQ ID NO:8:

(i) SEQUENCE CHARACTERISTICS:
         (A) LENGTH: 16 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:8:

GTATCCNNNN GGATAC                                                    16
```

Other embodiments are within the following claims.

What is claimed is:

1. A method of preparing a first double-strand nucleic acid comprising a first binding site for a nucleic acid-binding ligand, wherein a first value of a first free energy parameter for said first double-strand nucleic acid has a preselected relationship with a first reference value of the first free energy parameter for a reference double-strand nucleic acid comprising a reference binding site for the ligand; the first free energy parameter is a characteristic of the binding of a ligand of interest to its binding site; and the preselected relationship is higher than, equal to or lower than, said method comprising:

(a) determining a test value for a test double-strand nucleic acid, comprising a test binding site for the ligand, of a second free energy parameter that is characteristic of the hybridization of the two complementary strands of a double-strand nucleic acid;

(b) comparing the test value to a reference value (second reference value) of the second free energy parameter for the reference double-strand nucleic acid; and (c) if the test value and the second reference value of the second free energy parameter exhibit a test relationship that is the same as the preselected relationship, then preparing a first double-strand nucleic acid comprising all or part of the test nucleic acid, but if the test relationship is different than the preselected relationship, repeating steps (a) and (b) on one or more additional test double-strand nucleic acids until an additional test double-strand nucleic acid is identified wherein the test relationship is the same as the preselected relationship, and then preparing a first double-strand nucleic acid comprising all or part of the additional test nucleic acid.

2. The method of claim 1, wherein the test and the reference binding sites are not identical.

3. The method of claim 1, wherein the test nucleic acid further comprises a first flanking sequence that is adjacent to the test binding site, the reference nucleic acid further comprises a reference flanking sequence that is adjacent to the reference binding site, and the test and reference binding sites are identical.

4. The method of claim 3, wherein the rest and reference binding sites are less than 100 base pairs in length.

5. A method of optimizing the ligand binding affinity of a binding site for its nucleic acid-binding ligand when the binding site is present in double-strand nucleic acid, wherein optimal ligand binding affinity is either higher or lower than a reference ligand binding affinity, said method comprising the steps:

(a) permuting the sequence of a reference double-strand nucleic acid to give a test nucleic acid, wherein the reference nucleic acid is either the binding site or a sequence flanking the binding site in a reference double-strand nucleic acid;

(b) determining a test value for the test nucleic acid of a free energy parameter that is characteristic of the binding affinity of the two complementary strands of a double-strand nucleic acid, hereafter, duplex binding affinity;

(c) comparing the test value to a reference value of the free energy parameter for the reference nucleic acid; and (d) if the test value is characteristic of higher or lower duplex binding affinity than the reference value and optimal ligand binding affinity is lower or higher, respectively, than the reference ligand binding affinity, then replacing the reference nucleic acid sequence in the reference double-strand nucleic acid with the test nucleic acid, otherwise;

(e) repeating steps (a) through (d).

6. The method of claim 5, wherein the binding site is less than 100 base pairs in length.

* * * * *